(12) United States Patent
Knust et al.

(10) Patent No.: US 8,133,909 B2
(45) Date of Patent: Mar. 13, 2012

(54) HETEROAROMATIC MONOAMIDES AS OREXININ RECEPTOR ANTAGONISTS

(75) Inventors: Henner Knust, Rheinfelden (DE); Matthias Nettekoven, Grenzach-Wyhlen (DE); Emmanuel Pinard, Linsdorf (FR); Olivier Roche, Folgensbourg (FR); Mark Rogers-Evans, Bottmingen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 89 days.

(21) Appl. No.: 12/481,627

(22) Filed: Jun. 10, 2009

(65) Prior Publication Data

US 2009/0312314 A1    Dec. 17, 2009

(30) Foreign Application Priority Data

Jun. 16, 2008  (EP) .................................... 08158332

(51) Int. Cl.
*A61K 31/44* (2006.01)
*C07D 213/02* (2006.01)
(52) U.S. Cl. ........ 514/357; 546/329; 546/334; 546/336; 514/277
(58) Field of Classification Search .................. 546/329, 546/334, 336; 514/357
See application file for complete search history.

(56) References Cited

U.S. PATENT DOCUMENTS

| | | | | |
|---|---|---|---|---|
| 3,366,674 A | * | 1/1968 | Geiger ............................ | 562/585 |
| 5,223,529 A | * | 6/1993 | Bourzat et al. ................. | 514/414 |
| 5,382,590 A | * | 1/1995 | Bourzat et al. ................. | 514/396 |
| 6,436,923 B1 | | 8/2002 | Bhagwat et al. | |
| 7,501,541 B2 | * | 3/2009 | Gobbi et al. .................... | 564/156 |
| 7,678,785 B2 | * | 3/2010 | Carr et al. ................. | 514/210.17 |
| 7,829,563 B2 | * | 11/2010 | Gobbi et al. ............. | 514/252.01 |

FOREIGN PATENT DOCUMENTS

| | | |
|---|---|---|
| WO | WO 00/00489 | 1/2000 |
| WO | WO 03/063794 | 8/2003 |
| WO | WO 2005/037830 | 4/2005 |
| WO | WO 2005/118548 | 12/2005 |
| WO | WO 2005/123748 | 12/2005 |
| WO | WO 2006/110626 | 10/2006 |
| WO | WO 2008/110488 | 9/2008 |
| WO | WO 2009/016087 | 2/2009 |

OTHER PUBLICATIONS

Geiger Suzanne (1968): STN International HCAPLUS database, (Columbus, Ohio), Accession No. 1968:95556.*
Siegel, Annu Rev. Psychol. vol. 55, pp. 125-148 (2004).
DeLecea et al., Proc. Natl. Acad. Sci. USA vol. 95 pp. 322-327 (1998).
Sakurai et al., Cell vol. 92, pp. 573-585 (1998).
Sakurai, Regulatory Peptides vol. 126 pp. 3-10 (2005).
Peyron et al., J. Neurosci. vol. 18, pp. 9996-10015 (1998).
Nambu et al., Brain Res. vol. 827 pp. 243-260 (1999).
Chemelli et al., Cell, vol. 98 pp. 437-451 (1999).
Lin et al., Cell. vol. 98 pp. 365-376 (1999).
Nishino et al., Lancet vol. 355 pp. 39-40 (2000).
Peyron et al., Nature Medicine vol. 6 pp. 991-997 (2000).
Mignot et al., Sleep vol. 11 pp. 1012-1020 (1997).
Piper et al., Eur. J. Neuroscience vol. 12, pp. 726-730 (2000).
Sakamoto et al., Regul. Pept. vol. 118, pp. 183-191 (2004).
Ida et al., Biochem. Biophys. Res. Comm. vol. 270, pp. 318-323 (2000).
Kuru et al., Neuroreport vol. 11 pp. 1977-1980 (2000).
Winsky Sommerer et al., J. Neuroscience vol. 24 pp. 11439-11448 (2004).
Suzuki et al., Brain Research vol. 1044, pp. 116-121 (2005).
Digby et al., J. Endocrinol. vol. 191 pp. 129-136 (2006).
Cai, et al., Expert Opin. Ther. Patents vol. 16(5) pp. 631-646 (2006).
Bingham et al., Current Opinion in Drug Discovery & Development vol. 9(5) pp. 551-559 (2006).
J. Neurosci. vol. 20(20) pp. 7760-7765 (2000).
Smith, et al., Neurosci. Lett. vol. 341(3) pp. 256-258 (2003).
Malherbe et al., Mol. Pharmacol. vol. 64 pp. 823-832 (2003).
Chaudhari et al., Synlett, vol. 11, pp. 1763-1765 (1999).

* cited by examiner

*Primary Examiner* — Golam M M Shameem
(74) *Attorney, Agent, or Firm* — George W. Johnston; Patricia S. Rocha-Tramaloni; Kimberly J. Prior

(57) ABSTRACT

The present invention is concerned with novel sulfonamides of formula

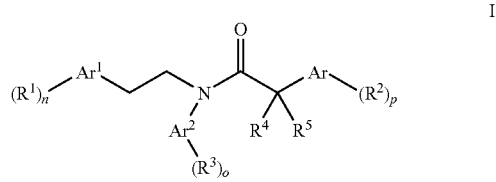

wherein $R^1$, $R^2$, $R^3$, $R^4$, $R^5$, Ar, $Ar^1$, $Ar^2$, n, o and p are as described in the description and claims. The compounds are orexin receptor antagonists that may be useful in the treatment of disorders, in which orexin pathways are involved.

37 Claims, No Drawings

HETEROAROMATIC MONOAMIDES AS OREXININ RECEPTOR ANTAGONISTS

PRIORITY TO RELATED APPLICATION(S)

This application claims the benefit of European Patent Application No. 08158332.0, filed Jun. 16, 2008, which is hereby incorporated by reference in its entirety.

BACKGROUND OF THE INVENTION

Orexins (hypocretins), a family of hypothalamic neuropeptides, play an important role in modulating feeding behavior, energy homeostasis and the sleep-wake cycle (Siegel, *Annu. Rev. Psychol.*, 55, 125-148, 2004). The orexin-A/hypocretin1 (OX-A, 33 amino acids) and orexin-B/hypocretin2 (OX-B, 28 amino acids) are derived from the same precursor by proteolytic processing of 130 amino acids prepro-orexin (de Lecea et al., *Proc Natl Acad Sci USA*, 95, 322-327, 1998; Sakurai T. et al., *Cell*, 92, 573-585, 1998). The orexin levels show a diurnal variation being highest during the active cycle. Two receptor subtypes termed orexin-1 receptor ($OX_1R$) and orexin-2 receptor ($OX_2R$) have been identified. The characterization of both receptors in binding and functional assays demonstrated that $OX_2R$ is a non-selective receptor for both OX-A and -B, whereas $OX_1R$ is selective for OX-A, conversely OX-A is a non-selective neuropeptide and binds with similar affinities to $OX_1R$ and $OX_2R$, while OX-B is selective and has a higher affinity for OX2R (Sakurai T. et al., *Cell*, 92, 573-585, 1998). Both receptors belong to the class A family of G-protein-coupled receptors (GPCRs) that couple via $G_{q/11}$ to the activation of phospholipase C leading to phosphoinositide (PI) hydrolysis and elevation of intracellular $Ca^{2+}$ levels. However, it has been shown that OX2R could also couple via $G_{i/o}$ to cAMP pathway (Sakurai, *Regulatory Peptides*, 126, 3-10, 2005). Northern blot analysis of adult rat tissues showed that the prepro-orexin mRNA is detected exclusively in the brain (except for a small amount in the testis) and that the $OX_1R$ and $OX_2R$ transcripts are also exclusively detected in the brain (Sakurai T. et al., *Cell*, 92, 573-585, 1998). Similar results were obtained using human multiple tissue Northern blot. Distribution studies in rat brain using in situ hybridization and immunohistochemistry have shown that orexin neurons are found only in the lateral hypothalamic area with their projections to the entire CNS (Peyron et al., *J Neurosci*, 18, 9996-10015, 1998; Nambu et al., *Brain Res.*, 827, 243-60, 1999). In addition, both $OX_1$ and $OX_2$ receptors are present in brain regions important for the regulation of sleep/wakefulness.

A disrupted orexin system is suggested to be the cause of narcolepsy based on following lines of evidence: (a) Prepro-orexin knockout mice possessed a phenotype with characteristics remarkably similar to narcolepsy (Chemelli et al., *Cell*, 98, 437-451, 1999), (b) a mutation (canarc-1), which disrupts the gene encoding $OX_2R$, was found to be responsible for canine narcolepsy (Lin et al., *Cell*, 98, 365-376, 1999), (c) lack of OX-A and OX-B was observed in human narcoleptic patients (Nishino et al., *Lancet*, 355, 39-40, 2000; Peyron et al., *Nature Medicine*, 6, 991-997, 2000), (d) it has been shown that Modafinil, an anti-narcoleptic drug with unknown mechanism of action, activates orexin neurons (Mignot et al., *Sleep*, 11, 1012-1020, 1997; Chemelli et al., *Cell*, 98, 437-451, 1999). The intracebroventricular (icv) administration of OX-A dose-dependently increases wakefulness in rat and also reduces total REM sleep by 84% (Piper et al., *Eur. J. Neuroscience*, 12, 726-730, 2000). Taken together, these observations are consistent with a crucial role of the orexin system in the modulation of sleep/wake cycle.

Orexin plays an important role in stress and anxiety via its interaction with the corticotropin-releasing factor (CRF) system in hypothalamus (Sakamoto et al., *Regul Pept.*, 118, 183-91, 2004). The icv injection of OX-A induces grooming (stress-response) which is blocked in part by a CRF antagonist (Ida et al., *Biochem. Biophys. Res. Comm.*, 270, 318-323, 2000). $OX_2R$ is highly expressed in adrenal medulla, whereas $OX_1R$ is high in adrenal cortex. Both OX-A and OX-B stimulate corticosterone release in plasma and induce c-Fos in paraventricular nucleus (PVN) in the hypothalamus (Kuru et al., *Neuroreport*, 11, 1977-1980, 2000). Furthermore, orexin neurons projecting to CRF neurons express mainly the $OX_2R$ (Winsky-Sommerer et al., *J. Neuroscience*, 24, 11439-11448, 2004). Therefore, OX2R stimulation activates the hypothalamo-pituitary-adrenal (HPA) axis. Interestingly, in this context, the orexin A-induced increases in plasma ACTH has been reported to be attenuated by a selective antagonist to OX-2R (N-{(1S)-1-(6,7-dimethoxy-3,4-dihydro-2(1H)-isoquinolinyl)carbonyl}-2,2-dimethylpropyl)-N-{4-pyridinylmethyl}amine (Chang et al., *Neurosci Res.*, 21 Dec. 2006). A recent preclinical report (Suzuki et al., *Brain Research*, 1044, 116-121, 2005) has suggested an anxiogenic effect of OX-A. The icv injection of OX-A caused an anxiety-like behavior in mice. Effects were similar to those of corticotropin-releasing factor (CRF) that was tested at the same time for comparison. A recent study has also demonstrated the presence of functional OX1 and OX2 receptors in human adipose tissue and their roles in adipose tissue metabolism and adipogenesis (Digby et al., *J. Endocrinol.*, 191, 129-36, 2006).

In summary, considering the very diverse functions played by orexin system in arousal, sleep/wakefulness, appetite regulation and their roles in anxiety and stress response, etc., one expects that the drugs (or compounds) targeting orexin system will have beneficial therapeutic effects for the treatments of diseases like sleep disorders including sleep apnea, narcolepsy, insomnia, parasomnia, jet lag syndrome, circadian rhythms disorder, restless leg syndrome, psychiatric, neurological and neurodegenerative disorders including anxiety, depression, manic depression, obsessive compulsive disorders, affective neurosis, depressive neurosis, anxiety neurosis, mood disorder, delirium, panic-attack disorder, posttraumatic stress disorders, sexual dysfunction, schizophrenia, psychosis, cognitive disorders, Alzheimer's and Parkinson's diseases, dementia, mental retardation, dyskinesias such as Huntington's disease and Tourette syndrome, addictions, craving associated with drug abuse, seizure disorders, epilepsy, metabolic diseases such as obesity, diabetes, eating disorders including anorexia and bulimia, asthma, migraine, headache pain, neuropathic pain, sleep disorders associated with psychiatric, neurological and neurodegenerative disorders, neuropathic pain, enhanced or exaggerated sensitivity to pain such as hyperalgesia, causalgia, and allodynia, acute pain, burn pain, back pain, complex regional pain syndrome I and II, arthritic pain, post-stroke pain, post-operative pain, neuralgia, pain associated with HIV infection, post-chemotherapy pain, irritable bowel syndrome, extrapyramidal symptoms induced by antipsychotics and other diseases related to general orexin system dysfunction.

Numerous documents describe the current knowledge on orexin pathway, for example the following documents:

Expert Opin. Ther. Patents (2006), 16(5), 631-646
Current Opinion in Drug Discovery & Development, 2006, 9(5), 551-559
J. Neurosci (2000), 20(20), 7760-7765
Neurosci Lett, (2003), 341(3), 256-258

SUMMARY OF THE INVENTION

The present invention provides compounds of formula

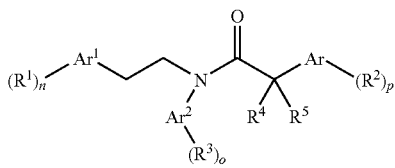

I wherein
i) $Ar^1$ is heteroaryl;
   $Ar^2$ is phenyl and
   Ar is phenyl or heteroaryl; or
ii) $Ar^1$ is phenyl;
   $Ar^2$ is heteroaryl and
   Ar is phenyl or heteroaryl; or
iii) $Ar^1$ is heteroaryl;
   $Ar^2$ is heteroaryl and
   Ar is phenyl or heteroaryl;
$R^1$ is hydrogen, halogen, lower alkyl, lower alkyl substituted by halogen or lower alkoxy;
$R^2$ is hydrogen, halogen, lower alkyl, lower alkyl substituted by halogen, lower alkoxy or lower alkoxy substituted by halogen;
each $R^3$ is, independently selected from hydrogen, halogen, lower alkyl, lower alkyl substituted by halogen, lower alkyl substituted by hydroxy, lower alkyl substituted by cycloalkyl, C(O)O-lower alkyl, C(O)NH-lower alkyl, —$(CH_2)_m$—O-lower alkyl, lower alkoxy, lower alkoxy substituted by halogen, cyano, $SO_2$-lower alkyl, and cycloalkyl,
or where $Ar^2$ is phenyl and o is 2, $R^3$ is optionally $R^3$ and $R^{3'}$ which together with the corresponding carbon atoms to which they are attached optionally form a non aromatic ring containing the groups —$(CH_2)_4$—, —$(CH_2)_3$—, —$CH_2$—$S(O)_2$—$CH_2$—, —$N(CH_3)$—$C(O)$—$N(CH_3)$—, —$(CH_2)_2$—O—, —O—$(CH_2)_2$—O—, —O—$(CH_2)_2$—CH(OH)—, —O—$(CH_2)_2$—, —O—$(CH_2)_3$—, —O—$CH_2$—$C(O)$—$N(CH_3)$—, —$N(CH_3)$—$C(O)$—$(CH_2)_2$—, or —O—$C(CH_3)_2$—O—;
$R^4$ and $R^5$ are each independently hydrogen, hydroxy, lower alkyl, lower alkoxy, $CH_2NH_2$, O—C(O)-lower alkyl, or —NRR' or $R^4$ and $R^5$ together are =O;
R and R' are each independently hydrogen, —$S(O)_2$-lower alkyl, cycloalkyl, —$(CH_2)_m$—OH, —$(CH_2)_m$—O-lower alkyl, —$C(O)CH(NH_2)$-phenyl, or oxetan-3-yl optionally substituted by $CH_2NH_2$, or
R and R' together with the N atom to which they are attached form a heterocycloalkyl ring, optionally containing in addition to the N atom a further heteroatom selected from the group consisting of N, S and O;
n is 1, 2 or 3;
o is 1, 2 or 3;
p is 1, 2 or 3; and
m is 0, 1 or 2;
and pharmaceutically suitable acid addition salts, optically pure enantiomers, racemates and diastereomeric mixtures thereof.

The invention also provides pharmaceutical compositions containing compounds of formula I. The invention further provides processes for the manufacture of the compounds and compositions of the invention.

Compounds of formula I are orexin receptor antagonists and the related compounds may be useful in the treatment of disorders, in which orexin pathways are involved like sleep disorders including sleep apnea, narcolepsy, insomnia, parasomnia, jet lag syndrome, circadian rhythms disorder, restless leg syndrome, psychiatric, neurological and neurodegenerative disorders including anxiety, depression, manic depression, obsessive compulsive disorders, affective neurosis, depressive neurosis, anxiety neurosis, mood disorder, delirium, panic-attack disorder, posttraumatic stress disorders, sexual dysfunction, schizophrenia, psychosis, cognitive disorders, Alzheimer's and Parkinson's diseases, dementia, mental retardation, dyskinesias such as Huntington's disease and Tourette syndrome, addictions, craving associated with drug abuse, seizure disorders, epilepsy, metabolic diseases such as obesity, diabetes, eating disorders including anorexia and bulimia, asthma, migraine, headache pain, neuropathic pain, sleep disorders associated with psychiatric, neurological and neurodegenerative disorders, neuropathic pain, enhanced or exaggerated sensitivity to pain such as hyperalgesia, causalgia, and allodynia, acute pain, burn pain, back pain, complex regional pain syndrome I and II, arthritic pain, post-stroke pain, post-operative pain, neuralgia, pain associated with HIV infection, post-chemotherapy pain, irritable bowel syndrome, extrapyramidal symptoms induced by antipsychotics and other diseases related to general orexin system dysfunction.

The compounds of formula I are novel.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

The term "alkyl" denotes a straight- or branched-chain hydrocarbon group containing from 1-7 carbon atoms. As used herein, the term "lower alkyl" denotes a straight- or branched-chain alkyl group containing from 1-4 carbon atoms, for example, methyl, ethyl, propyl, isopropyl, n-butyl, i-butyl, t-butyl and the like.

The term "halogen" denotes chlorine, iodine, fluorine and bromine.

As used herein, the term "lower alkyl substituted by halogen" denotes a lower alkyl group as defined above, wherein at least one hydrogen atom is replaced by halogen, for example $CF_3$, $CHF_2$, $CH_2F$, $CH_2CF_3$, $CH_2CH_2CF_3$, $CH_2CF_2CF_3$ and the like. Preferred lower alkyl substituted by halogen are lower alkyl substituted by fluoro.

As used herein, the term "lower alkyl substituted by hydroxy" denotes a lower alkyl group as defined above, wherein at least one hydrogen atom is replaced by hydroxy, for example $CH_2OH$ or $CH_2CH_2OH$.

The term "lower alkoxy" denotes a lower alkyl group as defined above, which is attached via an oxygen atom.

As used herein, the term "lower alkoxy substituted by halogen" denotes a lower alkoxy group as defined above, wherein at least one hydrogen atom is replaced by a halogen residue, such as $OCF_3$, $OCHF_2$, $OCH_2F$, $OCH_2CF_3$, $OCH_2CH_2CF_3$, $OCH_2CF_2CF_3$ and the like. Preferred lower alkoxy substituted by halogen are lower alkoxy substituted by fluoro.

The term "cycloalkyl" denotes a saturated carbocyclic group, containing 3-6 carbon atoms.

As used herein, the term "lower alkyl substituted by cycloalkyl" denotes a lower alkyl group as defined above, wherein one hydrogen atom is replaced by a cycloalkyl group, for example $CH_2$-cyclopropyl, $CH_2$-cyclobutyl, $CH_2$-cyclopentyl or $CH_2$-cyclohexyl.

The term "aryl" means the monovalent cyclic aromatic hydrocarbon group consisting of one or more fused rings in which at least one ring is aromatic in nature. Examples of aryl radicals include, but are not limited to, phenyl, naphthyl, 5,6,7,8-tetrahydro-naphthalenyl, biphenyl, indanyl, anthraquinolyl, and the like. A preferred aryl group is phenyl.

"Heteroaryl" means a cyclic group having one or more rings, wherein at least one ring is aromatic in nature, incorporating one, two, or three heteroatoms within the ring (chosen from nitrogen, oxygen, and sulfur). Examples of heteroaryl radicals include, but are not limited to, imidazolyl, oxazolyl, isoxazolyl, thiazolyl, thiophenyl, furanyl, pyrazolyl, pyridinyl, pyrazinyl, pyrimidinyl, pyridazinyl, quinolinyl, isoquinolinyl, benzofuryl, benzothiophenyl, benzothiopyranyl, benzimidazolyl, benzooxazolyl, benzothiazolyl, benzopyranyl, indazolyl, indolyl, isoindolyl, chromanyl, naphtyridinyl, 2,3-dihydro-benzofuranyl, 3,4-dihydro-2H-benzo[b][1.4]dioxepinyl, 3,4-dihydro-2H-benzo[1.4]oxazinyl, indanyl, benzo[1.3]dioxol, 2,3-dihydro-benzo[1.4]dioxinyl, and the like.

"Heterocycloalkyl" means a monovalent saturated moiety, consisting of one, two or three rings, incorporating one, two, or three heteroatoms (chosen from nitrogen, oxygen and sulfur). Heterocycloalkyl can optionally be substituted with one, two, three or four substituents, wherein each substituent is independently hydroxy, alkyl, alkoxy, thioalkyl, halo, haloalkyl, hydroxyalkyl, alkoxycarbonyl, amino, alkylamino, dialkylamino, aminocarbonyl, or carbonylamino, unless otherwise specifically indicated. Examples of heterocyclic moieties include, but are not limited to, optionally substituted tetrahydro-furanyl, optionally substituted piperidinyl, optionally substituted pyrrolidinyl, optionally substituted morpholinyl, optionally substituted piperazinyl, and the like or those which are specifically exemplified herein.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

"Therapeutically effective amount" means an amount that is effective to prevent, alleviate or ameliorate symptoms of disease or prolong the survival of the subject being treated.

The following structures of formulas IA, IB and IC are encompassed by formula I. The invention provides a compound of formula IA:

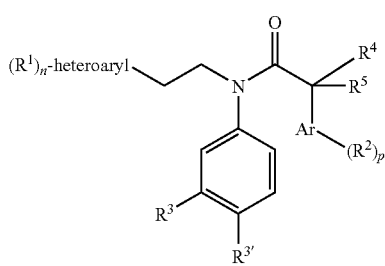

IA wherein
Ar is phenyl or heteroaryl;
$R^1$ is hydrogen, halogen, lower alkyl, lower alkyl substituted by halogen or lower alkoxy;
$R^2$ is hydrogen, halogen, lower alkyl, lower alkyl substituted by halogen, lower alkoxy or lower alkoxy substituted by halogen;
$R^3$ and $R^{3'}$ are independently independently hydrogen, halogen, lower alkyl, lower alkyl substituted by halogen, lower alkyl substituted by hydroxy, lower alkyl substituted by cycloalkyl, C(O)O-lower alkyl, C(O)NH-lower alkyl, —$(CH_2)_m$—O-lower alkyl, lower alkoxy, lower alkoxy substituted by halogen, cyano, $SO_2$-lower alkyl, or cycloalkyl,
or $R^3$ and $R^{3'}$ together with the corresponding carbon atoms to which they are attached form a non aromatic ring containing the groups —$(CH_2)_4$—, —$(CH_2)_3$—, —$CH_2$—$S(O)_2$—$CH_2$—, —$N(CH_3)$—$C(O)$—$N(CH_3)$—, —$(CH_2)_2$—O—, —O—$(CH_2)_2$—O—, —O—$(CH_2)_2$—CH(OH)—, —O—$(CH_2)_2$—, —O—$(CH_2)_3$—, —O—$CH_2$—$C(O)$—$N(CH_3)$—, —$N(CH_3)$—$C(O)$—$(CH_2)_2$—, or —O—$C(CH_3)_2$—O—;
$R^4$ and $R^5$ are each independently hydrogen, hydroxy, lower alkyl, lower alkoxy, $CH_2NH_2$, O—C(O)-lower alkyl, or —NRR' or $R^4$ and $R^5$ together are =O;
R and R' are each independently hydrogen, —$S(O)_2$-lower alkyl, cycloalkyl, —$(CH_2)_m$—OH, —$(CH_2)_m$—O-lower alkyl, —$C(O)CH(NH_2)$-phenyl, or oxetan-3-yl optionally substituted by $CH_2NH_2$, or
R and R' together with the N atom to which they are attached form a heterocycloalkyl ring, optionally containing in addition to the N atom a further heteroatom selected from the group consisting of N, S and O;
n is 1, 2 or 3;
p is 1, 2 or 3; and
m is 0, 1 or 2;
and pharmaceutically suitable acid addition salts, optically pure enantiomers, racemates and diastereomeric mixtures thereof, The invention provides a compound of formula IB

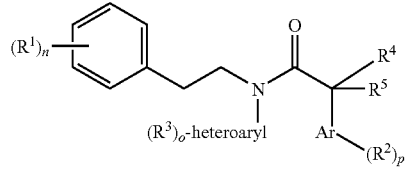

IB wherein
Ar is phenyl or heteroaryl;
$R^1$ is hydrogen, lower alkyl or lower alkyl substituted by halogen;
$R^2$ is hydrogen, halogen or lower alkoxy;
each $R^3$ is independently hydrogen, halogen, lower alkyl, lower alkyl substituted by halogen, lower alkyl substituted by hydroxy, lower alkyl substituted by cycloalkyl, C(O)O-lower alkyl, C(O)NH-lower alkyl, —$(CH_2)_m$-O-lower alkyl, lower alkoxy, lower alkoxy substituted by halogen, cyano, $SO_2$-lower alkyl or cycloalkyl;
$R^4$ and $R^5$ are each independently hydrogen, hydroxy, or —NRR' or $R^4$ and $R^5$ together are =O;
R and R' are each independently hydrogen, —$S(O)_2$-lower alkyl, cycloalkyl, —$(CH_2)_m$—OH, —$(CH_2)_m$—O-lower alkyl, —$C(O)CH(NH_2)$-phenyl, or oxetan-3-yl optionally substituted by $CH_2NH_2$, or R and R' together with the N atom to which they are attached form a heterocycloalkyl ring, optionally containing in addition to the N atom a further heteroatom, selected from the group consisting of N, S and O;
n is 1, 2 or 3;
o is 1, 2 or 3;
p is 1, 2 or 3; and
m is 0, 1 or 2;
and pharmaceutically suitable acid addition salts, optically pure enantiomers, racemates or diastereomeric mixtures thereof.

The invention provides a compound of formula IC

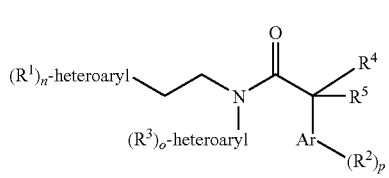

IC wherein
Ar is phenyl or heteroaryl;
$R^1$ is hydrogen, halogen, lower alkyl, lower alkyl substituted by halogen or lower alkoxy;
$R^2$ is hydrogen, halogen, lower alkyl, lower alkyl substituted by halogen, lower alkoxy or lower alkoxy substituted by halogen;
each $R^3$ is independently hydrogen, halogen, lower alkyl, lower alkyl substituted by halogen, lower alkyl substituted by hydroxy, lower alkyl substituted by cycloalkyl, C(O)O-lower alkyl, C(O)NH-lower alkyl, —(CH$_2$)$_m$—O-lower alkyl, lower alkoxy, lower alkoxy substituted by halogen, cyano, SO$_2$-lower alkyl or cycloalkyl;
$R^4$ and $R^5$ are each independently hydrogen, hydroxy, lower alkyl, lower alkoxy, CH$_2$NH$_2$, O—C(O)-lower alkyl, or —NRR' or $R^4$ and $R^5$ together are =O;
R and R' are each independently hydrogen, —S(O)$_2$-lower alkyl, cycloalkyl, —(CH$_2$)$_m$—OH, —(CH$_2$)$_m$—O-lower alkyl, —C(O)CH(NH$_2$)-phenyl, or oxetan-3-yl optionally substituted by CH$_2$NH$_2$, or
R and R' together with the N atom to which they are attached form a heterocycloalkyl ring, optionally containing in addition to the N atom a further heteroatom, selected from the group consisting of N, S and O;
n is 1, 2 or 3;
o is 1, 2 or 3;
p is 1, 2 or 3; and
m is 0, 1 or 2;
and pharmaceutically suitable acid addition salts, optically pure enantiomers, racemates or diastereomeric mixtures thereof.

Preferred compounds as defined above are those, wherein $R^1$ is hydrogen, halogen, lower alkyl or lower alkyl substituted by fluoro, more preferably wherein $R^1$ is methyl, trifluoromethyl, fluoro or chloro.

Other preferred compounds are those, wherein $R^2$ is hydrogen, halogen or lower alkoxy, more preferably wherein $R^2$ is hydrogen, fluoro or chloro.

In a preferred embodiment of the present invention, $R^3$ is hydrogen, halogen, cyano, lower alkyl, lower alkyl substituted by fluoro, lower alkyl substituted by hydroxy, lower alkoxy, lower alkoxy substituted by fluoro, C(O)O-lower alkyl, C(O)NH-lower alkyl or cycloalkyl. More preferably, $R^3$ is hydrogen, halogen, lower alkyl, lower alkyl substituted by hydroxy, lower alkoxy, lower alkoxy substituted by fluoro or C(O)O-lower alkyl. Even more preferably, $R^3$ is hydrogen, methyl, methoxy, fluoro, chloro, hydroxymethyl, difluoromethoxy or C(O)OCH$_3$.

Still other preferred compounds are those, wherein $R^4$ is hydrogen or lower alkyl, particularly wherein $R^4$ is hydrogen or methyl.

Preferably, $R^5$ is hydrogen, NH$_2$, hydroxy, lower alkyl, NHC(O)CH(NH$_2$)-phenyl, NH(oxetan-3-yl), NH(3-(CH$_2$NH$_2$)-oxetan-3-yl)$_2$, NH—SO$_2$-lower alkyl, NH-cycloalkyl, OC(O)-lower alkyl or CH$_2$NH$_2$. More preferably, $R^5$ is hydrogen, NH$_2$, hydroxy, CH$_3$, NHC(O)CH(NH$_2$)-phenyl, NH(oxetan-3-yl), NH(3-(CH$_2$NH$_2$)-oxetan-3-yl) or OC(O)—CH$_3$. Furthermore, it is preferred that $R^4$ and $R^5$ together are =O.

Where $Ar^1$ is heteroaryl, said heteroaryl preferably is pyridinyl, thiazolyl, thienyl or isoxazolyl. More preferably, said heteroaryl is pyridine-2-yl, pyridine-3-yl, thiazol-2-yl or isoxazol-5-yl.

If $Ar^2$ is heteroaryl, said heteroaryl preferably is pyridinyl, thiazolyl, benzothiazolyl, pyrazolyl, indazolyl, quinolinyl, benzooxazolyl or indolyl. More preferably, said heteroaryl is pyridine-3-yl, thiazol-5-yl, pyrazol-3-yl, indazol-5-yl, quinolin-3-yl or indol-3-yl.

If Ar is heteroaryl, said heteroaryl preferably is pyridinyl or benzoimidazolyl. In another preferred embodiment, Ar is phenyl.

Moreover, n preferably is 1. In addition, p preferably is 1. Furthermore, o preferably is 1 or 2.

Preferred compounds of formula IA are the following:
(S)-2-amino-N-(3,4-dimethyl-phenyl)-2-phenyl-N-[2-(6-trifluoromethyl-pyridin-3-yl)-ethyl]-acetamide;
(S)—N-(3,4-dimethyl-phenyl)-2-hydroxy-2-phenyl-N-[2-(6-trifluoromethyl-pyridin-3-yl)-ethyl]-acetamide;
(R)—N-(3,4-dimethyl-phenyl)-2-hydroxy-2-phenyl-N-[2-(6-trifluoromethyl-pyridin-3-yl)-ethyl]-acetamide;
(S)-2-((S)-2-amino-2-phenyl-acetylamino)-N-(3,4-dimethoxy-phenyl)-2-phenyl-N-[2(6-trifluoromethyl-pyridin-3-yl)-ethyl]-acetamide;
(S)-2-amino-N-(3,4-dimethoxy-phenyl)-2-phenyl-N-[2-(6-trifluoromethyl-pyridin-3-yl)-ethyl]-acetamide;
(S)—N-(3,4-dimethyl-phenyl)-2-(4-fluoro-phenyl)-2-hydroxy-N-[2-(6-trifluoromethyl-pyridin-3-yl)-ethyl]-acetamide;
(S)-2-(3-aminomethyl-oxetan-3-ylamino)-N-(3,4-dimethyl-phenyl)-2-phenyl-N-[2-(6-trifluoromethyl-pyridin-3-yl)-ethyl]acetamide;
(S)-2-amino-2-phenyl-N-(5,6,7,8-tetrahydro-naphthalen-2-yl)-N-[2-(6-trifluoromethyl-pyridin-3-yl)-ethyl]-acetamide;
(S)-2-amino-N-(3,4-dimethyl-phenyl)-2-(4-fluoro-phenyl)-N-[2-(6-trifluoromethyl-pyridin-3-yl)-ethyl]-acetamide;
(S)-2-hydroxy-2-phenyl-N-(5,6,7,8-tetrahydro-naphthalen-2-yl)-N-[2-6-trifluoromethyl-pyridin-3-yl)-ethyl]-acetamide;
(S)-2-hydroxy-2-phenyl-N-p-tolyl-N-[2-(6-trifluoromethyl-pyridin-3-yl)-ethyl]-acetamide;
N-(3,4-dimethyl-phenyl)-2-phenyl-N-[2-(6-trifluoromethyl-pyridin-3-yl)-ethyl]-acetamide;
(S)-2-hydroxy-N-(3-methoxy-4-methyl-phenyl)-2-phenyl-N-[2-(6-trifluoromethyl-pyridin-3-yl)-ethyl]-acetamide;
N-(3,4-dimethyl-phenyl)-2-oxo-2-phenyl-N-[2-(6-trifluoromethyl-pyridin-3-yl)-ethyl]-acetamide;
(S)-2-amino-N-(3,4-dimethyl-phenyl)-N-[2-(5-methyl-pyridin-2-yl)-ethyl]-2-phenyl-acetamide;
(S)—N-(3,4-dimethyl-phenyl)-2-phenyl-N-[2-(6-trifluoromethyl-pyridin-3-yl)-ethyl]-propionamide;

(S)-2-amino-N-(3,4-dimethyl-phenyl)-2-phenyl-N-[2-(5-trifluoromethyl-pyridin-2-yl)-ethyl]-acetamide;
(S)—N-(3,4-dimethyl-phenyl)-2-hydroxy-2-phenyl-N-[2-(5-trifluoromethyl-pyridin-2-yl)-ethyl]-acetamide;
(R,S)—N-(3,4-dimethyl-phenyl)-2-hydroxy-2-phenyl-N-[2-(6-trifluoromethyl-pyridin-3-yl)-ethyl]-propionamide;
(S)—N-(2,3-dihydro-benzo[1,4]dioxin-6-yl)-2-hydroxy-2-phenyl-N-[2-(6-trifluoromethyl-pyridin-3-yl)-ethyl]-acetamide;
(S)-2-hydroxy-N-(3-methoxy-phenyl)-2-phenyl-N-[2-(6-trifluoromethyl-pyridin-3-yl)-ethyl]-acetamide;
(S)—N-(3,4-dimethyl-phenyl)-2-(oxetan-3-ylamino)-2-phenyl-N-[2-(6-trifluoromethyl-pyridin-3-yl)-ethyl]-acetamide;
(S)-2-hydroxy-N-(3-methoxy-phenyl)-2-phenyl-N-[2-(6-trifluoromethyl-pyridin-3-yl)-ethyl]-acetamide;
(S)-2-(4-fluoro-phenyl)-2-hydroxy-N-(5,6,7,8-tetrahydro-naphthalen-2-yl)-N-[2-(6-trifluoromethyl-pyridin-3-yl)-ethyl]-acetamide;
(S)-2-(4-fluoro-phenyl)-2-hydroxy-N-(3-methoxy-4-methyl-phenyl)-N-[2-(6-trifluoromethyl-pyridin-3-yl)-ethyl]-acetamide;
(S)-2-(4-fluoro-phenyl)-2-hydroxy-N-(3-methoxy-4-methyl-phenyl)-N-[2-(6-trifluoromethyl-pyridin-3-yl)-ethyl]-acetamide;
(S)-2-hydroxy-N—((S)-4-hydroxy-chroman-6-yl)-2-phenyl-N-[2-(6-trifluoromethyl-pyridin-3-yl)-ethyl]-acetamide;
acetic acid (S)-{(3,4-dimethyl-phenyl)-[2-(5-trifluoromethyl-pyridin-2-yl)-ethyl]-carbamoyl}-phenyl-methyl ester;
(S)—N-[2-(5-chloro-pyridin-2-yl)-ethyl]-N-(3,4-dimethyl-phenyl)-2-hydroxy-2-phenyl-acetamide;
(S)-2-amino-N-(3,4-dimethyl-phenyl)-N-[2-(4-methyl-thiazol-2-yl)-ethyl]-2-phenyl-acetamide;
(S)—N-(3,4-dimethyl-phenyl)-N-[2-(5-fluoro-pyridin-2-yl)-ethyl]-2-hydroxy-2-phenyl-acetamide;
(S)—N-(3,4-dimethyl-phenyl)-2-hydroxy-N-[2-(3-methyl-isoxazol-5-yl)-ethyl]-2-phenyl-acetamide;
(R,S)-2-(4-fluoro-phenyl)-2-hydroxy-N-indan-5-yl-N-[2-(5-trifluoromethyl-pyridin-2-yl)-ethyl]-acetamide;
(R,S)—N-(2,3-dihydro-benzofuran-5-yl)-2-(4-fluoro-phenyl)-2-hydroxy-N-[2-(5-trifluoromethyl-pyridin-2-yl)-ethyl]-acetamide;
(R,S)-2-(4-fluoro-phenyl)-2-hydroxy-N-(3-methoxy-phenyl)-N-[2-(5-trifluoromethyl-pyridin-2-yl)-ethyl]-acetamide;
(R,S)—N-(4-fluoro-3-methyl-phenyl)-2-(4-fluoro-phenyl)-2-hydroxy-N-[2-(5-trifluoromethyl-pyridin-2-yl)-ethyl]-acetamide;
(R,S)—N-(3-fluoro-4-methyl-phenyl)-2-(4-fluoro-phenyl)-2-hydroxy-N-[2-(5-trifluoromethyl-pyridin-2-yl)-ethyl]-acetamide;
(R,S)—N-(4-chloro-3-methoxy-phenyl)-2-(4-fluoro-phenyl)-2-hydroxy-N-[2-(5-trifluoromethyl-pyridin-2-yl)-ethyl]-acetamide;
(S)—N-(3-fluoro-4-methyl-phenyl)-2-(4-fluoro-phenyl)-2-hydroxy-N-[2-(5-trifluoromethyl-pyridin-2-yl)-ethyl]-acetamide;
(S)—N-(4-fluoro-3-methyl-phenyl)-2-(4-fluoro-phenyl)-2-hydroxy-N-[2-(5-trifluoromethyl-pyridin-2-yl)-ethyl]-acetamide;
(S)-2-(4-fluoro-phenyl)-2-hydroxy-N-indan-5-yl-N-[2-(5-trifluoromethyl-pyridin-2-yl)-ethyl]-acetamide;
(S)—N-(2,3-dihydro-benzofuran-5-yl)-2-(4-fluoro-phenyl)-2-hydroxy-N-[2-(5-trifluoromethyl-pyridin-2-yl)-ethyl]-acetamide;
(R,S)—N-(4-fluoro-3-methoxy-phenyl)-2-(4-fluoro-phenyl)-2-hydroxy-N-[2-(5-trifluoromethyl-pyridin-2-yl)-ethyl]-acetamide;
(R,S)—N-(4-fluoro-3-hydroxymethyl-phenyl)-2-(4-fluoro-phenyl)-2-hydroxy-N-[2-(5-trifluoromethyl-pyridin-2-yl)-ethyl]-acetamide;
(S)—N-(4-fluoro-3-methoxy-phenyl)-2-(4-fluoro-phenyl)-2-hydroxy-N-[2-(5-trifluoromethyl-pyridin-2-yl)-ethyl]-acetamide;
(R,S)-2-(4-fluoro-phenyl)-2-hydroxy-N-(4-methoxy-3-methyl-phenyl)-N-[2-(5-trifluoromethyl-pyridin-2-yl)-ethyl]-acetamide;
(R,S)—N-(3-difluoromethoxy-4-methyl-phenyl)-2-(4-fluoro-phenyl)-2-hydroxy-N-[2-(5-trifluoromethyl-pyridin-2-yl)-ethyl]-acetamide;
(R,S)—N-(3,4-bis-difluoromethoxy-phenyl)-2-(4-fluoro-phenyl)-2-hydroxy-N-[2-(5-trifluoromethyl-pyridin-2-yl)-ethyl]-acetamide;
(R,S)—N-(4-chloro-3-ethyl-phenyl)-2-(4-fluoro-phenyl)-2-hydroxy-N-[2-(5-trifluoromethyl-pyridin-2-yl)-ethyl]-acetamide;
(R,S)—N-(4-chloro-3-hydroxymethyl-phenyl)-2-(4-fluoro-phenyl)-2-hydroxy-N-[2-(5-trifluoromethyl-pyridin-2-yl)-ethyl]-acetamide;
(R,S)-2-chloro-5-{[2-(4-fluoro-phenyl)-2-hydroxy-acetyl]-[2-(5-trifluoromethyl-pyridin-2-yl)-ethyl]-amino}-benzoic acid methyl ester;
(S)-2-(4-fluoro-phenyl)-2-hydroxy-N—((R or S)-4-hydroxy-chroman-6-yl)-N-[2-(6-trifluoromethyl-pyridin-3-yl)-ethyl]-acetamide;
(S)-2-(4-fluoro-phenyl)-2-hydroxy-N—((S or R)-4-hydroxy-chroman-6-yl)-N-[2-(6-trifluoromethyl-pyridin-3-yl)-ethyl]-acetamide; and
(R,S)—N-(4-chloro-3-cyclopropoxy-phenyl)-2-(4-fluoro-phenyl)-2-hydroxy-N-[2-(5-trifluoromethyl-pyridin-2-yl)-ethyl]-acetamide.

Preferred compounds of formula IB are the following:
(R,S)-2-amino-2-(4-chloro-phenyl)-N-(2,4-dimethyl-thiazol-5-yl)-N-(2-p-tolyl-ethyl)-acetamide;
(R,S)-2-amino-N-(6-methoxy-pyridin-3-yl)-2-phenyl-N-[2-(4-trifluoromethyl-phenyl)-ethyl]-acetamide;
(R,S)-2-amino-2-(4-chloro-phenyl)-N-(2,5-dimethyl-2H-pyrazol-3-yl)-N-[2-(4-trifluoromethyl-phenyl)-ethyl]-acetamide; and
(R,S)—N-(2,5-dimethyl-2H-pyrazol-3-yl)-2-hydroxy-2-phenyl-N-[2-(4-trifluoromethyl-phenyl)-ethyl]-acetamide.

Preferred compounds of formula IC are the following:
(S)—N-(1-ethyl-3-methyl-1H-indazol-5-yl)-2-hydroxy-2-phenyl-N-[2-(6-trifluoromethyl-pyridin-3-yl)-ethyl]-acetamide;
((S)-2-hydroxy-2-phenyl-N-quinolin-3-yl-N-[2-(6-trifluoromethyl-pyridin-3-yl)-ethyl]-acetamide;
(R,S)-2-(4-fluoro-phenyl)-2-hydroxy-N-(1-methyl-1H-indol-6-yl)-N-[2-(5-trifluoromethyl-pyridin-2-yl)-ethyl]-acetamide;
(S)-2-(4-fluoro-phenyl)-2-hydroxy-N-(3-methyl-1H-indazol-5-yl)-N-[2-(6-trifluoromethyl-pyridin-3-yl)-ethyl]-acetamide; and (S)—N-(1,3-dimethyl-1H-indazol-5-yl)-2-(4-fluoro-phenyl)-2-hydroxy-N-[2-(6-trifluoromethyl-pyridin-3-yl)-ethyl]-acetamide.

The present compounds of formula IA, IB and IC and their pharmaceutically acceptable salts can be prepared by methods known in the art, for example, by processes described below, which process comprises reacting a compound of formula IIA, IIB or IIC The following schemes describe the processes for preparation of compounds of formula IA, IB and IC in more detail.

Preparation of Compounds of Formula IA

In accordance with scheme 1 (the starting materials of formulas IV-IX are known compounds or can be prepared according to methods known in the art), a compound of formula IIA can be prepared as follows:

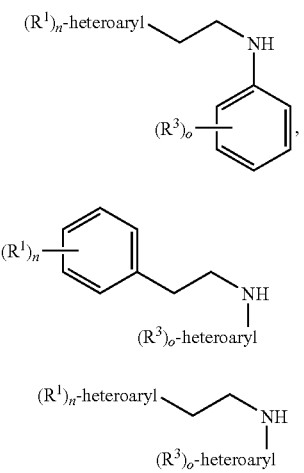

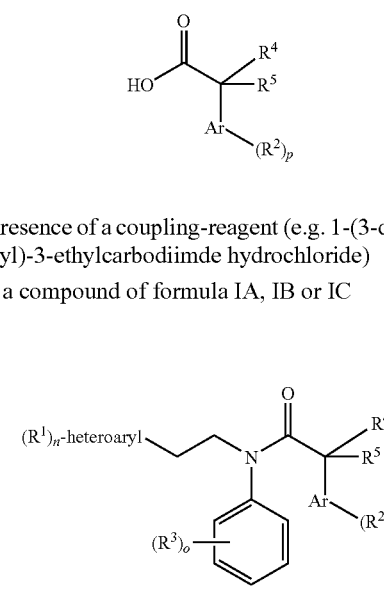

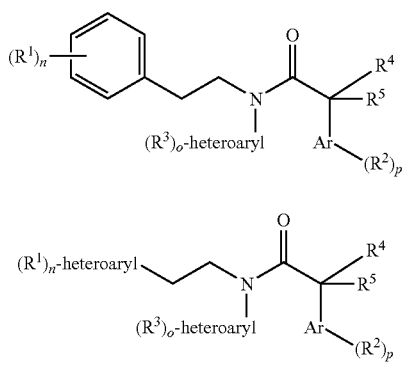

with a compound of formula III in the presence of a coupling-reagent (e.g. 1-(3-dimethylaminopropyl)-3-ethylcarbodiimde hydrochloride) to give a compound of formula IA, IB or IC

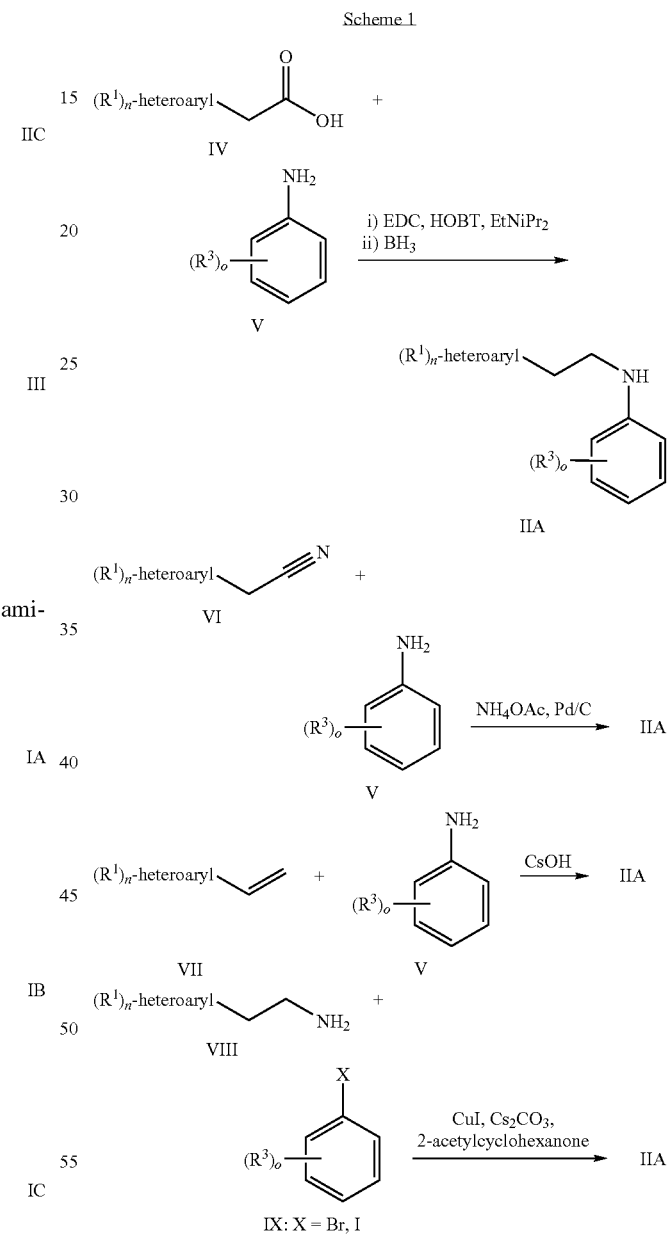

wherein $R^1$-$R^5$, n, o and p m are as described above, and, if desired, converting a compound of formula IA, IB or IC into a pharmaceutically acceptable salt.

Carboxylic acid IV and aniline V are stirred in a suitable solvent, for example dichloromethane, with 1-hydroxybenzotriazole (HOBT) and 1-(3-dimethylaminopropyl)-3-ethylcarbodiimide hydrochloride (EDC) in the presence of a suitable base, for example N,N-diisopropylethylamine, at ambient or elevated temperature. The reaction mixture is then concentrated and heated with borane-tetrahydrofuran complex in a suitable solvent, for example tetrahydrofuran, at elevated temperature to afford IIA. Alternatively, aniline IIA can be obtained by stirring of nitrile VI and aniline V in a suitable solvent, for example methanol, with ammonium acetate and palladium on charcoal at ambient or elevated temperature. Alternatively, heating of aniline V with the vinyl-compound VII in the presence of cesium hydroxide in a suitable solvent, for example N-methylpyrrolidine, affords the desired aniline IIA. Alternatively, IIA can be obtained by heating of amine VII and aryl-halogenide IX in the presence of copper(I) iodide and 2-acetylcyclohexanone in a suitable solvent, for example N,N-dimethylformamide.

Scheme 2

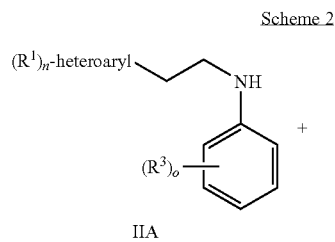

IIA

+

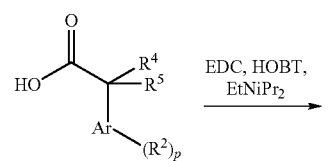

III ($R^4 = R^5 = H$),
III ($R^4 = H, R^5 = CH_3$)

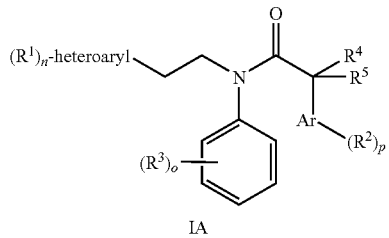

IA

In accordance with scheme 2, a compound of formula IA can be prepared as follows:
Aniline IIA and carboxylic acid III are stirred in a suitable solvent, for example dichloromethane, with 1-hydroxy-benzotriazole (HOBT) and 1-(3-dimethylaminopropyl)-3-ethylcarbodiimide hydrochloride (EDC) in the presence of a suitable base, for example N,N-diisopropylethylamine, at ambient or elevated temperature.

Scheme 3

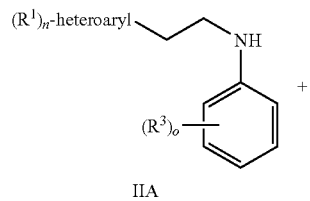

IIA

+

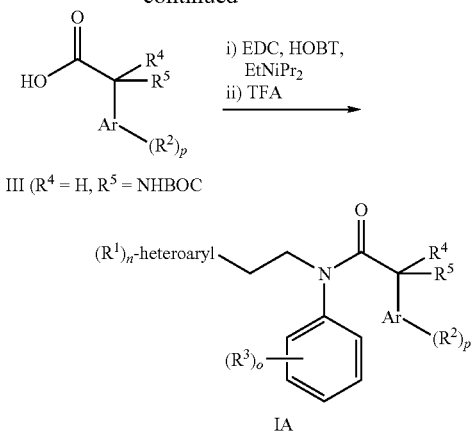

III ($R^4 = H, R^5 = NHBOC$)

In accordance with scheme 3, a compound of formula IA can be prepared as follows:
Aniline IIA and carboxylic acid III are stirred in a suitable solvent, for example dichloromethane, with 1-hydroxy-benzotriazole (HOBT) and 1-(3-dimethylaminopropyl)-3-ethylcarbodiimide hydrochloride (EDC) in the presence of a suitable base, for example N,N-diisopropylethylamine, at ambient or elevated temperature. Final compound IA is obtained by treatment with a suitable acid, for example trifluoroacetic acid (TFA), in a suitable solvent, for example dichloromethane.

Scheme 4

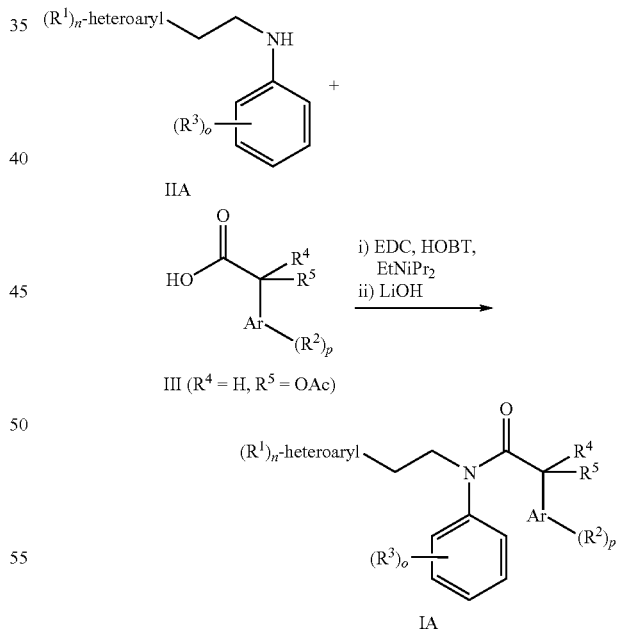

III ($R^4 = H, R^5 = OAc$)

In accordance with scheme 4, a compound of formula IA can be prepared as follows:
Aniline IIA and carboxylic acid III are stirred in a suitable solvent, for example dichloromethane, with 1-hydroxy-benzotriazole (HOBT) and 1-(3-dimethylaminopropyl)-3-ethylcarbodiimide hydrochloride (EDC) in the presence of a suitable base, for example N,N-diisopropylethylamine, at ambient or elevated temperature. Final compound IA is obtained by treatment with lithium hydroxide in a suitable solvent mixture, for example tetrahydrofurane and water, at lowered or ambient temperature.

Scheme 5

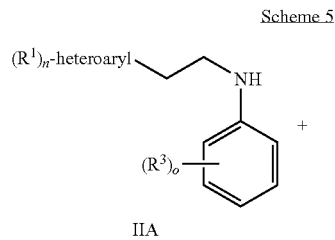

IIA

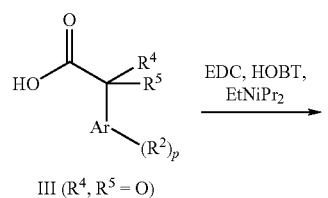

III ($R^4, R^5 = O$)

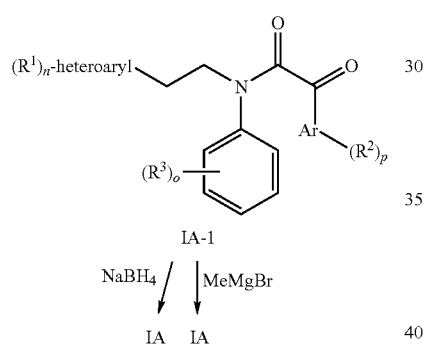

IA-1

NaBH$_4$ / MeMgBr

IA    IA

In accordance with scheme 5, a compound of formula IA can be prepared as follows:

Aniline IIA and carboxylic acid III are stirred in a suitable solvent, for example dichloromethane, with 1-hydroxybenzotriazole (HOBT) and 1-(3-dimethylaminopropyl)-3-ethylcarbodiimide hydrochloride (EDC) in the presence of a suitable base, for example N,N-diisopropylethylamine, at ambient or elevated temperature to afford keto-amide IA-1. Compound IA is obtained by either treatment of IA-1 with sodium borohydride in a suitable solvent, for example methanol, at lowered or ambient temperature or by treatment with a Grignard-reagent like methylmagnesiumbromide in a suitable solvent, for example diethylether, at lowered or ambient temperature.

Scheme 6

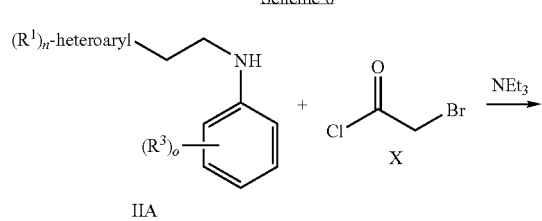

IIA

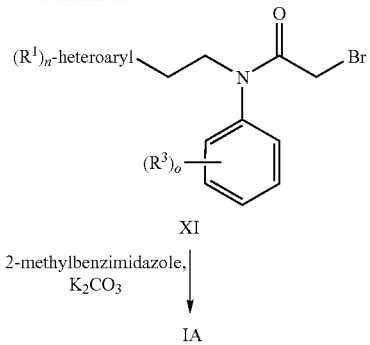

XI 2-methylbenzimidazole, K$_2$CO$_3$

IA

In accordance with scheme 6, a compound of formula IA can be prepared as follows:

Aniline IIA and bromoacetyl chloride X are stirred in a suitable solvent, for example diethylether, in the presence of a suitable base, for example triethylamine, at lowered or ambient temperature to afford compound XI. Final compound IA is obtained by treatment of XI with 2-methylbenzimidazole in the presence of a suitable base, for example potassium carbonate, in a suitable solvent, for example acetonitrile, at elevated temperature.

Scheme 7

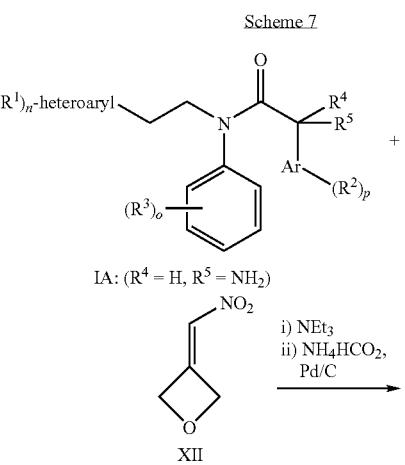

IA: ($R^4 = H, R^5 = NH_2$)

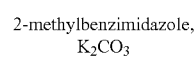

XII i) NEt$_3$
ii) NH$_4$HCO$_2$, Pd/C

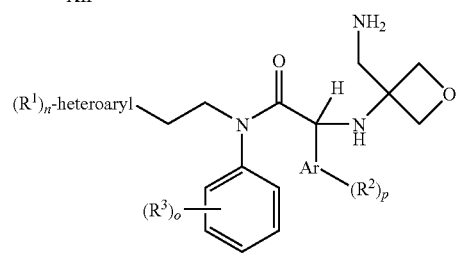

IA-2

In accordance with scheme 7, a compound of formula IA can be prepared as follows:

Amine IA and nitroalkene XII are stirred in a suitable solvent, for example dichloromethane, in the presence of triethylamine at ambient temperature. After concentration and dissolving in a suitable solvent mixture, for example methanol and water, the final compound IA-2 is obtained by treatment with ammonium formate and palladium on charcol at ambient temperature.

Scheme 8

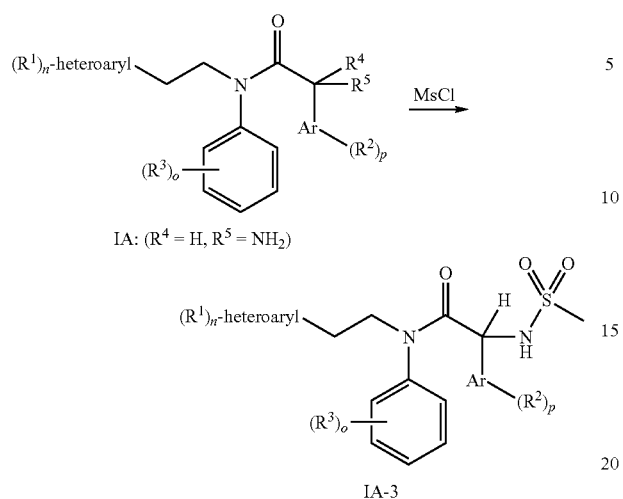

In accordance with scheme 8, a compound of formula IA can be prepared as follows:
Amine IA is stirred in a suitable solvent, for example dichloromethane, with methanesulphonyl chloride at ambient temperature. to obtain final compound IA-3.

Scheme 9

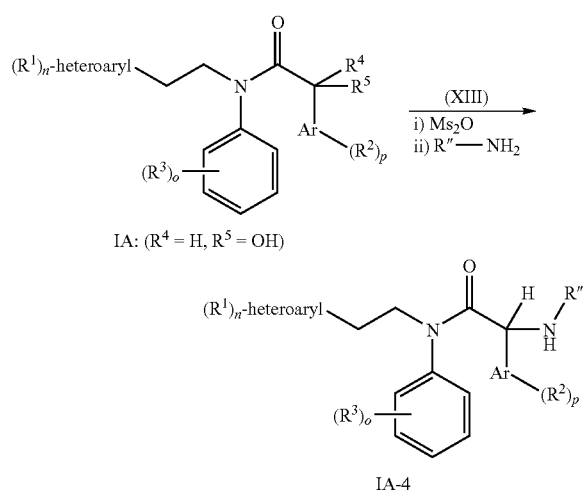

In accordance with scheme 9, a compound of formula IA can be prepared as follows:
Amine IA is stirred in a suitable solvent, for example dichloromethane, with methanesulphonic anhydride at ambient temperature in the presence of triethylamine and 4-N,N-dimethylamino-pyridine to obtain the corresponding mesylate as an intermediate which was treated with amine XIII in the presence of tetrabutylammonium iodide in a suitable solvent, for example N,N-dimethylformamide, at elevated temperature affording IA-4.

Preparation of Compounds of Formula IB

In accordance with scheme 10 (the starting materials of formulas XIV-XVII are known compounds or can be prepared according to methods known in the art), a compound of formula IIA can be prepared as follows:

Scheme 10

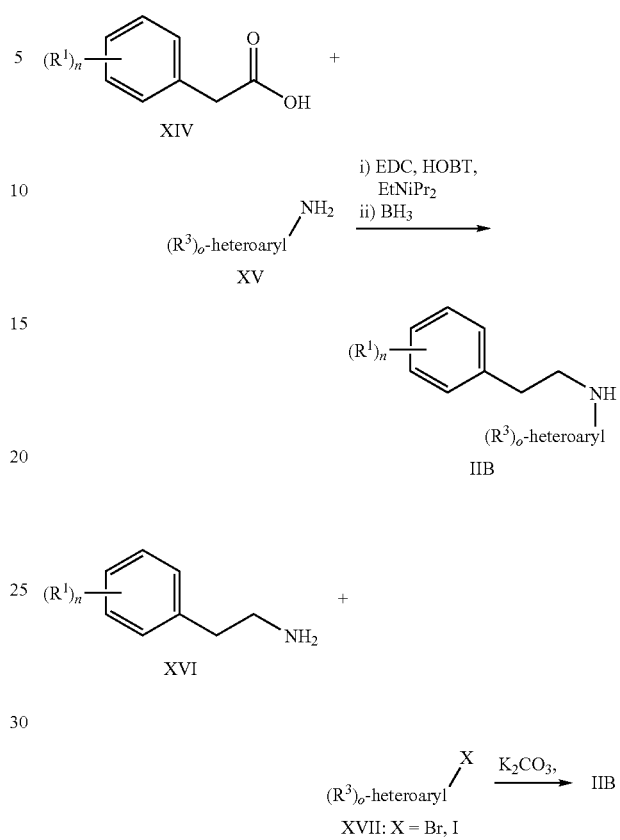

Carboxylic acid XIV and amine XV are stirred in a suitable solvent, for example dichloromethane, with 1-hydroxybenzotriazole (HOBT) and 1-(3-dimethylaminopropyl)-3-ethylcarbodiimide hydrochloride (EDC) in the presence of a suitable base, for example N,N-diisopropylethylamine, at ambient or elevated temperature. The reaction mixture is then concentrated and heated with borane-tetrahydrofuran complex in a suitable solvent, for example tetrahydrofuran, at elevated temperature to afford IIB. Alternatively, IIB can be obtained by heating of amine XII and heteroaryl-halogenide XVII in the presence of a base, for example potassium carbonate, in a suitable solvent, for example dimethylsulfoxid.

Scheme 11

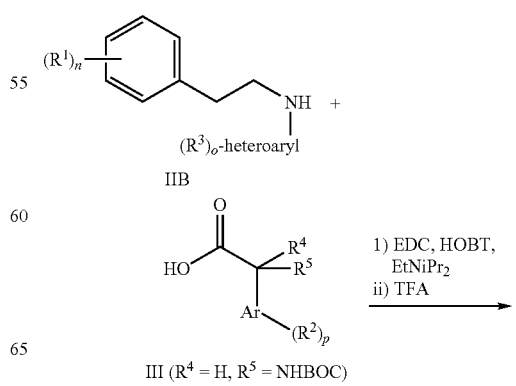

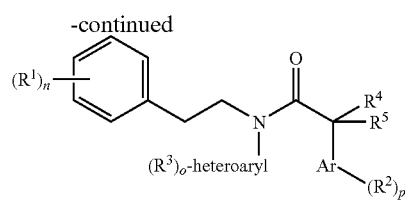

IB

In accordance with scheme 11, a compound of formula IB can be prepared as follows:

Amine IIB and carboxylic acid III are stirred in a suitable solvent, for example dichloromethane, with 1-hydroxybenzotriazole (HOBT) and 1-(3-dimethylaminopropyl)-3-ethylcarbodiimide hydrochloride (EDC) in the presence of a suitable base, for example N,N-diisopropylethylamine, at ambient or elevated temperature. Final compound IB is obtained by treatment with a suitable acid, for example trifluoroacetic acid (TFA), in a suitable solvent, for example dichloromethane.

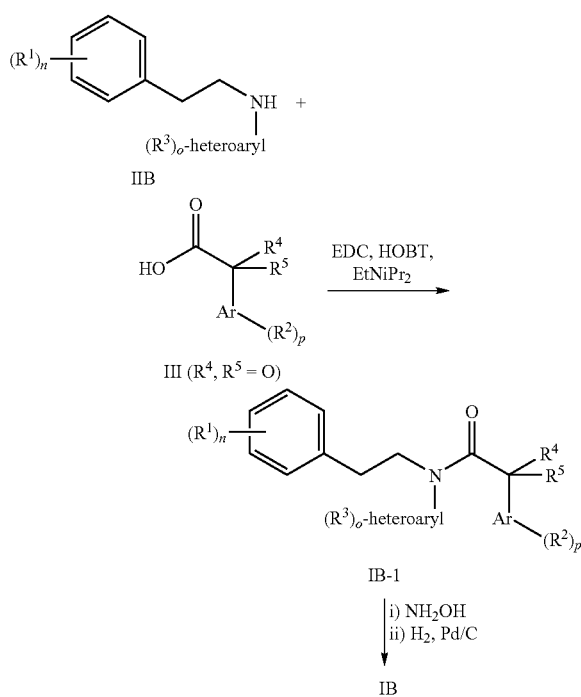

In accordance with scheme 12, a compound of formula IB can be prepared as follows:

Amine IIB and carboxylic acid III are stirred in a suitable solvent, for example dichloromethane, with 1-hydroxybenzotriazole (HOBT) and 1-(3-dimethylaminopropyl)-3-ethylcarbodiimide hydrochloride (EDC) in the presence of a suitable base, for example N,N-diisopropylethylamine, at ambient or elevated temperature to afford keto-amide IB-1. Compound IB is obtained by treatment of IB-1 with hydroxylamine hydrochloride in the presence of a suitable base, for example 2,6-lutidine, a suitable solvent, for example ethanol, at ambient temperature followed by hydrogenation with a suitable catalyst, for example palladium on charcoal, in the presence of a suitable acid, for example trifluoroacetic acid, in a suitable solvent, for example ethanol, at ambient temperature.

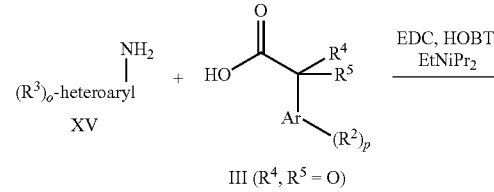

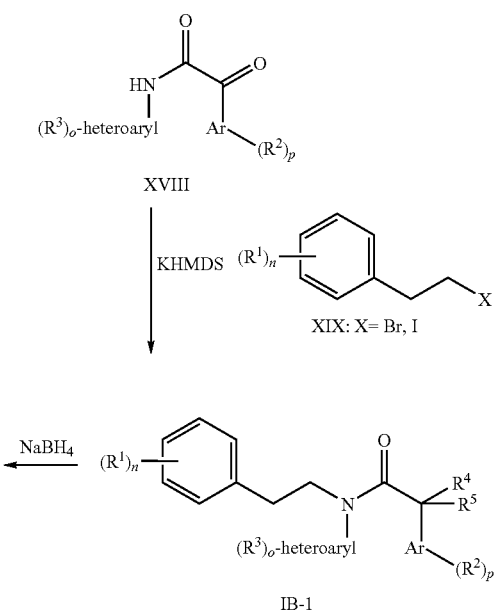

In accordance with scheme 14, a compound of formula IB can be prepared as follows:

Amine XV and carboxylic acid III are stirred in a suitable solvent, for example dichloromethane, with 1-hydroxybenzotriazole (HOBT) and 1-(3-dimethylaminopropyl)-3-ethylcarbodiimide hydrochloride (EDC) in the presence of a suitable base, for example N,N-diisopropylethylamine, at ambient or elevated temperature to afford keto-amide XVIII which is further alkylated by treatment with a suitable base, for example KHMDS, and arylethylamine XIX in a suitable solvent, for example N,N-dimethylformamide, at ambient temperature to obtain keto-amide IB-1. Compound IB is obtained by treatment of IB-1 with sodium borohydride in a suitable solvent, for example methanol, at lowered or ambient temperature.

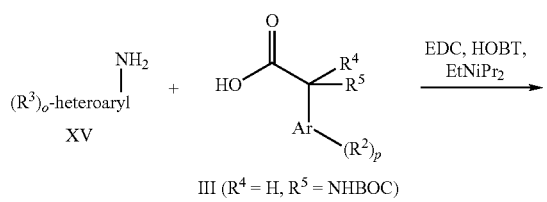

-continued

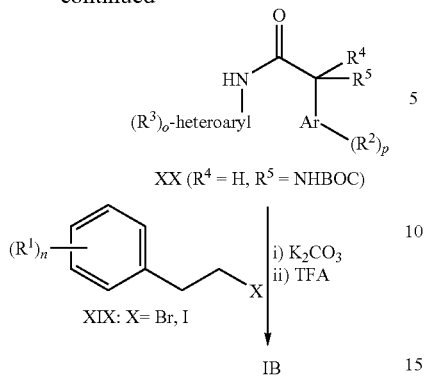

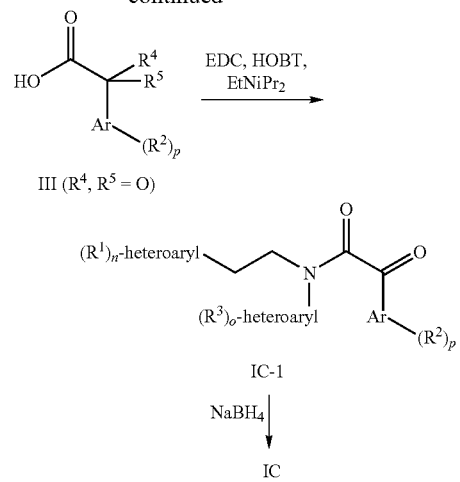

In accordance with scheme 14, a compound of formula IB can be prepared as follows:

Amine XV and carboxylic acid III are stirred in a suitable solvent, for example dichloromethane, with 1-hydroxybenzotriazole (HOBT) and 1-(3-dimethylaminopropyl)-3-ethylcarbodiimide hydrochloride (EDC) in the presence of a suitable base, for example N,N-diisopropylethylamine, at ambient or elevated temperature to afford amide XX which is further alkylated by treatment with a suitable base, for example potassium carbonate, and arylethylamine XIX in a suitable solvent, for example N,N-dimethylformamide, at ambient or elvated temperature followed by deprotection by treatment with a suitable acid, for example trifluoroacetic acid, in a suitable solvent, for example ethyl acetate, at ambient temperature to afford compound IB.

Preparation of Compounds of Formula IC

In accordance with scheme 15 (the starting materials of formulas VI and XV are known compounds or can be prepared according to methods known in the art), a compound of formula IIC can be prepared as follows:

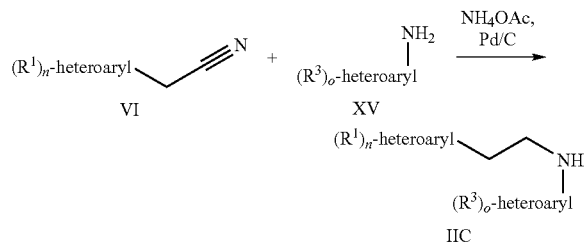

Amine IIC can be obtained by stirring of nitrile VI and amine XV in a suitable solvent, for example methanol, with ammonium acetate and palladium on charcoal at ambient or elevated temperature (according to scheme 15).

Scheme 16

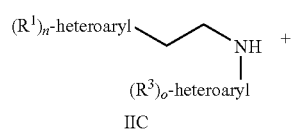

In accordance with scheme 16, a compound of formula IC can be prepared as follows:

Amine IIC and carboxylic acid III are stirred in a suitable solvent, for example dichloromethane, with 1-hydroxybenzotriazole (HOBT) and 1-(3-dimethylaminopropyl)-3-ethylcarbodiimide hydrochloride (EDC) in the presence of a suitable base, for example N,N-diisopropylethylamine, at ambient or elevated temperature to afford keto-amide IC-1. Compound IC is obtained by treatment of IC-1 with sodium borohydride in a suitable solvent, for example methanol, at lowered or ambient temperature.

The compounds were investigated in accordance with the test given hereinafter.

Intracellular $Ca^{2+}$ Mobilization Assay

The Chinese Hamster Ovary (dHFr—) mutant cell line stably expressing human orexin-1 (hOX1) or human orexin-2 (hOX2) receptors were maintained in Dulbecco's Modified Eagle Medium (1X) with GlutaMax™ 1, 4500 mg/L D-Glucose and Sodium Pyruvate (Catalog No. 31966-021, Invitrogen, Carlsbad, Calif.), 5% dialyzed fetal calf serum (Catalog No. 26400-044), 100 μg/ml penicillin and 100 μg/ml streptomycin. The cells were seeded at $5 \times 10^4$ cells/well in the poly-D-lysine treated, 96-well, black/clear-bottomed plates (Catalog No. BD356640, BD Biosciences, Palo Alto, Calif.). 24 h later, the cells were loaded for 1 h at 37° C. with 4 μM Flou-4 acetoxymethyl ester (Catalog No. F-14202, Molecular Probes, Eugene, Oreg.) in FLIPR buffer (1×HBSS, 20 mM HEPES, 2.5 mM Probenecid). Hanks' Balanced Salt Solution (HBSS) (10×) (catalog No. 14065-049) and HEPES (1M) (catalog No. 15630-056) were purchased from Invitrogen, Carlsbad, Calif. Probenecid (250 mM) (catalog No. P8761) was from Sigma, Buchs, Switzerland. The cells were washed five times with FLIPR buffer to remove excess dye and intracellular calcium mobilization, $[Ca^{2+}]_i$ were measured using a Fluorometric Imaging Plate Reader (FLIPR-96, Molecular Devices, Menlo Park, Calif.) as described previously (Malherbe et al., *Mol. Pharmacol.*, 64, 823-832, 2003). Orexin A (catalog No. 1455, Toris Cookson Ltd, Bristol, UK) was used as agonist. Orexin A (50 mM stock solution in DMSO) was diluted in FLIPR buffer +0.1% BSA. The $EC_{50}$ and $EC_{80}$ values of orexin-A were measured daily from standard agonist concentration-response curves in CHO(dHFr—)—OX1R and —OX2R cell lines. All compounds were dissolved in 100% DMSO. Inhibition curves were determined by addition of 11 concentrations (0.0001-10 μM) of inhibitory compounds and using $EC_{80}$ value of orexin-A as agonist (a concentration which gave 80% of max agonist response, determined daily). The antagonists were applied 25 min (incubation at 37° C.) before the application of the agonist. Responses were measured as peak increase in fluorescence minus basal, normalized to the maximal stimulatory effect induced by $EC_{80}$ value of orexin-A or orexin- B. Inhibition curves were fitted according to the Hill equation: $y=100/(1+(x/IC_{50})^{nH})$, where $n_H$=slope factor using Excel-fit 4 software (Microsoft). $K_b$ values were calculated according to the following equation $K_b=IC_{50}/(1+[A]/EC_{50})$ where A is the concentration of agonist added which is very close to agonist $EC_{80}$ value, and $IC_{50}$ and EC50 values were derived from the antagonist inhibition and orexin-A or B agonist curves, respectively.

The following table shows $K_b$ values (μM) in human on orexin receptor for some compounds of the invention.

| Example | $K_b$ (μM) OX2R (human) |
| --- | --- |
| 1 (I-A) | 0.0007 |
| 2 (I-A) | 0.0025 |
| 3 (I-A) | 0.0159 |
| 4 (I-A) | 0.0017 |
| 5 (I-A) | 0.0005 |
| 7 (I-A) | 0.0005 |
| 8 (I-A) | 0.0263 |
| 9 (I-A) | 0.0006 |
| 10 (I-A) | 0.0014 |
| 12 (I-A) | 0.0015 |
| 15 (I-A) | 0.0241 |
| 17 (I-A) | 0.0362 |
| 19 (I-A) | 0.0109 |
| 20 (I-A) | 0.0916 |
| 21 (I-A) | 0.0047 |
| 24 (I-A) | 0.0839 |
| 25 (I-A) | 0.0008 |
| 26 (I-A) | 0.0038 |
| 27 (I-A) | 0.068 |
| 32 (I-B) | 0.0943 |
| 36 (I-B) | 0.061 |
| 39 (I-B) | 0.0439 |
| 42 (I-B) | 0.0785 |
| 48 (I-C) | 0.07 |
| 49 (I-C) | 0.0361 |
| 54 (I-C) | 0.0078 |
| 55 (I-A) | 0.0142 |
| 56 (I-A) | 0.0176 |
| 57 (I-A) | 0.0016 |
| 58 (I-A) | 0.0167 |
| 60 (I-A) | 0.0053 |
| 61 (I-A) | 0.0026 |
| 62 (I-A) | 0.011 |
| 63 (I-A) | 0.0243 |
| 65 (I-A) | 0.0475 |
| 66 (I-A) | 0.0057 |
| 67 (I-A) | 0.073 |
| 68 (I-A) | 0.0232 |
| 70 (I-A) | 0.0863 |
| 73 (I-A) | 0.0313 |
| 75 (I-A) | 0.013 |
| 76 (I-A) | 0.026 |
| 77 (I-A) | 0.0075 |
| 78 (I-A) | 0.0481 |
| 79 (I-A) | 0.0236 |
| 80 (I-A) | 0.0289 |
| 81 (I-A) | 0.0197 |
| 86 (I-A) | 0.0378 |
| 87 (I-A) | 0.0198 |
| 88 (I-A) | 0.0106 |
| 90 (I-A) | 0.0438 |
| 92 (I-A) | 0.0146 |
| 93 (I-A) | 0.0146 |
| 95 (I-A) | 0.0195 |
| 96 (I-A) | 0.0216 |
| 97 (I-A) | 0.0276 |
| 98 (I-A) | 0.0216 |
| 99 (I-A) | 0.0285 |
| 101 (I-A) | 0.0116 |
| 102 (I-A) | 0.0116 |
| 103 (I-A) | 0.0239 |
| 106 (I-C) | 0.0249 |
| 107 (I-C) | 0.0046 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a process for the manufacture of pharmaceutical compositions. Such process comprises bringing the compound of formula I and/or pharmaceutically acceptable acid addition salt thereof and, fir desired, one or more other therapeutically valuable substances into a galenical administration form together with one or more therapeutically inert carriers.

The most preferred indications in accordance with the present invention are those, which include sleep disorders including sleep apnea, narcolepsy, insomnia, parasomnia, jet lag syndrome, circadian rhythms disorder, restless leg syndrome, psychiatric, neurological and neurodegenerative disorders including anxiety, depression, manic depression, obsessive compulsive disorders, affective neurosis, depressive neurosis, anxiety neurosis, mood disorder, delirium, panic-attack disorder, posttraumatic stress disorders, sexual dysfunction, schizophrenia, psychosis, cognitive disorders, Alzheimer's and Parkinson's diseases, dementia, mental retardation, dyskinesias such as Huntington's disease and Tourette syndrome, addictions, craving associated with drug abuse, seizure disorders, epilepsy, metabolic diseases such as obesity, diabetes, eating disorders including anorexia and bulimia, asthma, migraine, pain, neuropathic pain, sleep disorders associated with psychiatric, neurological and neurodegenerative disorders, neuropathic pain, enhanced or exaggerated sensitivity to pain such as hyperalgesia, causalgia, and allodynia, acute pain, burn pain, back pain, complex regional pain syndrome I and II, arthritic pain, post-stroke pain, post-operative pain, neuralgia, pain associated with HIV infection, post-chemotherapy pain, irritable bowel syndrome and other diseases related to general orexin system dysfunction. More preferred indications are sleep disorders, particularly sleep apnea, narcolepsy, insomnia, parasomnia, jet lag syndrome and sleep disorders associated with neurological diseases.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

| Tablet Formulation (Wet Granulation) | | | | |
|---|---|---|---|---|
| | | mg/tablet | | |
| Item | Ingredients | 5 mg | 25 mg | 100 mg | 500 mg |
|---|---|---|---|---|---|
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| Capsule Formulation | | | | |
|---|---|---|---|---|
| | | mg/capsule | | |
| Item | Ingredients | 5 mg | 25 mg | 100 mg | 500 mg |
|---|---|---|---|---|---|
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

EXAMPLE 1

(S)-2-Amino-N-(3,4-dimethyl-phenyl)-2-phenyl-N-[2-(6-trifluoromethyl-pyridin-3-yl)-ethyl]-acetamide

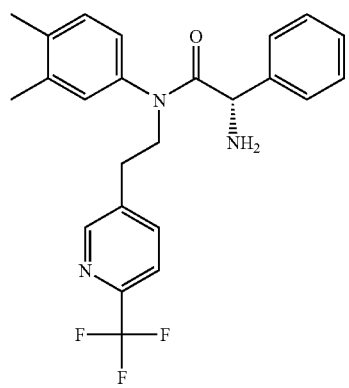

a) Step 1:

(6-Trifluoromethyl-pyridin-3-yl)-acetonitrile

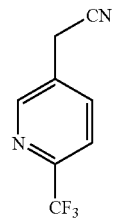

To a solution of (6-trifluoromethyl-pyridin-3-yl)-methanol (4.93 g, 27.8 mmol) in THF (50 mL) were added N,N-diisopropyl ethyl amine (5.7 mL, 33 mmol) and 4-dimethyl-aminopyridine (17 mg, 0.14 mmol). After cooling to 0° C. thionyl chloride (4.8 mL, 56 mmol) was added dropwise over a period of 10 min. After stirring for 30 min. at 0° C., the ice bath was replaced with a water bath and stirred for 2 h at ambient temperature. The resulting brown reaction mixture was concentrated in vacuo, diluted with TBME (50 mL) and cooled to 0° C. before aqueous NaHCO$_3$ (1M, 100 mL) was added. The mixture was stirred for 30 min., the aqueous layers were extracted with TBME (50 mL) and the combined organic layers were washed with aqueous NaHCO$_3$ (1M, 50 mL) and brine (50 mL). Drying over sodium sulphate was followed by concentration. The resulting oil (6.44 g) was dissolved in DMSO (15 mL) and sodium cyanide (1.36 g, 27.8 mmol) was added. The resulting dark reaction mixture was stirred for 18 h at ambient temperature under a nitrogen atmosphere. It was diluted with TBME (50 mL) and treated with ice (30 g) and water (50 mL). The aqueous layer was separated and extracted with TBME (50 mL). The organic layers were washed twice with water (50 mL) and brine (30 mL), dried over sodium sulfate and concentrated. Purification by chromatography (SiO$_2$, heptane:ethyl acetate=95:5 to 50:50) afforded the title compound (3.59 g, 59%) as a light brown oil. MS m/e: 185.3 [M−H]$^-$.

b) Step 2:

(6-Trifluoromethyl-pyridin-3-yl)-acetic acid

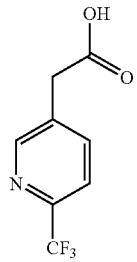

To a solution of (6-trifluoromethyl-pyridin-3-yl)-acetonitrile (217 mg, 1.17 mmol) in dioxane (0.5 mL) was added aqueous hydrochloric acid (6 M, 971 µl, 5.83 mmol). The reaction mixture was irradiated in the microwave for 30 min at 130° C. The resulting solution was concentrated affording the title compound (267 mg, 99%) as a white solid. MS m/e: 206.0 [M+H]$^+$.

c) Step 3:

(3,4-Dimethyl-phenyl)-[2-(6-trifluoromethyl-pyridin-3-yl)-ethyl]-amine

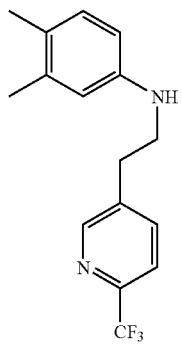

To a suspension of (6-trifluoromethyl-pyridin-3-yl)-acetic acid (257 mg, 1.25 mmol), 3,4-dimethylaniline (167 mg, 1.38 mmol) and 1-hydroxybenzotriazole in dichloromethane (2 mL) was added under a nitrogen atmosphere 1-(3-dimethylaminopropyl)-3-ethylcarbodiimide hydrochloride (264 mg, 1.37 mmol) and N,N-diisopropyl ethyl amine (322 µl, 1.88 mmol). After stirring for 3 h at ambient temperature, the reaction mixture was concentrated and a solution of borane-tetrahydrofuran complex (1 M in THF, 5 mL, 5 mmol) was added and the reaction mixture was stirred for 18 h at 60° C. A further portion of the borane-tetrahydrofuran complex (1 M in THF, 5 mL, 5 mmol) was added and the reaction mixture was stirred for 4 h at 80° C. An aqueous solution of hydrochloric acid (1 M, 2 mL) was carefully added and stirring was continued for 15 min. at reflux. After cooling it was diluted with ethyl acetate (15 mL) and washed with aqueous Na$_2$CO$_3$ (saturated, 15 mL). The aqueous layer was extracted with EtOAc (15 mL) and the combined organic layers dried over sodium sulfate. Concentration and purification by chromatography (SiO$_2$, heptane:ethyl acetate=95:5 to 60:40) afforded the title compound (218 mg, 64%) as a light yellow oil. MS m/e: 295.2 [M+H]$^+$.

d) Step 4:

(S)-2-Amino-N-(3,4-dimethyl-phenyl)-2-phenyl-N-[2-(6-trifluoromethyl-pyridin-3-yl)-ethyl]-acetamide To a solution of (3,4-dimethyl-phenyl)-[2-(6-trifluoromethyl-pyridin-3-yl)-ethyl]-amine (100 mg, 0.34 mmol) in CH$_2$Cl$_2$ (3 mL) was added under a nitrogen atmosphere at 0° C. t-BOC-L-phenylglycine (105 mg, 0.70 mmol), EDC (71 mg, 0.374 mmol). After stirring for 3 h, the mixture was treated with TFA (10 eq., 3.4 mmol) and stirring continued for 5 h at ambient temperature. After washing with aqueous Na$_2$CO$_3$ (saturated, 15 mL) and water (15 mL), the combined aqueous layers were extracted with CH$_2$Cl$_2$ (15 mL) and the combined organic layers dried over sodium sulfate. Concentration and purification by chromatography (SiO$_2$, CH$_2$Cl$_2$: MeOH=100:0 to 90:10) afforded the title compound (70 mg, 48%) as a light yellow oil. MS m/e: 428.3 [M+H]$^+$.

EXAMPLE 2

(S)—N-(3,4-Dimethyl-phenyl)-2-hydroxy-2-phenyl-N-[2-(6-trifluoromethyl-pyridin-3-yl)-ethyl]-acetamide

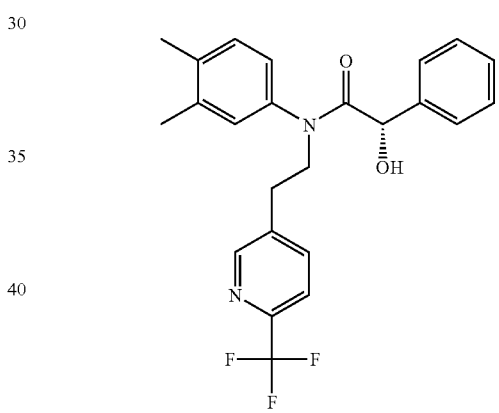

To a solution of (3,4-dimethyl-phenyl)-[2-(6-trifluoromethyl-pyridin-3-yl)-ethyl]-amine (800 mg, 0.27 mmol, prepared as described in example 1, step 3) in CH$_2$Cl$_2$ (3 mL) was added under a nitrogen atmosphere at 0° C. benzoylformic acid (61 mg, 0.41 mmol), EDC (130 mg, 0.68 mmol). After stirring for 1 h, the mixture was concentrated and redissolved in MeOH (3 mL) and treated with NaBH$_4$ (206 mg, 5.44 mmol) and stirring continued for 3 h at ambient temperature. It was diluted with TBME (15 mL) and aqueous K$_2$CO$_3$ (2 M, 15 mL), stirred further for 20 min, the layers separated and the organic layer washed with water (15 mL). The combined aqueous layers were extracted with TBME (15 mL) and the combined organic layers dried over sodium sulfate. Concentration and purification by chromatography (SiO$_2$, heptane: ethyl acetate=95:5 to 60:40) afforded the racemic compound (78 mg, 67%) as a pale yellow oil. MS m/e: 429.2 [M+H]$^+$ which was then separated by chiral HPLC to provide the title compound as an off white solid MS m/e: 429.2 [M+H]$^+$.

EXAMPLE 3

(R)—N-(3,4-Dimethyl-phenyl)-2-hydroxy-2-phenyl-N-[2-(6-trifluoromethyl-pyridin-3-yl)-ethyl]-acetamide

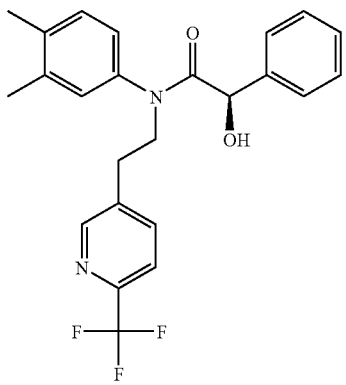

The racemic mixture from example 2 was separated by chiral HPLC to provide the title compound as an off white solid MS m/e: 429.2 [M+H]$^+$.

EXAMPLE 4

(S)-2-((S)-2-Amino-2-phenyl-acetylamino)-N-(3,4-dimethoxy-phenyl)-2-phenyl-N-[2(6-trifluoromethyl-pyridin-3-yl)-ethyl]-acetamide

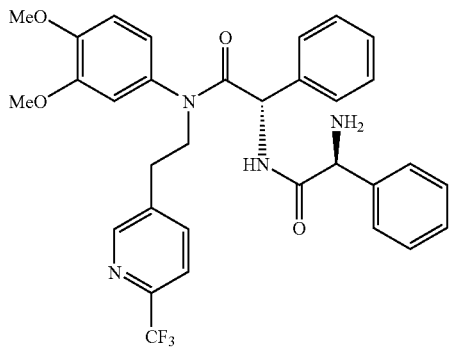

a) Step 1:

(3,4-Dimethoxy-phenyl)-[2-(6-trifluoromethyl-pyridin-3-yl)-ethyl]-amine

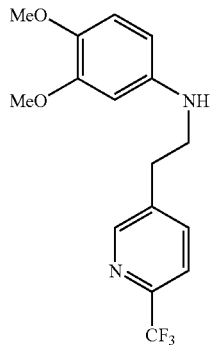

A solution of (6-trifluoromethyl-pyridin-3-yl)-acetonitrile_(186 mg, 1.00 mmol, prepared as per example 1, step 1) and 3,4-dimethoxyaniline (306 mg, 2.00 mmol) in MeOH (10 mL) was treated with NH$_4$OAc (12.00 mmol) and 10% Pd/C (200 mg) and stirred at ambient temperature for 72 h. Filtration, concentration and purification by chromatography (SiO$_2$, heptane:ethyl acetate=95:5 to 60:40) afforded the title compound (147 mg, 45%) as a light yellow oil. MS m/e: 327.4 [M+H]$^+$.

b) Step 2:

(S)-2-((S)-2-Amino-2-phenyl-acetylamino)-N-(3,4-dimethoxy-phenyl)-2-phenyl-N-[2(6-trifluoromethyl-pyridin-3-yl)-ethyl]-acetamide To a solution of (3,4-dimethoxy-phenyl)-[2-(6-trifluoromethyl-pyridin-3-yl)-ethyl]-amine (147 mg, 0.45 mmol) in CH$_2$Cl$_2$ (2 mL) was added under a nitrogen atmosphere at 0° C. t-BOC-L-phenylglycine (226 mg, 0.90 mmol) and EDC (172 mg, 0.901 mmol). After stirring for 1.5 h, the mixture was treated with TFA (10 eq., 4.50 mmol) and stirring continued for 8 h at ambient temperature. After washing with aqueous Na$_2$CO$_3$ (saturated, 15 mL) and water (15 mL), the combined aqueous layers were extracted with CH$_2$Cl$_2$ (3×15 mL) and the combined organic layers dried over sodium sulfate. Concentration and purification by chromatography (SiO$_2$, CH$_2$Cl$_2$:MeOH=100:0 to 90:10) afforded the title compound (31 mg, 12%) as a light yellow oil. MS m/e: 593.1 [M+H]$^+$.

EXAMPLE 5

(S)-2-Amino-N-(3,4-dimethoxy-phenyl)-2-phenyl-N-[2-(6-trifluoromethyl-pyridin-3-yl)-ethyl]-acetamide

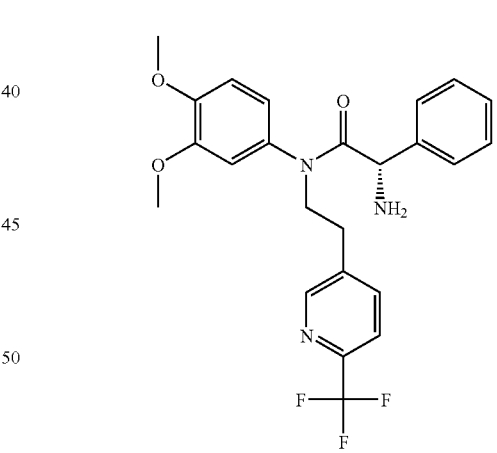

To a solution of (3,4-dimethoxy-phenyl)-[2-(6-trifluoromethyl-pyridin-3-yl)-ethyl]-amine (27 mg, 0.083 mmol, prepared as in example 4, step 1) in CH$_2$Cl$_2$ (2 mL) was added under a nitrogen atmosphere at 0° C. t-BOC-L-phenylglycine (28 mg, 0.11 mmol) and EDC (80 mg, 0.42 mmol). After stirring for 1.5 h, the mixture was treated with TFA (10 eq., 0.83 mmol) and stirring continued for 8 h at ambient temperature. After washing with aqueous Na$_2$CO$_3$ (saturated, 15 mL) and water (15 mL), the combined aqueous layers were extracted with CH$_2$Cl$_2$ (3×15 mL) and the combined organic layers dried over sodium sulfate. Concentration and purification by chromatography (SiO$_2$, CH$_2$Cl$_2$:MeOH=100:0 to 90:10) afforded the title compound (27 mg, 71%) as a light yellow oil. MS m/e: 460.1 [M+H]+.

EXAMPLE 6

(S)-2-Amino-N-(1,3-dimethyl-2-oxo-2,3-dihydro-1H-benzoimidazol-5-yl)-2-phenyl-N-[2-(6-trifluoromethyl-pyridin-3-yl)-ethyl]-acetamide

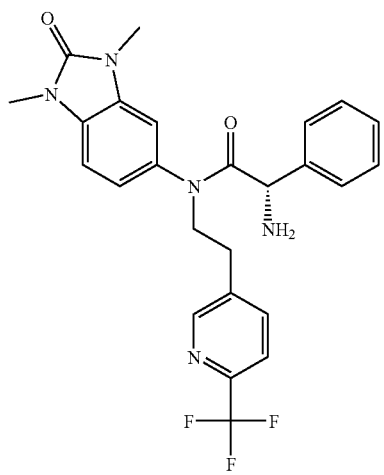

a) Step 1:

1,3-Dimethyl-5-[2-(6-trifluoromethyl-pyridin-3-yl)-ethylamino]-1,3-dihydrobenzoimidazol-2-one

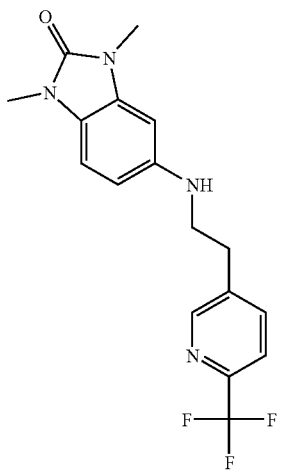

A solution of (6-trifluoromethyl-pyridin-3-yl)-acetonitrile (223 mg, 1.21 mmol, prepared as per example 1, step 1) and 1,3-dimethyl-5-nitro-1,3-dihydro-benzoimidazol-2-one (240 mg, 2.41 mmol, commercially available) in MeOH (10 mL) was treated with NH4OAc (13.00 mmol) and 10% Pd/C (200 mg) and stirred at 60° C. for 72 h. Filtration, concentration and purification by chromatography (SiO2, heptane:ethyl acetate=95:5 to 60:40) afforded the title compound (216 mg, 25%) as a light yellow oil. MS m/e: 351.1 [M+H]+.

b) Step 2:

(S)-2-Amino-N-(1,3-dimethyl-2-oxo-2,3-dihydro-1H-benzoimidazol-5-yl)-2-phenyl-N-[2-(6-trifluoromethyl-pyridin-3-yl)-ethyl]-acetamide In analogy to example 5, step 2, 1,3-dimethyl-5-[2-(6-trifluoromethyl-pyridin-3-yl)-ethylamino]-1,3-dihydrobenzoimidazol-2-one (80 mg, 0.228 mmol) was coupled to t-BOC-L-phenylglycine (80 mg, 0.32 mmol) to afford the title compound (58 mg, 5 3%) as a light yellow oil. MS m/e: 484.2 [M+H]+.

EXAMPLE 7

(S)—N-(3,4-Dimethyl-phenyl)-2-(4-fluoro-phenyl)-2-hydroxy-N-[2-(6-trifluoromethyl-pyridin-3-yl)-ethyl]-acetamide

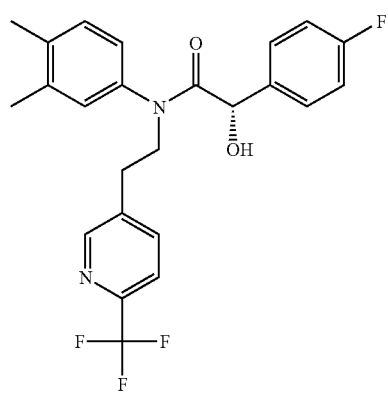

a) Step 1:

N-(3,4-Dimethyl-phenyl)-2-(4-fluoro-phenyl)-2-oxo-N-[2-(6-trifluoromethyl-pyridin-3-yl)-ethyl]-acetamide

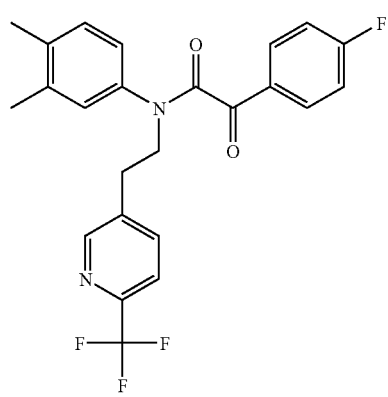

To a solution of (3,4-dimethyl-phenyl)-[2-(6-trifluoromethyl-pyridin-3-yl)-ethyl]-amine (500 mg, 1.70 mmol, as described in example 1, step 3) in CH2Cl2 (15 mL) was added under a nitrogen atmosphere at 0° C. (4-fluoro-phenyl)-oxoacetic acid (300 mg, 1.78 mmol, commercially available) and EDC (342 mg, 1.78 mmol). After stirring for 12 h a ambient temperature, the mixture was washed with aqueous $Na_2CO_3$ (saturated, 15 mL) and water (15 mL), the combined aqueous layers were extracted with $CH_2Cl_2$ (3×15 mL) and the combined organic layers dried over sodium sulfate. Concentration and purification by chromatography ($SiO_2$, heptane:ethyl acetate=95:5 to 60:40) afforded the title compound (527 mg, 70%) as a light yellow oil.

b) Step 2:

(S)—N-(3,4-Dimethyl-phenyl)-2-(4-fluoro-phenyl)-2-hydroxy-N-[2-(6-trifluoromethyl-pyridin-3-yl)-ethyl]-acetamide A solution of N-(3,4-dimethyl-phenyl)-2-(4-fluoro-phenyl)-2-oxo-N-[2-(6-trifluoromethyl-pyridin-3-yl)-ethyl]-acetamide (515 mg, 1.16 mmol) was dissolved in MeOH (8 mL), cooled to 0° C. and treated with $NaBH_4$ (88 mg, 2.33 mmol) and stirred for 12 h at ambient temperature. The reaction mixture was quenched with aqueous $K_2CO_3$ (2 M, 1 mL), concentrated, then redissolved in EtOAc (15 mL) and washed with aqueous $K_2CO_3$ (2 M, 3×15 mL). The combined aqueous layers were extracted with EtOAc (3×15 mL) and the combined organic layers dried over sodium sulfate. Concentration and purification by chromatography ($SiO_2$, heptane:ethyl acetate=95:5 to 60:40) afforded the racemic compound (501 mg, 97%) as a lightyellow oil. Separation by chromatography on a chiral column provided the title compound as a colourless oil MS m/e: 447.2 $[M+H]^+$ which crystallized upon standing.

EXAMPLE 8

(S)-2-(3-Aminomethyl-oxetan-3-ylamino)-N-(3,4-dimethyl-phenyl)-2-phenyl-N-[2-(6-trifluoromethyl-pyridin-3-yl)-ethyl]acetamide

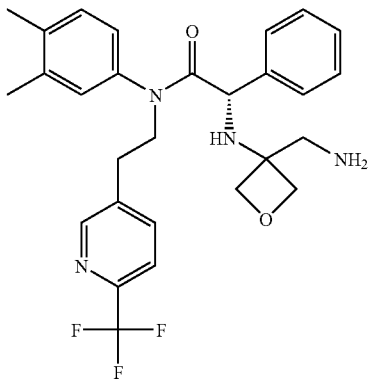

A solution of (S)-2-amino-N-(3,4-dimethyl-phenyl)-2-phenyl-N-[2-(6-trifluoromethyl-pyridin-3-yl)-ethyl]-acetamide (50 mg, 0.11 mmol, prepared as in example 1) and 3-nitromethylene-oxetane (12 mg, 0.104 mmol, [CAS No. 922500-95-6]) in $CH_2Cl_2$ (0.5 mL) was treated with $Et_3N$ (11 mg, 0.11 mmol) at 0° C. After stirring for 30 min at ambient temperature, the mixture was concentrated, dissolved in MeOH (1 mL) and treated with a solution of $HCO_2NH_4$ (300 mg, 4.76 mmol) in $H_2O$ (0.5 mL), 10% Pd/C (100 mg) and the mixture stirred for 12 h at ambient temperature. After the addition of 1N $Na_2CO_3$ (15 mL), the aqueous layers were filtered then extracted with $CH_2Cl_2$ (3×15 mL) and the combined organic layers dried over sodium sulfate. Concentration and purification by chromatography ($SiO_2$, $CH_2Cl_2$:MeOH=100:0 to 90:10) afforded the title compound (26 mg, 46%) as a light yellow oil. MS m/e: 513.5 $[M+H]^+$.

EXAMPLE 9

(S)-2-Amino-2-phenyl-N-(5,6,7,8-tetrahydro-naphthalen-2-yl)-N-[2-(6-trifluoromethyl-pyridin-3-yl)-ethyl]-acetamide

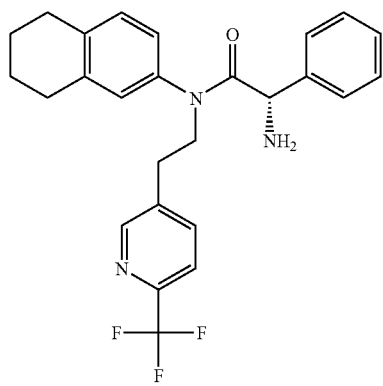

a) Step 1:

(5,6,7,8-Tetrahydro-naphthalen-2-yl)-[2-(6-trifluoromethyl-pyridin-3-yl)-ethyl]-amine

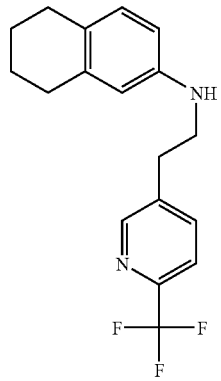

A solution of 5,6,7,8-tetrahydro-naphthalen-2-ylamine (1.132 g, 6.08 mmol, commercially available) and (6-trifluoromethyl-pyridin-3-yl)-acetonitrile (distilled 166-175° C./2 mb, 0.985 g, 6.69 mmol, prepared as per example 1, step 1) in MeOH (10 mL) was treated with $HCO_2NH_4$ (2.301 g, 36.5 mmol) and 10% Pd/C (250 mg) and stirred at 80° C. for 1.5 h. Filtration, concentration and purification by chromatography ($SiO_2$, heptane:ethyl acetate=95:5 to 60:40) afforded the title compound (1.333 g, 68%) as an off-white solid. MS m/e: 321.1 $[M+H]^+$.

b) Step 2:

(S)-2-Amino-2-phenyl-N-(5,6,7,8-tetrahydro-naphthalen-2-yl)-N-[2-(6-trifluoromethyl-pyridin-3-yl)-ethyl]-acetamide (5,6,7,8-Tetrahydro-naphthalen-2-yl)-[2-(6-trifluoromethyl-pyridin-3-yl)-ethyl]-amine (150 mg, 0.468 mmol) and t-BOC-L-phenylglycine (141 mg, 0.561 mmol) were coupled together as for example 5 to afford the title compound (81 mg, 38%) as a pale yellow oil which crystallized upon standing MS m/e: 454.3 [M+H]$^+$.

EXAMPLE 10

(S)-2-Amino-N-(3,4-dimethyl-phenyl)-2-(4-fluoro-phenyl)-N-[2-(6-trifluoromethyl-pyridin-3-yl)-ethyl]-acetamide

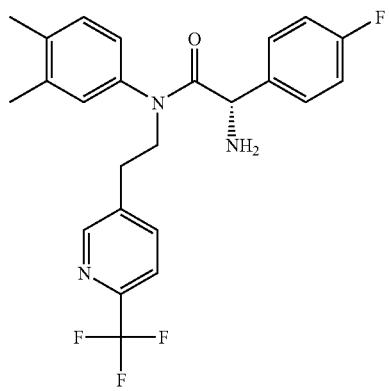

In analogy to example 1, (3,4-dimethyl-phenyl)-[2-(6-trifluoromethyl-pyridin-3-yl)-ethyl]-amine (250 mg, 0.85 mmol, prepared as per example 1, step 3) and tert-butoxycarbonylamino-(4-fluoro-phenyl)-acetic acid (343 mg, 1.27 mmol, commercially available) were coupled together and resolved by chromatography on a chiral columnto afford the title compound (48 mg, 13%) as a pale yellow oil which crystallized upon standing MS m/e: 446.2 [M+H]$^+$.

EXAMPLE 11

(R)-2-Amino-N-(3,4-dimethyl-phenyl)-2-(4-fluoro-phenyl)-N-[2-(6-trifluoromethyl-pyridin-3-yl)-ethyl]-acetamide

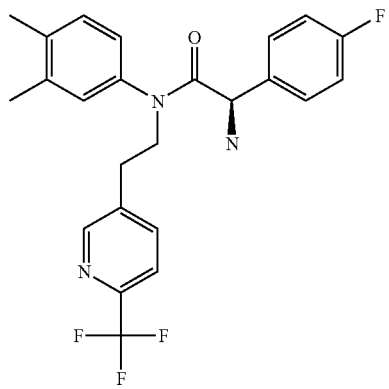

The racemic amine from example 10 was resolved by chromatography on a chiral columnto afford the title compound (51 mg, 14%) as a pale yellow oil which crystallized upon standing. MS m/e: 446.2 [M+H]$^+$.

EXAMPLE 12

(S)-2-Hydroxy-2-phenyl-N-(5,6,7,8-tetrahydro-naphthalen-2-yl)-N-[2-(6-trifluoromethyl-pyridin-3-yl)-ethyl]-acetamide

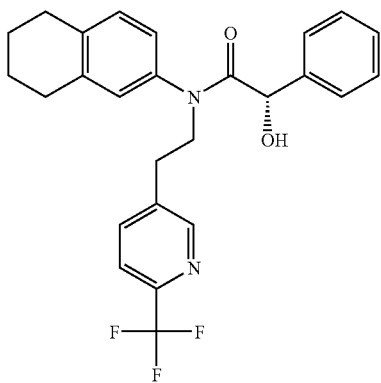

a) Step 1:

2-Oxo-2-phenyl-N-(5,6,7,8-tetrahydro-naphthalen-2-yl)-N-[2-(6-trifluoromethyl-pyridin-3-yl)-ethyl]-acetamide:

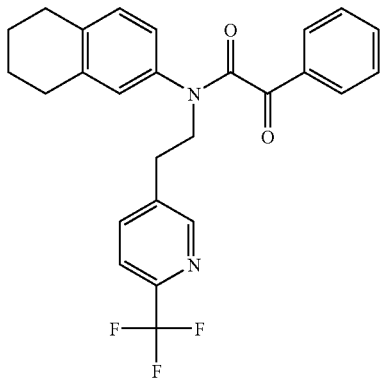

In analogy to example 7, step 1, (5,6,7,8-tetrahydro-naphthalen-2-yl)-[2-(6-trifluoromethyl-pyridin-3-yl)-ethyl]-amine (250 mg, 0.78 mmol, prepared as described in example 9, step 1) and benzoylformic acid (141 mg, 0.939 mmol) were coupled to provide the title compound (355 mg, 100%) as a yellow oil which was used without further purification in the next step.

b) Step 2:

(S)-2-Hydroxy-2-phenyl-N-(5,6,7,8-tetrahydro-naph-thalen-2-yl)-N-[2-(6-trifluoromethyl-pyridin-3-yl)-ethyl]-acetamide

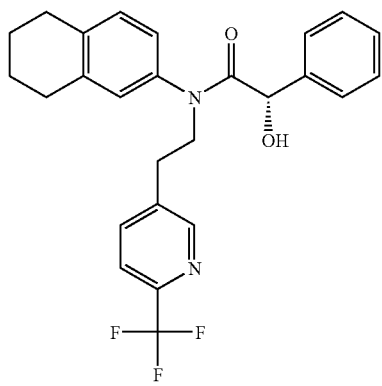

2-Oxo-2-phenyl-N-(5,6,7,8-tetrahydro-naphthalen-2-yl)-N-[2-(6-trifluoromethyl-pyridin-3-yl)-ethyl]-acetamide (355 mg, 0.79 mmol) was reduced in analogy to example 7, step 2 to give the title compound as a pale yellow oil which crystallized upon standing (63 mg, 18%) MS m/e: 455.2 [M+H]$^+$.

EXAMPLE 13

(S)—N-(3,4-Dimethyl-phenyl)-2-hydroxy-2-pyridin-3-yl-N-[2-(6-trifluoromethyl-pyridin-3-yl)-ethyl]-acetamide

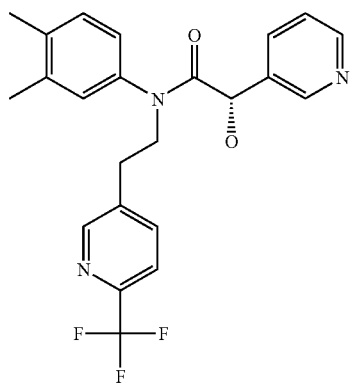

In analogy to example 7, (3,4-dimethyl-phenyl)-[2-(6-trifluoromethyl-pyridin-3-yl)-ethyl]-amine (250 mg, 0.85 mmol) and oxo-pyridin-3-yl-acetic acid (343 mg, 1.27 mmol, CAS 39684-37-2) were coupled together to afford the title compound (48 mg, 27%) as a colourless solid. MS m/e: 430.2 [M+H]$^+$.

EXAMPLE 14

(R)-2-Hydroxy-2-phenyl-N-p-tolyl-N-[2-(6-trifluoromethyl-pyridin-3-yl)-ethyl]-acetamide

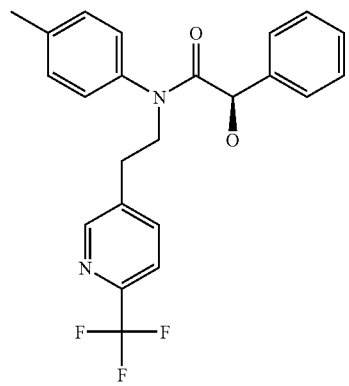

a) Step 1:

p-Tolyl-[2-(6-trifluoromethyl-pyridin-3-yl)-ethyl]-amine:

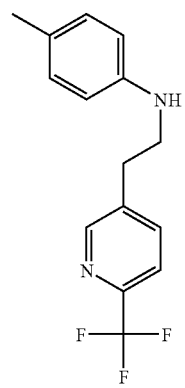

In analogy to example 9, step 1, 4-methylaniline (298 mg, 2.78 mmol) was coupled to (6-trifluoromethyl-pyridin-3-yl)-acetonitrile (750 mg, 4.03 mmol) to provide the title compound as a pale yellow oil (392 mg, 35%) MS m/e: 281.1 [M+H]$^+$.

b) Step 2

(R)-2-Hydroxy-2-phenyl-N-p-tolyl-N-[2-(6-trifluoromethyl-pyridin-3-yl)-ethyl]-acetamide In analogy to example 7, steps 1 and 2, p-tolyl-[2-(6-trifluoromethyl-pyridin-3-yl)-ethyl]-amine (200 mg, 0.714 mmol) was coupled to benzoylformic acid (112 mg, 0.746 mmol) and reduced to give the title compound (97 mg, 32.2%) MS m/e: 415.1 [M+H]+ after separation on a chiral column.

EXAMPLE 15

(S)-2-Hydroxy-2-phenyl-N-p-tolyl-N-[2-(6-trifluoromethyl-pyridin-3-yl)-ethyl]-acetamide

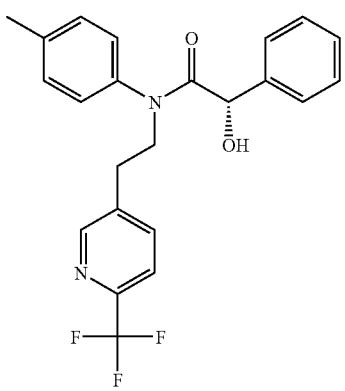

The racemic alcohol from example 14, step 2 was separated by chromatography on a chiral column to give the title compound as a colourless oil which crystallized on standing (95 mg, 31.5%) MS m/e: 415.1 [M+H]+.

EXAMPLE 16

(S)-2-Hydroxy-2-pyridin-3-yl-N-p-tolyl-N-[2-(6-trifluoromethyl-pyridin-3-yl)-ethyl]-acetamide

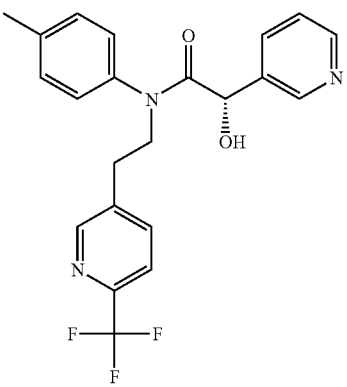

In analogy to example 13, p-tolyl-[2-(6-trifluoromethyl-pyridin-3-yl)-ethyl]-amine (95 mg, 0.34 mmol, prepared as in example 14, step1) was coupled to oxo-pyridin-3-yl-acetic acid (54 mg, 0.36 mmol) and reduced to give the title compound as a colorless oil (37 mg, 25%) MS m/e: 416.1 [M+H]+.

EXAMPLE 17

N-(3,4-Dimethyl-phenyl)-2-phenyl-N-[2-(6-trifluoromethyl-pyridin-3-yl)-ethyl]-acetamide

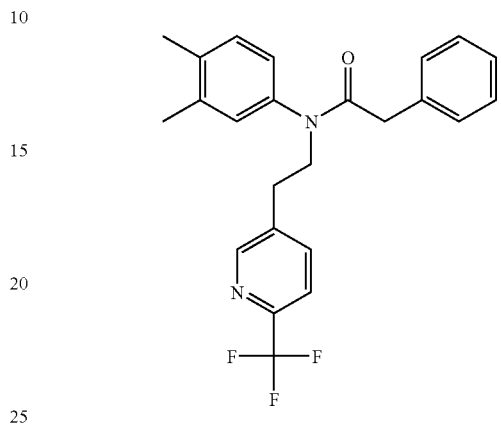

In analogy to example 1, step 4 (without TFA addition), (3,4-dimethyl-phenyl)-[2-(6-trifluoromethyl-pyridin-3-yl)-ethyl]-amine (prepared in example 1, step 3) was coupled to phenylacetic acid to provide the title compound as a pale yellow oil. MS m/e: 413.2 [M+H]+.

EXAMPLE 18

(S)—N-(3,4-Dimethyl-phenyl)-2-methanesulfonylamino-2-phenyl-N-[2-(6-trifluoromethyl-pyridin-3-yl)ethyl]acetamide

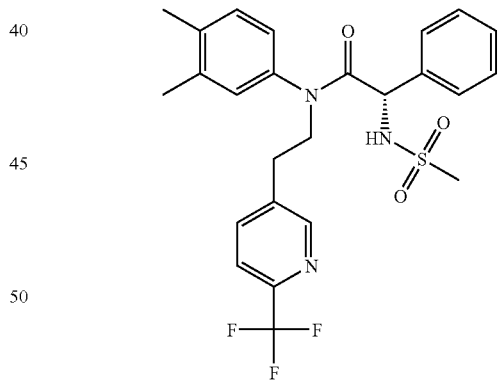

A solution of (S)-2-amino-N-(3,4-dimethyl-phenyl)-2-phenyl-N-[2-(6-trifluoromethyl-pyridin-3-yl)-ethyl]-acetamide hydrochloride (40 mg, 0.086 mmol, derived from example 1) in dry $CH_2Cl_2$ (1.5 mL) was treated with methanesulphonyl chloride (10 mg, 0.087 mmol) under Argon and the mixture stirred at ambient temperature for 30 min then quenched with aqueous $Na_2CO_3$ (2 M, 1 mL), concentrated, then redissolved in EtOAc (15 mL) and washed with aqueous $Na_2CO_3$ (2 M, 3×15 mL). The combined aqueous layers were extracted with EtOAc (15 mL) and the combined organic layers dried over sodium sulfate. Concentration and purification by chromatography ($SiO_2$, heptane:ethyl acetate=95:5 to 60:40) afforded the title compound (42 mg, 96%) as a light yellow oil. MS m/e: 506.1 [M+H]+.

EXAMPLE 19

(S)-2-Hydroxy-N-(3-methoxy-4-methyl-phenyl)-2-phenyl-N-[2-(6-trifluoromethyl-pyridin-3-yl)-ethyl]-acetamide

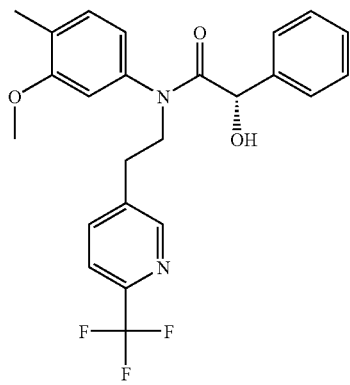

Step 1:

(3-Methoxy-4-methyl-phenyl)-[2-(6-trifluoromethyl-pyridin-3-yl)-ethyl]-amine

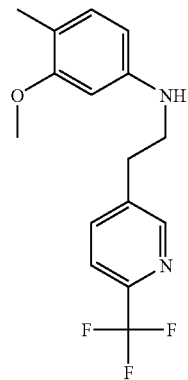

In analogy to example 6, step 1, 2-methoxy-1-methyl-4-nitro-benzene (988 mg, 5.91 mmol) was coupled to (6-trifluoromethyl-pyridin-3-yl)-acetonitrile (1.0 g, 5.37 mmol, prepared in example 1, step 1) to give the title compound (521 mg, 31%) as an orange oil MS m/e: 311.1 [M+H]$^+$.

b) Step 2:

Acetic acid (S)-{(3-methoxy-4-methyl-phenyl)-[2-(6-trifluoromethyl-pyridin-3-yl)-ethyl]-carbamoyl}-phenyl-methyl ester

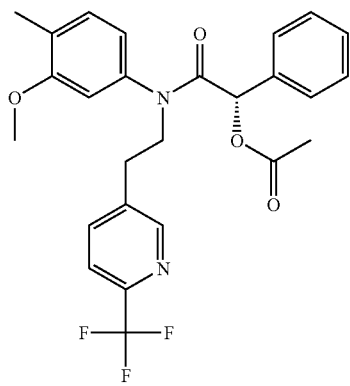

To a 0° C. solution of 100 mg (0.33 mmol) (3,4-dimethyl-phenyl)-[2-(5-trifluoromethyl-pyridin-2-yl)-ethyl]-amine and 66 mg (0.34 mmol) (S)-(+)-O-acetyl-L-mandelic acid in 3 mL dichloromethane was added 65 mg (0.34 mmol) 1-(3-dimethylaminopropyl)-3-ethylcarbodiimide hydrochloride. The mixture was stirred at 0° C. for 30 minutes. The solution was washed once with a saturated NaHCO$_3$ solution and once with water. The washings were extracted once with dichloromethane. The combined organic layers were dried over Na$_2$SO$_4$, filtered and concentrated in vacuo. The crude oil (185 mg) was used directly for the next step.

c) Step 3:

(S)-2-Hydroxy-N-(3-methoxy-4-methyl-phenyl)-2-phenyl-N-[2-(6-trifluoromethyl-pyridin-3-yl)-ethyl]-acetamide To a solution of acetic acid (S)-{(3-methoxy-4-methyl-phenyl)-[2-(6-trifluoromethyl-pyridin-3-yl)-ethyl]-carbamoyl}-phenyl-methyl ester (155 mg, 0.32 mmol) in tetrahydrofuran (2.0 mL) were added 1.0 mL water and 20.0 mg (0.84 mmol) lithium hydroxide monohydrate. The mixture was stirred at room temperature for 2 h. The mixture was diluted with water and extracted 3 times with ethyl acetate. The combined organic layers were dried over Na$_2$SO$_4$, filtered and concentrated in vacuo. The crude oil was purified with flash column chromatography on silica eluting with a gradient formed from heptane and ethylacetate to provide 13 mg (9%) of the title compound as a colourless oil. MS(m/e): 445.1 [M+H]$^+$.

EXAMPLE 20

N-(3,4-Dimethyl-phenyl)-2-oxo-2-phenyl-N-[2-(6-trifluoromethyl-pyridin-3-yl)-ethyl]-acetamide

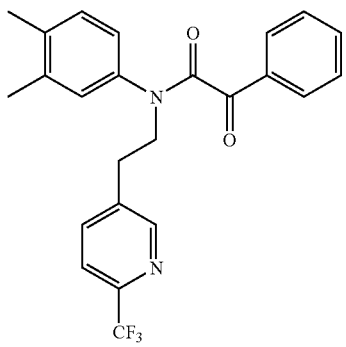

a) Step 1:

(6-Trifluoromethyl-pyridin-3-yl)-acetonitrile

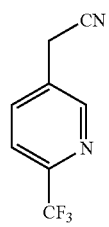

To a solution of (6-trifluoromethyl-pyridin-3-yl)-methanol (4.93 g, 27.8 mmol) in THF (50 mL) were added N,N-diisopropyl ethyl amine (5.7 mL, 33 mmol) and 4-dimethyl-aminopyridine (17 mg, 0.14 mmol). After cooling to 0° C. thionyl chloride (4.8 mL, 56 mmol) was added dropwise over a period of 10 min. After stirring for 30 min. at 0° C., the ice bath was replaced with a water bath and stirred for 2 h at ambient temperature. The resulting brown reaction mixture was concentrated in vacuo, diluted with TBME (50 mL) and cooled to 0° C. before aqueous NaHCO$_3$ (1M, 100 mL) was added. The mixture was stirred for 30 min., the aqueous layers were extracted with TBME (50 mL) and the combined organic layers were washed with aqueous NaHCO$_3$ (1M, 50 mL) and brine (50 mL). Drying over sodium sulfate was followed by concentration. The resulting oil (6.44 g) was dissolved in DMSO (15 mL) and sodium cyanide (1.36 g, 27.8 mmol) was added. The resulting dark reaction mixture was stirred for 18 h at ambient temperature under a nitrogen atmosphere. It was diluted with TBME (50 mL) and treated with ice (30 g) and water (50 mL). The aqueous layer was separated and extracted with TBME (50 mL). The organic layers were washed twice with water (50 mL) and brine (30 mL), dried over sodium sulfate and concentrated. Purification by chromatography (SiO$_2$, heptane:ethyl acetate=95:5 to 50:50) afforded the title compound (3.59 g, 59%) as a light brown oil. MS m/e: 185.3 [M−H]$^-$.

b) Step 2:

(6-Trifluoromethyl-pyridin-3-yl)-acetic acid

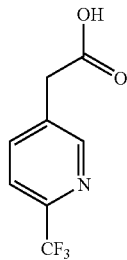

To a solution of (6-trifluoromethyl-pyridin-3-yl)-acetonitrile (217 mg, 1.17 mmol) in dioxane (0.5 mL) was added aqueous hydrochloric acid (6 M, 971 µl, 5.83 mmol). The reaction mixture was irradiated in the microwave for 30 min at 130° C. The resulting solution was concentrated affording the title compound (267 mg, 99%) as a white solid. MS m/e: 206.0 [M+H]$^+$.

c) Step 3:

(3,4-Dimethyl-phenyl)-[2-(6-trifluoromethyl-pyridin-3-yl)-ethyl]-amine

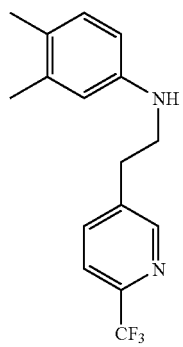

To a suspension of (6-trifluoromethyl-pyridin-3-yl)-acetic acid (257 mg, 1.25 mmol), 3,4-dimethylaniline (167 mg, 1.38 mmol) and 1-hydroxybenzotriazole in dichloromethane (2 mL) was added under a nitrogen atmosphere 1-(3-dimethylaminopropyl)-3-ethylcarbodiimide hydrochloride (264 mg, 1.37 mmol) and N,N-diisopropyl ethyl amine (322 µl, 1.88 mmol). After stirring for 3 h at ambient temperature it was concentrated and a solution of borane-tetrahydrofuran complex (1 M in THF, 5 mL, 5 mmol) was added and the reaction mixture was stirred for 18 h at 60° C. Further solution of borane-tetrahydrofuran complex (1 M in THF, 5 mL, 5 mmol) was added and the reaction mixture was stirred for 4 h at 80° C. An aqueous solution of hydrochloric acid (1 M, 2 mL) was carefully added and stirring was continued for 15 min. at reflux. After cooling it was diluted with ethyl acetate (15 mL) and washed with aqueous Na$_2$CO$_3$ (saturated, 15 mL). The aqueous layer was extracted with EtOAc (15 mL) and the combined organic layers dried over sodium sulfate. Concentration and purification by chromatography (SiO$_2$, heptane:ethyl acetate=95:5 to 60:40) afforded the title compound (218 mg, 64%) as a light yellow oil. MS m/e: 295.2 [M+H]$^+$.

d) Step 4:

N-(3,4-Dimethyl-phenyl)-2-oxo-2-phenyl-N-[2-(6-trifluoromethyl-pyridin-3-yl)-ethyl]-acetamide To a solution of (3,4-dimethyl-phenyl)-[2-(6-trifluoromethyl-pyridin-3-yl)-ethyl]-amine (172 mg, 0.58 mmol) in DMF (4 mL) was added under a nitrogen atmosphere at 0° C. benzoylformic acid (105 mg, 0.70 mmol), 2-(1H-benzotriazole-1-yl)-1,1,3,3-tetramethyl-uronium tetrafluoroborate (280 mg, 0.88 mmol) and N,N-diisopropyl ethyl amine (299 µl, 1.75 mmol). The resulting solution was stirred for 18 h at ambient temperature. It was diluted with TBME (15 mL) and washed with aqueous hydrochloric acid (1 M, 15 mL), water (15 mL), aqueous Na$_2$CO$_3$ (saturatedm, 15 mL) and brine (15 mL). The combined aqueous layers were extracted with TBME (15 mL) and the combined organic layers dried over sodium sulfate. Concentration and purification by chromatography (SiO$_2$, heptane:ethyl acetate=95:5 to 60:40) afforded the title compound (132 mg, 53%) as a light brown oil. MS m/e: 427.2 [M+H]$^+$.

EXAMPLE 21

(S)-2-Amino-N-(3,4-dimethyl-phenyl)-N-[2-(5-methyl-pyridin-2-yl)-ethyl]-2-phenyl-acetamide hydrochloride

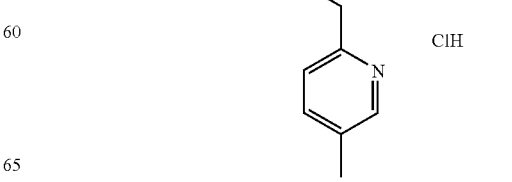

a) Step 1:

N-(3,4-Dimethyl-phenyl)-2-(5-methyl-pyridin-2-yl)-acetamide

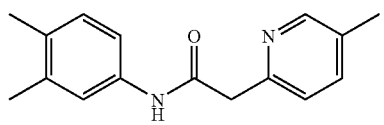

To a 0° C. solution of 400 mg (2.12 mmol) (5-methyl-pyridin-2-yl)-acetic acid hydrochloride (CAS: 848093-05-0) in 7.5 mL dichloromethane were added successively 250 mg (2.02 mmol) 3,4-dimethylaniline and 415.4 mg (2.12 mmol) 1-(3-dimethylaminopropyl)-3-ethylcarbodiimide hydrochloride. The mixture was stirred at 0° C. for 45 minutes. The solution was washed with a sat. NaHCO$_3$ solution, NaOH 2N and with water, dried over Na$_2$SO$_4$, filtered and concentrated in vacuo. The crude solid was purified with flash column chromatography on silica eluting with a gradient formed from heptane and ethylacetate to provide 0.40 g (77%) of the title compound as an off-white solid. MS (m/e): 255.2 [M+H]$^+$.

b) Step 2:

(3,4-Dimethyl-phenyl)-[2-(5-methyl-pyridin-2-yl)-ethyl]-amine

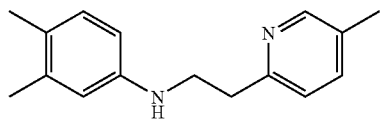

To a solution of 390 mg (1.5 mmol) N-(3,4-dimethyl-phenyl)-2-(5-methyl-pyridin-2-yl)-acetamide in 8 mL THF under argon at ambient temperature, was added dropwise 3.1 mL (3.1 mmol) of a 1 M borane-tetrahydrofuran solution. The solution was refluxed for 5 hours, cooled to 0° C. and quenched with 7 mL of a 20% NH$_4$Cl solution. The solution was acidified with HCl 5N and stirred at ambient temperature for 1.5 hours. The residue was basified with a sat. NaHCO$_3$ solution, and concentrated. The residue was dissolved in ethylacetate, the aqueous phase was extracted 2 times with ethyl acetate. The combined extracts were dried over Na$_2$SO$_4$, filtered and concentrated in vacuo. The crude oil was purified with flash column chromatography on silica eluting with a gradient formed from heptane and ethylacetate to provide 0.038 g (10%) of the title compound as a yellow oil. MS (m/e): 241.3 [M+H]$^+$.

c) Step 3:

((S)-{(3,4-Dimethyl-phenyl)-[2-(5-methyl-pyridin-2-yl)-ethyl]-carbamoyl}-phenyl-methyl)-carbamic acid tert-butyl ester

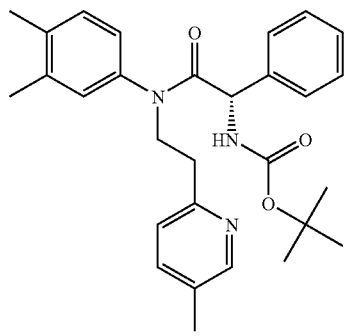

To a 0° C. solution of 35 mg (0.15 mmol) (3,4-dimethyl-phenyl)-[2-(5-methyl-pyridin-2-yl)-ethyl]-amine and 40.4 mg (0.16 mmol) Boc-L-alpha-phenylglycine in 540 uL dichloromethane under argon, was added 31.4 mg (0.16 mmol) 1-(3-dimethylaminopropyl)-3-ethylcarbodiimide hydrochloride. The mixture was stirred at 0° C. for 3 hours then at ambient temperature overnight. The solution was washed once with a sat. NaHCO$_3$ solution (3 mL) and once with water (3 mL). The combined extracts were dried over Na$_2$SO$_4$, filtered and concentrated in vacuo. The crude oil was purified with flash column chromatography on silica eluting with a gradient formed from heptane and ethylacetate to provide 0.052 g (75%) of the title compound as an oil. MS (m/e): 474.3 [M+H]$^+$.

d) Step 4:

(S)-2-Amino-N-(3,4-dimethyl-phenyl)-N-[2-(5-methyl-pyridin-2-yl)-ethyl]-2-phenyl-acetamide dihydrochloride To a solution of 50 mg (0.11 mmol) ((S)-{(3,4-dimethyl-phenyl)-[2-(5-methyl-pyridin-2-yl)-ethyl]-carbamoyl}-phenyl-methyl)-carbamic acid tert-butyl ester in 0.2 mL dioxane was added 265 uL (1.06 mmol) of a 4 M HCl solution in dioxane. The mixture was stirred at room temperature for 18 hours. The solvent was removed in vacuo. Ethylacetate was added and the mixture was stirred slowly at ambient temperature. The solid was filtered, rinsed with ether and dried under vacuum to provide 0.044 g (94%) of the title compound as a light yellow solid MS (m/e): 374.3 [M+H]$^+$.

EXAMPLE 22

(S)-2-Amino-N-(3,4-dimethyl-phenyl)-2-phenyl-N-(2-pyridin-2-yl-ethyl)-acetamide hydrochloride

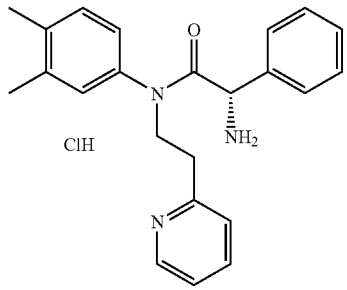

a) Step 1:

(3,4-Dimethyl-phenyl)-(2-pyridin-2-yl-ethyl)-amine

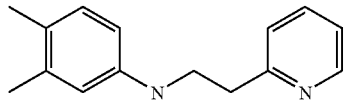

A dried flask was charged with 21 mg (0.11 mmol) CuI and 1.4 g (4.3 mmol) cesium carbonate under argon. 0.31 g (2.6 mmol) 2-pyridin-2-yl-ethylamine (CAS: 2706-56-1), 0.5 g (2.1 mmol) 4-iodo-0-xylene in solution in 1 mL dried DMF and finally 0.058 mL (0.43 mmol) 2-acetylcyclohexanone were successively added. The mixture was stirred at room temperature for 17 hours and then in a 65° C. oil-bath for 7 hours. The mixture was diluted with water. The aqueous layer was extracted twice with ethyl acetate. The combined extracts were dried over $Na_2SO_4$, filtered and concentrated in vacuo. The crude oil was purified with flash column chromatography on silica eluting with a gradient formed from heptane and ethylacetate to provide 0.15 g (31%) of the title compound as a yellow oil. MS (m/e): 227.2 $[M+H]^+$.

b) Step 2:

{(S)-[(3,4-Dimethyl-phenyl)-(2-pyridin-2-yl-ethyl)-carbamoyl]-phenyl-methyl}-carbamic acid tert-butyl ester

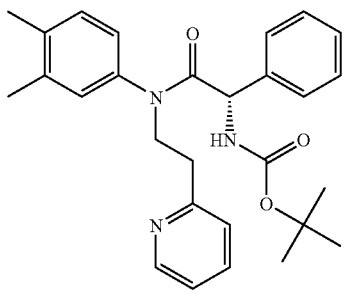

In analogy to the procedure described for the synthesis example 21, step 3, the title compound was prepared from (3,4-dimethyl-phenyl)-(2-pyridin-2-yl-ethyl)-amine and boc-L-alpha-phenylglycine. MS (m/e): 460.3 $[M+H]^+$.

c) Step 3:

(S)-2-Amino-N-(3,4-dimethyl-phenyl)-2-phenyl-N-(2-pyridin-2-yl-ethyl)-acetamide; dihydrochloride In analogy to the procedure described for the synthesis example 21, step 4, the title compound was prepared from {(S)-[(3,4-dimethyl-phenyl)-(2-pyridin-2-yl-ethyl)-carbamoyl]-phenyl-methyl}-carbamic acid tert-butyl ester. MS (m/e): 360.2 $[M+H]^+$.

EXAMPLE 23

(S)-2-Amino-N-(3,4-dimethyl-phenyl)-2-phenyl-N-(2-pyridin-3-yl-ethyl)-acetamide hydrochloride

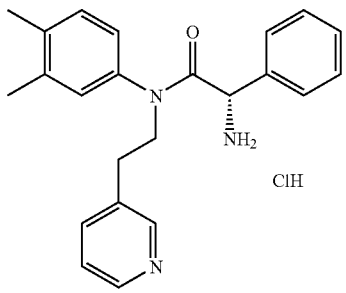

a) Step 1:

(3,4-Dimethyl-phenyl)-(2-pyridin-3-yl-ethyl)-amine

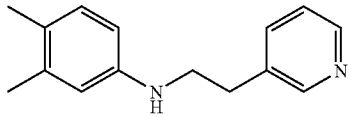

In analogy to the procedure described for the synthesis of example 22, step 1, the title compound was prepared from 4-iodo-o-xylene and 2-pyridin-3-yl-ethylamine (CAS: 20173-24-4). MS (m/e): 227.2 $[M+H]^+$.

b) Step 2:

{(S)-[(3,4-Dimethyl-phenyl)-(2-pyridin-3-yl-ethyl)-carbamoyl]-phenyl-methyl}-carbamic acid tert-butyl ester

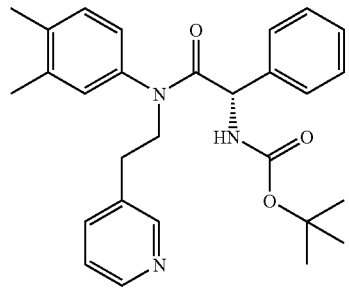

In analogy to the procedure described for the synthesis example 21, step 3, the title compound was prepared from (3,4-dimethyl-phenyl)-(2-pyridin-3-yl-ethyl)-amine and boc-L-alpha-phenylglycine. MS (m/e): 460.3 $[M+H]^+$.

c) Step 3:

(S)-2-Amino-N-(3,4-dimethyl-phenyl)-2-phenyl-N-(2-pyridin-3-yl-ethyl)-acetamide hydrochloride In analogy to the procedure described for the synthesis example 21, step 4, the title compound was prepared from {(S)-[(3,4-dimethyl-phenyl)-(2-pyridin-3-yl-ethyl)-carbamoyl]-phenyl-methyl}-carbamic acid tert-butyl ester. MS (m/e): 360.4 $[M+H]^+$.

EXAMPLE 24

(S)—N-(3,4-Dimethyl-phenyl)-2-phenyl-N-[2-(6-trifluoromethyl-pyridin-3-yl)-ethyl]-propionamide

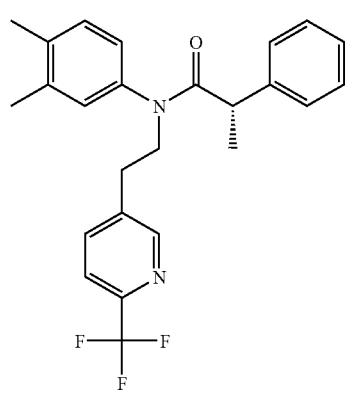

In analogy to the procedure described for the synthesis example 21, step 3, the title compound was prepared from (3,4-dimethyl-phenyl)-[2-(6-trifluoromethyl-pyridin-3-yl)-ethyl]-amine (example 20, step 3) and S(+)-2-phenylpropionic acid. MS (m/e): 427.3 [M+H]⁺.

EXAMPLE 25

(S)-2-Amino-N-(3,4-dimethyl-phenyl)-2-phenyl-N-[2-(5-trifluoromethyl-pyridin-2-yl)-ethyl]-acetamide hydrochloride

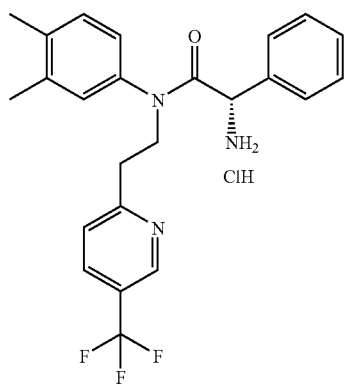

a) Step 1:

(3,4-Dimethyl-phenyl)-[2-(5-trifluoromethyl-pyridin-2-yl)-ethyl]-amine

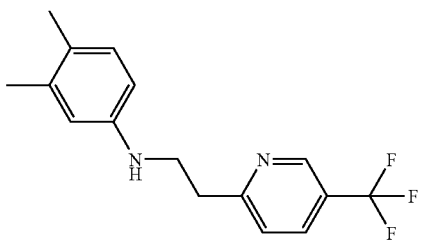

A mixture of 200 mg (0.92 mmol) 5-trifluoromethyl-2-vinyl-pyridine (CAS: 204569-89-1), 570 mg (4.62 mmol) 3,4-dimethylaniline and 33 mg (0.18 mmol) cesium hydroxide monohydrate in 2 mL NMP was heated in a 120° C. oil-bath for 22 hours. The mixture was cooled to room temperature and diluted with ethyl acetate. The solution was washed 3 times with water, dried over Na₂SO₄, filtered and concentrated in vacuo. The crude oil was purified with flash column chromatography on silica eluting with a gradient formed from heptane and ethylacetate to provide 0.17 g (63%) of the title compound as a light yellow oil. MS (m/e): 295.2 [M+H]⁺.

b) Step 2:

((S)-{(3,4-Dimethyl-phenyl)-[2-(5-trifluoromethyl-pyridin-2-yl)-ethyl]-carbamoyl}-phenyl-methyl)-carbamic acid tert-butyl ester

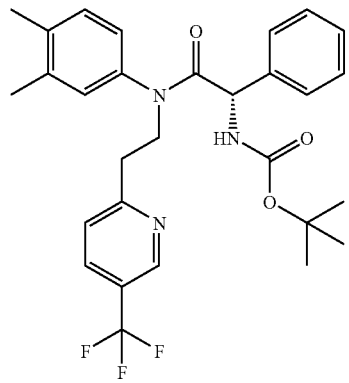

In analogy to the procedure described for the synthesis example 21, step 3, the title compound was prepared from (3,4-dimethyl-phenyl)-[2-(5-trifluoromethyl-pyridin-2-yl)-ethyl]-amine and boc-L-alpha-phenylglycine. MS (m/e): 528.3 [M+H]⁺.

c) Step 3:

(S)-2-Amino-N-(3,4-dimethyl-phenyl)-2-phenyl-N-[2-(5-trifluoromethyl-pyridin-2-yl)-ethyl]-acetamide hydrochloride In analogy to the procedure described for the synthesis example 21, step 4, the title compound was prepared from ((S)-{(3,4-dimethyl-phenyl)-[2-(5-trifluoromethyl-pyridin-2-yl)-ethyl]-carbamoyl}-phenyl-methyl)-carbamic acid tert-butyl ester. MS (m/e): 428.1 [M+H]⁺.

EXAMPLE 26

(S)—N-(3,4-Dimethyl-phenyl)-2-hydroxy-2-phenyl-N-[2-(5-trifluoromethyl-pyridin-2-yl)-ethyl]-acetamide

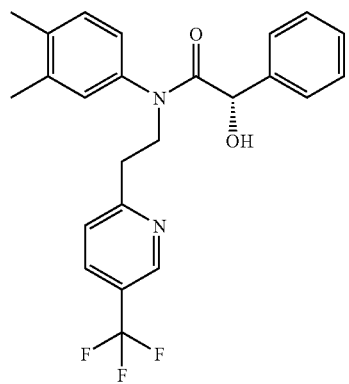

a) Step 1:

Acetic acid (S)-{(3,4-dimethyl-phenyl)-[2-(5-trifluoromethyl-pyridin-2-yl)-ethyl]-carbamoyl}-phenyl-methyl ester

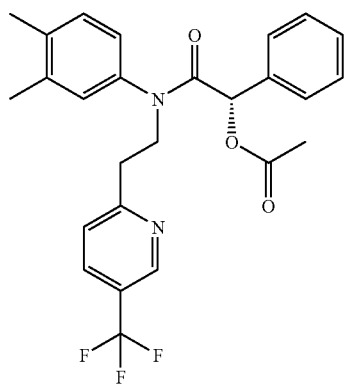

To a 0° C. solution of 90 mg (0.31 mmol) (3,4-dimethyl-phenyl)-[2-(5-trifluoromethyl-pyridin-2-yl)-ethyl]-amine (example 25, step 1) and 65 mg (0.337 mmol) (S)-(+)-O-acetyl-L-mandelic acid in 1.8 mL dichloromethane was added 66 mg (0.34 mmol) 1-(3-dimethylaminopropyl)-3-ethylcarbodiimide hydrochloride. The mixture was stirred at 0° C. for 30 minutes. The solution was washed once with a saturated NaHCO₃ solution and once with water. The washings were extracted once with dichloromethane. The combined organic layers were dried over Na₂SO₄, filtered and concentrated in vacuo. The crude oil was purified with flash column chromatography on silica eluting with a gradient formed from heptane and ethylacetate to provide 0.12 g (81%) of the title compound as a colorless oil. MS (m/e): 471.2 [M+H]⁺.

b) Step 2:

(S)—N-(3,4-Dimethyl-phenyl)-2-hydroxy-2-phenyl-N-[2-(5-trifluoromethyl-pyridin-2-yl)-ethyl]-acetamide To a solution of 116 mg (0.25 mmol) acetic acid (S)-{(3,4-dimethyl-phenyl)-[2-(5-trifluoromethyl-pyridin-2-yl)-ethyl]-carbamoyl}-phenyl-methyl ester in 1.2 mL tetrahydrofuran were added 0.6 mL water and 11.4 mg (0.27 mmol) lithium hydroxide monohydrate. The mixture was stirred at room temperature overnight. The mixture was diluted with water and extracted 3 times with ethyl acetate. The combined organic layers were dried over Na₂SO₄, filtered and concentrated in vacuo. The crude oil was purified with flash column chromatography on silica eluting with a gradient formed from heptane and ethylacetate to provide 0.098 g (93%) of the title compound as a colorless oil. MS(m/e): 429.2 [M+H]⁺.

EXAMPLE 27

(R,S)—N-(3,4-Dimethyl-phenyl)-2-hydroxy-2-phenyl-N-[2-(6-trifluoromethyl-pyridin-3-yl)-ethyl]-propionamide

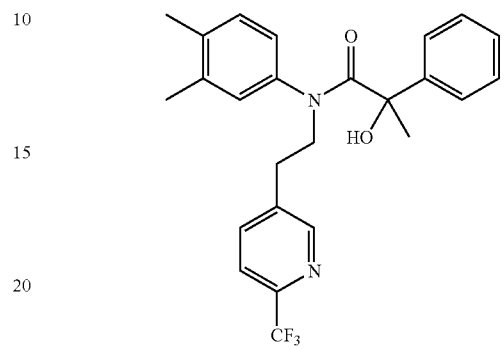

To a solution of N-(3,4-dimethyl-phenyl)-2-oxo-2-phenyl-N-[2-(6-trifluoromethyl-pyridin-3-yl)-ethyl]-acetamide (example 20, 110 mg, 0.26 mmol) in diethylether (2 mL) was added dropwise at 0° C. methylmagnesium bromide (3 M in diethylether, 130 µl, 0.39 mmol). The ice bath was removed and stirring was continued for 1.5 h at ambient temperature. After diluting with TBME (15 mL) aqueous ammonium chloride (20% (w/w), 5 mL) was added and the organig layer separated and washed with brine (15 mL). The aqueous layers were extracted with TBME (15 mL) and the combined organic layers were dried over sodium sulfate.

Concentration and purification by chromatography (SiO₂, heptane:ethyl acetate=95:5 to 60:40) afforded the title compound (111 mg, 97%) as a light brown oil. MS m/e: 443.5 [M+H]⁺.

EXAMPLE 28

(R,S)-2-Cyclopropylamino-2-phenyl-N-(5,6,7,8-tetrahydro-naphthalen-2-yl)-N-[2-(6-trifluoromethyl-pyridin-3-yl)-ethyl]-acetamide

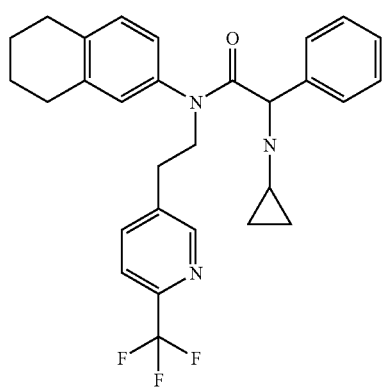

a) Step 1:

(R,S)-Methanesulfonic acid phenyl-{(5,6,7,8-tetrahydro-naphthalen-2-yl)-[2-(6-trifluoromethyl-pyridin-3-yl)-ethyl]-carbamoyl}-methyl ester

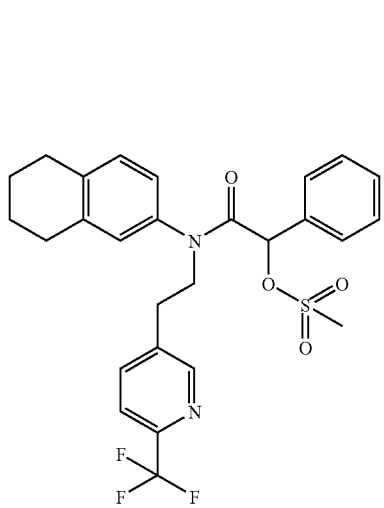

To a solution of 420 mg (0.92 mmol) (R,S)-2-hydroxy-2-phenyl-N-(5,6,7,8-tetrahydro-naphthalen-2-yl)-N-[2-(6-trifluoromethyl-pyridin-3-yl)-ethyl]-acetamide (example 12, step 2) in 4.2 mL dichloromethane containing 12 mg (0.093 mmol) DMAP and 0.19 mL (1.4 mmol) triethylamine was added dropwise a solution of 252 mg (1.4 mmol) methanesulfonic anhydride in 1.43 mL dichloromethane at room temperature. The mixture was stirred for 4 hours. The solution was washed once with water, dried over Na$_2$SO$_4$, filtered and concentrated in vacuo. The crude oil was purified with flash column chromatography on silica eluting with a gradient formed from heptane and ethylacetate to provide 0.43 g (87%) of the title compound as a colorless oil. MS (m/e): 533.2 [M+H]$^+$.

b) Step 2:

(R,S)-2-Cyclopropylamino-2-phenyl-N-(5,6,7,8-tetrahydro-naphthalen-2-yl)-N-[2-(6-trifluoromethyl-pyridin-3-yl)-ethyl]-acetamide To a solution of 50 mg (0.09 mmol) (R,S)-methanesulfonic acid phenyl-{(5,6,7,8-tetrahydro-naphthalen-2-yl)-[2-(6-trifluoromethyl-pyridin-3-yl)-ethyl]-carbamoyl}-methyl ester in 1 mL DMF was added 7.1 mg (0.019 mmol) tetrabutylammonium iodide and finally 0.055 mL (0.94 mmol) cyclopropylamine. The mixture was stirred at 100° C. for 15 minutes under MW irradiation. The mixture was diluted with water and extracted 3 times with ethyl acetate. The combined organic layer was dried over Na$_2$SO$_4$, filtered and concentrated in vacuo. The crude oil was purified with flash column chromatography on silica eluting with a gradient formed from heptane and ethylacetate to provide 9 mg (19%) of the title compound as a colorless oil. MS (m/e): 494.2 [M+H]$^+$.

EXAMPLE 29

(R,S)-2-Cyclobutylamino-2-phenyl-N-(5,6,7,8-tetrahydro-naphthalen-2-yl)-N-[2-(6-trifluoromethyl-pyridin-3-yl)-ethyl]-acetamide

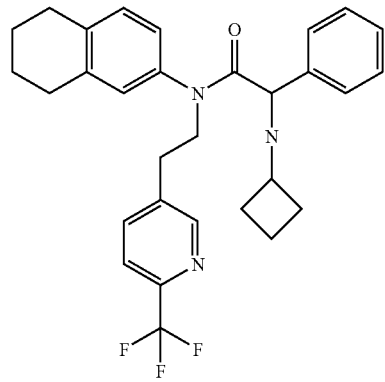

In analogy to the procedure described for the synthesis example 28, step 2, the title compound was prepared from (R,S)-methanesulfonic acid phenyl-{(5,6,7,8-tetrahydro-naphthalen-2-yl)-[2-(6-trifluoromethyl-pyridin-3-yl)-ethyl]-carbamoyl}-methyl ester and cyclobutylamine. MS (m/e): 508.3 [M+H]$^+$.

EXAMPLE 30

N-(3,4-Dimethyl-phenyl)-2-(2-methyl-benzoimidazol-1-yl)-N-[2-(6-trifluoromethyl-pyridin-3-yl)-ethyl]-acetamide

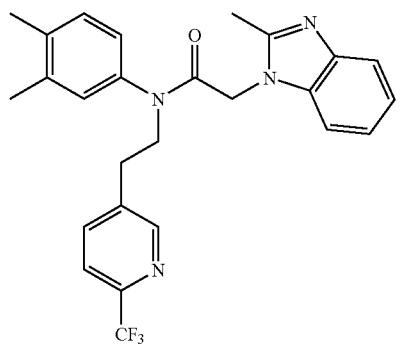

a) Step 1:

2-Bromo-N-(3,4-dimethyl-phenyl)-N-[2-(6-trifluoromethyl-pyridin-3-yl)-ethyl]-acetamide

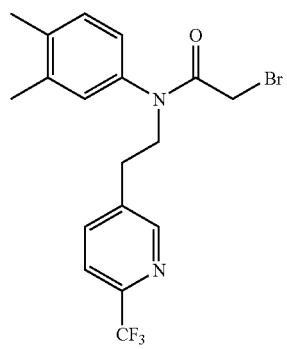

A solution of (3,4-dimethyl-phenyl)-[2-(6-trifluoromethyl-pyridin-3-yl)-ethyl]-amine (220 mg, 0.75 mmol) in diethylether (2 mL) was cooled to 0° C. and triethylamine (114 μL, 0.82 mmol) and bromoacetyl chloride (81 μL, 0.97 mmol) were added. After stirring for 15 min. at this temperature the ice bath was removed and the suspension was stirred for 2 h at ambient temperature. Further bromoacetyl chloride (16 μL, 0.2 mmol) was added and the resulting suspension was stirred for 1 h at this temperature. It was diluted with TBME (10 mL) and washed with water (15 mL) and brine (15 mL). The combined aqueous layers were extracted with TBME (15 mL) and the combined organic layers dried over sodium sulfate. Concentration and purification by chromatography (SiO$_2$, heptane:ethyl acetate=95:5 to 70:30) afforded the title compound (134 mg, 43%) as a light brown oil. MS m/e: 417.1 [M+H]$^+$.

b) Step 2:

N-(3,4-Dimethyl-phenyl)-2-(2-methyl-benzoimidazol-1-yl)-N-[2-(6-trifluoromethyl-pyridin-3-yl)-ethyl]-acetamide A suspension of 2-bromo-N-(3,4-dimethyl-phenyl)-N-[2-(6-trifluoromethyl-pyridin-3-yl)-ethyl]-acetamide (134 mg, 0.32 mmol), 2-methylbenzimidazole (85 mg, 0.65 mmol) and potassium carbonate (67 mg, 0.48 mmol) in acetonitrile (1 mL) was irradiated in the microwave for 20 min. at 140° C. The reaction mixture was diluted with TBME (15 mL) and washed with water (15 mL) and brine (15 mL). The aqueous layers were extracted with tert-butylmethylether (15 mL) and the combined organic layers dried over sodium sulfate. Concentration and purification by chromatography (SiO$_2$, heptane:ethyl acetate:methanol=50:50:0 to 0:95:5) afforded the title compound (86 mg, 57%) as a light brown oil. MS m/e: 467.0 [M+H]$^+$.

EXAMPLE 31

(R,S)-2-Amino-2-(4-chloro-phenyl)-N-(5-methylthiazol-2-yl)-N-(2-p-tolyl-ethyl)-acetamide hydrochloride

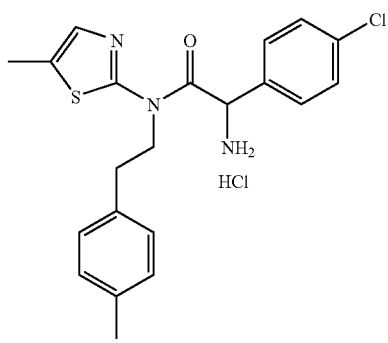

a) Step 1:

N-(5-Methyl-thiazol-2-yl)-2-p-tolyl-acetamide

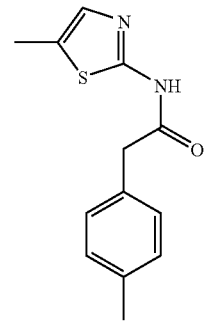

To a suspension of p-tolylacetic acid (1.00 g, 6.66 mmol) and 2-amino-5-methylthiazole (0.760 g, 6.66 mmol) in dichloromethane (10 mL) was added at 0° C. under a nitrogen atmosphere 1-(3-dimethylaminopropyl)-3-ethylcarbodiimide hydrochloride (1.40 g, 7.32 mmol), 1-hydroxybenzotriazole (90 mg, 0.67 mmol) and N,N-diisopropyl ethyl amine (1.8 mL, 10 mmol). The ice bath was removed and the resulting solution was stirred for 3 h at ambient temperature. The reaction mixture was diluted with dichloromethane (20 mL) and washed with aqueous sodium carbonate (half-concentrated, 20 mL) and water (20 mL). The aqueous layers were extracted with dichloromethane (20 mL) and the combined organic layers were dried over sodium sulfate. The filtrate was concentrated and the residue was suspended in TBME (20 mL) and filtered. Washing with TBME (10 mL) afforded the title compound (1.48 g, 90%) as a white solid. MS m/e: 247.2 [M+H]$^+$.

b) Step 2:

(5-Methyl-thiazol-2-yl)-(2-p-tolyl-ethyl)-amine

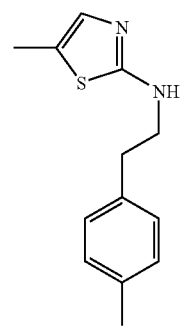

To a suspension of N-(5-methyl-thiazol-2-yl)-2-p-tolylacetamide (1.31 g, 5.33 mmol) in THF (11 mL) was added dropwise under a nitrogen atmosphere borane-tetrahydrofuran complex (1 M in THF, 11 mL, 11 mmol). The reaction mixture was stirred for 18 h at 80° C. To the solution was added very carefully a aqueous hydrochloric acid (1 M, 10 mL) and stirred for 30 min at 80° C. After cooling it was diluted with TBME (25 mL), water (20 mL) and basified by addition of Na$_2$CO$_3$. The aqueous layer was extracted with TBME (25 mL) and the organic layers were washed with brine (15 mL). The combined organic layers were dried over sodium sulfate. Concentration and purification by chromatography (SiO$_2$, heptane:ethyl acetate:methanol=90:10:0 to 40:50:10) afforded the title compound (630 mg, 51%) as a white solid. MS m/e: 233.0 [M+H]$^+$.

c) Step 3:

(R,S)-{(4-Chloro-phenyl)-[(5-methyl-thiazol-2-yl)-(2-p-tolyl-ethyl)-carbamoyl]-methyl}-carbamic acid tert-butyl ester

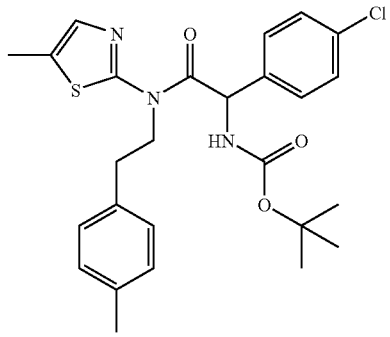

To a solution of (5-methyl-thiazol-2-yl)-(2-p-tolyl-ethyl)-amine (370 mg, 1.59 mmol) in THF (4 mL) was added under a nitrogen atmosphere N-BOC-(4'-chlorophenyl)glycine (478 mg, 1.67 mmol), N,N-diisopropyl ethyl amine (545 μl, 3.18 mmol) and benzotriazol-1-yloxytris(dimethylamino)phosphonium hexafluorophosphate (845 mg, 1.91 mmol). The solution was stirred for 4 h at ambient temperature. It was diluted with TBME (20 mL) and washed with aqueous sodium carbonate (half concentrated, 20 mL), water (20 mL) and brine (20 mL). The aqueous layers were extracted with TBME (20 mL) and the combined organic layers were dried over sodium sulfate. Concentration and purification by chromatography (SiO$_2$, heptane:ethyl acetate=100:0 to 30:70) afforded the title compound (744 mg, 93%) as a light brown liquid. MS m/e: 500.0 [M+H]$^+$.

d) Step 4:

(R,S)-2-Amino-2-(4-chloro-phenyl)-N-(5-methyl-thiazol-2-yl)-N-(2-p-tolyl-ethyl)-acetamide hydrochloride To a solution of (R,S)-{(4-Chloro-phenyl)-[(5-methyl-thiazol-2-yl)-(2-p-tolyl-ethyl)-carbamoyl]-methyl}-carbamic acid tert-butyl ester (701 mg, 1.40 mmol) in TBME (5 mL) was added at ambient temperature hydrochloric acid (4 M in dioxane, 4.2 mL, 17 mmol) and stirred for 2 h at this temperature before heating at 50° C. for 4 h. The resulting white suspension was filtered and washed with TBME (5 mL) affording the title compound (506 mg, 83%) as a white solid. MS m/e: 398.1 [M−H]$^−$.

EXAMPLE 32

(R,S)-2-Amino-2-(4-chloro-phenyl)-N-(2,4-dimethyl-thiazol-5-yl)-N-(2-p-tolyl-ethyl)-acetamide

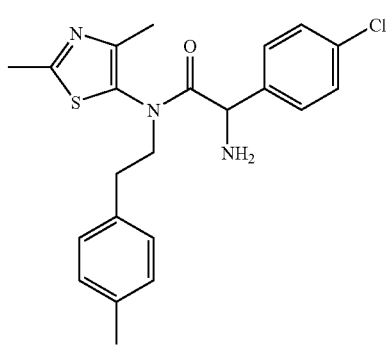

a) Step 1:

(2,4-Dimethyl-thiazol-5-yl)-(2-p-tolyl-ethyl)-amine

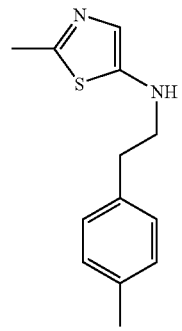

To a solution of 5-bromo-2,4-dimethyl-1,3thiazole (1.00 g, 5.21 mmol) in DMSO (5 mL) was added 2-(p-tolyl)ethylamine (1.06 g, 7.81 mmol) and potassium carbonate (1.1 g, 7.9 mmol). The reaction mixture was stirred for 6 d at ambient temperature and for 2 d at 160° C. under a nitrogen atmosphere. After cooling to ambient temperature it was diluted with ethyl acetate (20 mL) and washed with aqueous sodium carbonate (saturated, 20 mL) and water (20 mL). Drying over sodium sulfate, concentration and purification by chromatography (SiO$_2$, heptane:ethyl acetate=70:30 to 0:100) afforded the title compound (170 mg, 13%) as a light brown solid. MS m/e: 247.0 [M+H]$^+$.

b) Step 2:

(R,S)-{(4-Chloro-phenyl)-[(2,4-dimethyl-thiazol-5-yl)-(2-p-tolyl-ethyl)-carbamoyl]-methyl}-carbamic acid tert-butyl ester

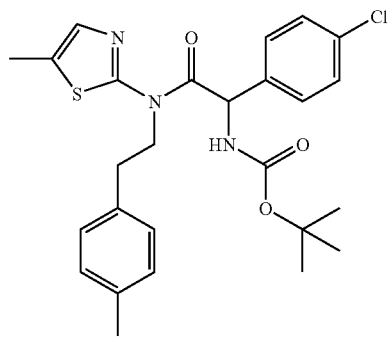

To a solution of N-BOC-(4'-chlorophenyl)glycine (286 mg, 0.87 mmol) in THF (3 mL) was added 1,1'-carbonyldiimidazole (136 mg, 0.84 mmol) and stirred for 2 h at ambient temperature. After the addition of a solution of (2,4-dimethyl-thiazol-5-yl)-(2-p-tolyl-ethyl)-amine (165 mg, 0.67 mmol) in THF (1 mL) the reaction mixture was stirred for 18 h at 60° C. After cooling to ambient temperature it was diluted with ethl acetate (10 mL) and washed with aqueous sodium carbonate (saturated, 15 mL), water (15 mL) and brine (15 mL). The combined aqueous layers were extracted with ethyl acetate (15 mL) and the combined organic layers were dried over sodium sulfate. Concentration and purification by chromatography (SiO$_2$, heptane:ethyl acetate=95:5 to 30:70) afforded the title compound (158 mg, 46%) as a light brown oil. MS m/e: 514.0 [M+H]$^+$.

c) Step 3:

(R,S)-2-Amino-2-(4-chloro-phenyl)-N-(2,4-dimethyl-thiazol-5-yl)-N-(2-p-tolyl-ethyl)-acetamide To a solution of (R,S)-{(4-chloro-phenyl)-[(2,4-dimethyl-thiazol-5-yl)-(2-p-tolyl-ethyl)-carbamoyl]-methyl}-carbamic acid tert-butyl ester (150 mg, 0.29 mmol) in TBME (1.5 mL) was added hydrochloric acid (4 M in dioxane, 875 µl, 3.50 mmol) and stirred for 4 h at 50° C. After cooling to ambient temperature it was diluted with ethyl acetate (15 mL) and washed with aqueous sodium carbonate (saturated, 15 mL). The aqueous layer was extracted with ethyl acetate (15 mL) and the combined organic layers were dried over sodium sulfate. Concentration and purification by chromatography (SiO$_2$, heptane:ethyl acetate=80:20 to 0:100) afforded the title compound (68 mg, 56%) as a light brown oil. MS m/e: 414.4 [M+H]$^+$.

EXAMPLE 33

(R,S)-2-Amino-2-(2-methoxy-phenyl)-N-(6-methoxy-pyridin-3-yl)-N-[2-(4-trifluoromethyl-phenyl)-ethyl]-acetamide

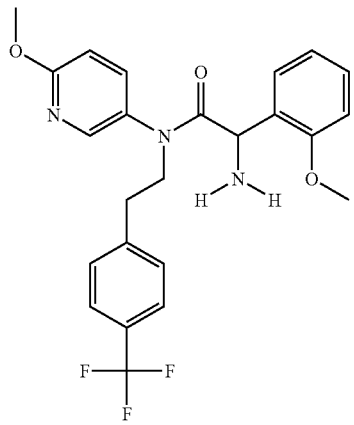

a) Step 1:

(6-Methoxy-pyridin-3-yl)-[2-(4-trifluoromethyl-phenyl)-ethyl]-amine

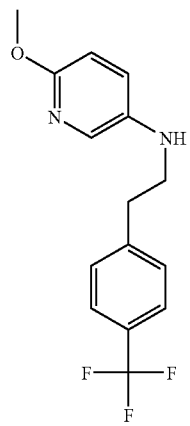

To a suspension of (4-trifluoromethyl-phenyl)-acetic acid (100 mg, commercially available), 6-methoxy-pyridin-3-ylamine (1.1 eq., commercially available) and 1-hydroxybenzotriazole (1.1 eq) in dichloromethane (2 mL) was added under a nitrogen atmosphere 1-(3-dimethylaminopropyl)-3-ethylcarbodiimide hydrochloride (1.1 eq) and N,N-diisopropyl ethyl amine (1.2 eq.). After stirring for 3 h at ambient temperature, the reaction mixture was concentrated and a solution of borane-tetrahydrofuran complex (1 M in THF, 3 eq.) was added and the reaction mixture was stirred for 18 h at 60° C. A further portion of the borane-tetrahydrofuran complex (1 M in THF, 3 eq.,) was added and the reaction mixture was stirred for 4 h at 80° C. An aqueous solution of hydrochloric acid (1 M, 2 mL) was carefully added and stirring was continued for 15 min. at reflux. After cooling it was diluted with ethyl acetate (15 mL) and washed with aqueous Na$_2$CO$_3$ (saturated, 15 mL). The aqueous layer was extracted with EtOAc (15 mL) and the combined organic layers dried over sodium sulfate. Concentration and purification by chromatography (SiO$_2$, heptane:ethyl acetate=95:5 to 60:40) afforded the title compound. MS m/e: 297.0 [M+H]$^+$.

b) Step 2:

(R,S)-2-Amino-2-(2-methoxy-phenyl)-N-(6-methoxy-pyridin-3-yl)-N-[2-(4-trifluoromethyl-phenyl)-ethyl]-acetamide A solution of (6-methoxy-pyridin-3-yl)-[2-(4-trifluoromethyl-phenyl)-ethyl]-amine (50 mg, 0.17 mmol) and HATU (2-(7-aza-1H-benzotriazole-1-yl)-1,1,3,3-tetramethyluronium hexafluorophosphate) (1.05 eq.,) in dry DMF (2 mL) was treated with tert-butoxy-carbonylamino-(2-methoxy-phenyl)-acetic acid (1.05 eq., commercially available) and the mixture stirred at 80° C. for 12 h. The mixture was then concentrated, re-dissolved in CH$_2$Cl$_2$ (2 mL treated with TFA (10 eq.,) and stirring continued for 3 h at ambient temperature. After washing with aqueous Na$_2$CO$_3$ (saturated, 1.5 mL) and water (1.5 mL), the combined aqueous layers were extracted with CH$_2$Cl$_2$ (3×1.5 mL) and the combined organic layers dried over sodium sulfate. Concentration and purification by HPLC provided the title compound as a racemate. MS m/e: 460.2 [M+H]$^+$.

EXAMPLE 34

2-(2-Methoxy-phenyl)-N-(6-methoxy-pyridin-3-yl)-N-[2-(4-trifluoromethyl-phenyl)-ethyl]-acetamide

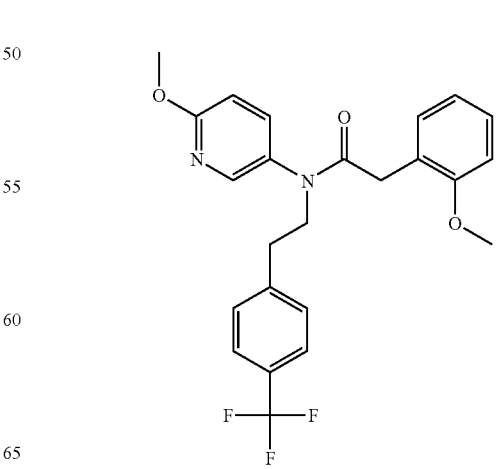

In analogy to example 33, step 2, without TFA addition, (6-methoxy-pyridin-3-yl)-[2-(4-trifluoromethyl-phenyl)-ethyl]-amine, prepared in example 33, step 1) was coupled to (2-methoxy-phenyl)-acetic acid (commercially available) to give the title compound. MS m/e: 445.3 [M+H]$^+$.

EXAMPLE 35

N-Benzothiazol-6-yl-2-(2-methoxy-phenyl)-N-[2-(4-trifluoromethyl-phenyl)-ethyl]-acetamide

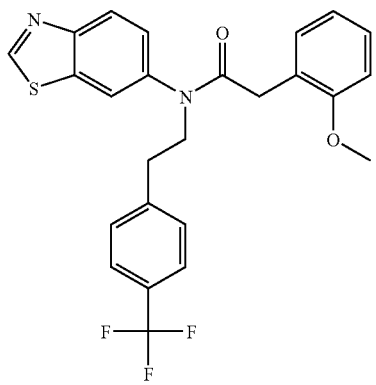

a) Step 1:

Benzothiazol-6-yl-[2-(4-trifluoromethyl-phenyl)-ethyl]-amine:

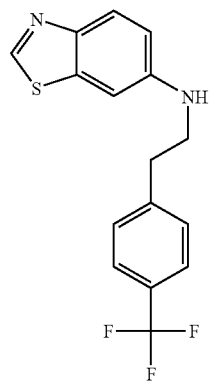

In analogy to example 33, step 1, (4-trifluoromethyl-phenyl)-acetic acid (commercially available) was coupled with benzothiazol-6-ylamine (commercially available) to give the title compound.

b) Step 2:

N-Benzothiazol-6-yl-2-(2-methoxy-phenyl)-N-[2-(4-trifluoromethyl-phenyl)-ethyl]-acetamide In analogy to example 33, step 2, without TFA addition, benzothiazol-6-yl-[2-(4-trifluoromethyl-phenyl)-ethyl]-amine was coupled to (2-methoxy-phenyl)-acetic acid (commercially available) to provide the title compound. MS m/e: 471.0 [M+H]$^+$.

EXAMPLE 36

(R,S)-2-Amino-N-(6-methoxy-pyridin-3-yl)-2-phenyl-N-[2-(4-trifluoromethyl-phenyl)-ethyl]-acetamide

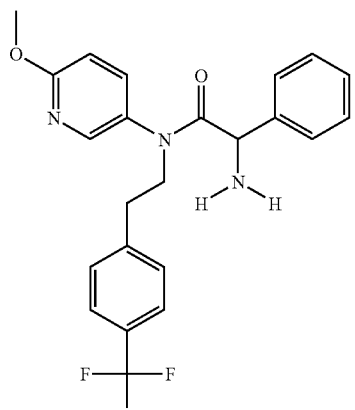

A solution of (6-methoxy-pyridin-3-yl)-[2-(4-trifluoromethyl-phenyl)-ethyl]-amine (52 mg, 0.18 mmol) as per example 33, step 1) and tert-butoxycarbonylamino-phenyl-acetic acid (1 eq., commercially available) in EtOAc (1 mL) at 0° C. was treated with 2-chloro-4,6-dimethoxy-1,3,5-triazine (1.1 eq.,), and N-methylmorpholine (1.5 eq.,). After stirring for 15 min at ambient temperature, a solution of TFA (15 mmol) in CH$_2$Cl$_2$ (2 mL) was added and the mixture stirred for 4 h. After filtration and concentration, the residue was diluted with EtOAc (15 mL) then washed with saturated aq, NaHCO$_3$ (3×10 mL), H$_2$O (2×15 mL) and dried over Na$_2$SO$_4$, filtered, concentrated and purified by to provide the racemic title compound. MS m/e: 430.3 [M+H]$^+$.

EXAMPLE 37

(R,S)-2-Amino-2-phenyl-N-[2-(4-trifluoromethyl-phenyl)-ethyl]-N-(6-trifluoromethyl-pyridin-3-yl)-acetamide

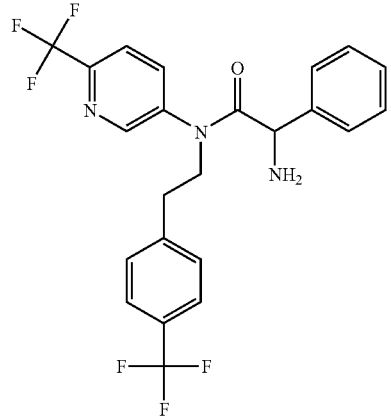

a) Step 1:

[2-(4-Trifluoromethyl-phenyl)-ethyl]-(6-trifluoromethyl-pyridin-3-yl)-amine

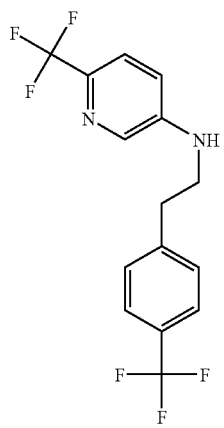

In analogy to example 33, step 1, (4-trifluoromethyl-phenyl)-acetic acid (commercially available) was coupled with 6-trifluoromethyl-pyridin-3-ylamine (commercially available) to give the title compound MS m/e: 335.1 [M+H]$^+$.

b) Step 2:

2-Oxo-2-phenyl-N-[2-(4-trifluoromethyl-phenyl)-ethyl]-N-(6-trifluoromethyl-pyridin-3-yl)-acetamide

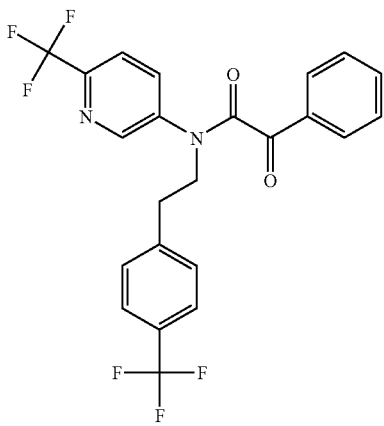

To a solution of [2-(4-trifluoromethyl-phenyl)-ethyl]-(6-trifluoromethyl-pyridin-3-yl)-amine (50 mg) in CH$_2$Cl$_2$ (3 mL) was added under a nitrogen atmosphere at 0° C. benzoyl formic acid (1.1 eq., commercially available) and EDC (1.1 eq). After stirring for 12 h a ambient temperature, the mixture was washed with aqueous Na$_2$CO$_3$ (saturated, 2.5 mL) and water (2.5 mL), the combined aqueous layers were extracted with CH$_2$Cl$_2$ (3×2.5 mL) and the combined organic layers dried over sodium sulfate. Concentration and purification by chromatography (SiO$_2$, heptane:ethyl acetate=95:5 to 60:40) afforded the title compound (46 mg, 66%) as a light yellow solid. MS m/e: 467.2 [M+H]$^+$.

c) Step 3:

2-Hydroxyimino-2-phenyl-N-[2-(4-trifluoromethyl-phenyl)-ethyl]-N-(6-trifluoromethyl-pyridin-3-yl)-acetamide

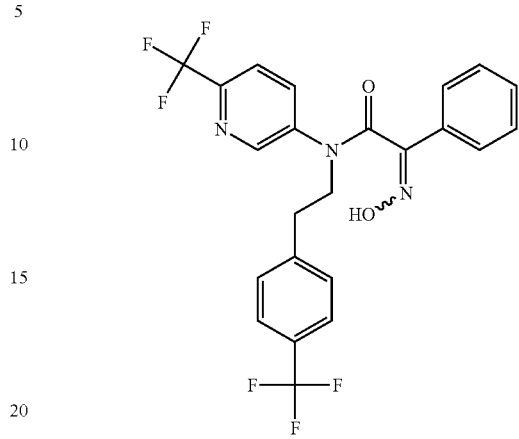

To a solution of 2-oxo-2-phenyl-N-[2-(4-trifluoromethyl-phenyl)-ethyl]-N-(6-trifluoromethyl-pyridin-3-yl)-acetamide (46 mg, 0.1 mmol) in EtOH (2 mL) was added hydroxylamine hydrochloride (14 mg, 0.2 mmol) and 2,6-lutidine (32 mg, 0.3 mmol) and the mixture stirred at ambient temperature for 36 h then concentrated and redissolved in EtOAc (5 mL), washed with 10% aqueous citric acid (3×5 mL), dried over Na$_2$SO$_4$, filtered, then purified by chromatography (SiO$_2$, heptane:ethyl acetate=95:5 to 50:50) to afford the title compound (22 mg, 46%) as a white solid. MS m/e: 480.3 [M+H]$^+$.

d) Step 4:

(R,S)-2-Amino-2-phenyl-N-[2-(4-trifluoromethyl-phenyl)-ethyl]-N-(6-trifluoromethyl-pyridin-3-yl)-acetamide A solution of 2-hydroxyimino-2-phenyl-N-[2-(4-trifluoromethyl-phenyl)-ethyl]-N-(6-trifluoromethyl-pyridin-3-yl)-acetamide (22 mg, 0.046 mmol) in EtOH (2 mL) was treated with 10% Pd/C (5 mg) and TFA (10 mg) and the mixture stirred for 12 h under a hydrogen atmosphere. Exchanging the hydrogen for argon, the mixture was filtered and diluted with EtOAc (15 mL) then washed with saturated aq, NaHCO$_3$ (3×10 mL), H$_2$O (2×15 mL) and dried over Na$_2$SO$_4$, filtered, concentrated, then purified by chromatography (SiO$_2$, heptane:ethyl acetate=95:5 to 5:95) to afford the title compound (10 mg, 47%) as a colourless oil. MS m/e: 468.3 [M+H]$^+$.

EXAMPLE 38

(R,S)-2-Amino-N-(2-methoxy-pyridin-3-yl)-2-phenyl-N-[2-(4-trifluoromethyl-phenyl)-ethyl]-acetamide

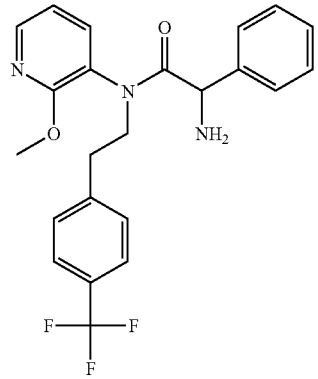

a) Step 1:

(2-Methoxy-pyridin-3-yl)-[2-(4-trifluoromethyl-phenyl)-ethyl]-amine

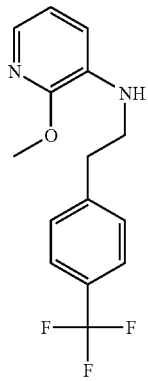

In analogy to example 33, step 1, (4-trifluoromethyl-phenyl)-acetic acid (commercially available) was coupled with 2-methoxy-pyridin-3-ylamine (commercially available) to give the title compound.

b) Step 2:

(R,S)-2-Amino-N-(2-methoxy-pyridin-3-yl)-2-phenyl-N-[2-(4-trifluoromethyl-phenyl)-ethyl]-acetamide A solution of tert-butoxycarbonylamino-phenyl-acetic acid (251 mg, 1 mmol, commercially available) in EtOAc (3 mL) was treated with (2-methoxy-pyridin-3-yl)-[2-(4-trifluoromethyl-phenyl)-ethyl]-amine (296 mg, 1 mmol), 2-chloro-4,6-dimethoxy-1,3,5-triazine (184 mg, 1.1 mmol), and N-methylmorpholine (152 mg, 1.5 mmol) at ambient temperature. After stirring for 15 min, a solution of TFA (15 mmol) in $CH_2Cl_2$ (2 mL) was added and the mixture stirred for 4 h. After filtration and concentration, the residue was diluted with EtOAc (15 mL) then washed with saturated aqueous $NaHCO_3$ (3×10 mL), $H_2O$ (2×15 mL) and dried over $Na_2SO_4$, filtered, concentrated and purified by chromatography ($SiO_2$, $CH_2Cl_2$:MeOH=100:0 to 90:10) to afford the title compound (33 mg, 77%) as a yellow viscous oil. MS m/e: 430.3 $[M+H]^+$.

EXAMPLE 39

(R,S)-2-Amino-2-(4-chloro-phenyl)-N-(2,5-dimethyl-2H-pyrazol-3-yl)-N-[2-(4-trifluoromethyl-phenyl)-ethyl]-acetamide

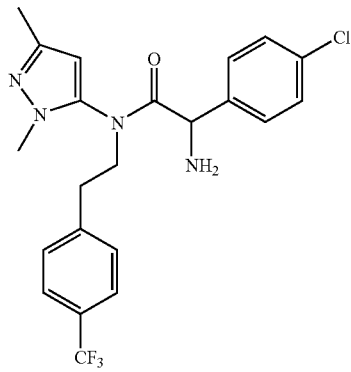

a) Step 1:

(R,S)-[(4-Chloro-phenyl)-(2,5-dimethyl-2H-pyrazol-3-ylcarbamoyl)-methyl]-carbamic acid tert-butyl ester To a solution of 5-amino-1,3-dimethylpyrazole (300 mg, 2.70 mmol) in dichloromethane (3 mL) was added at ambient temperature under a nitrogen atmosphere N-BOC-(4'-chlorophenyl)glycine (771 mg, 2.70 mmol), 1-(3-dimethylaminopropyl)-3-ethylcarbodiimide hydrochloride (569 mg, 2.97 mmol), 1-hydroxybenzotriazole (36 mg, 0.27 mmol) and N,N-diisopropyl ethyl amine (693 µl, 4.05 mmol). The resulting reaction mixture was was stirred for 18 h at this temperature. The solution was diluted with ethyl acetate (20 mL) and washed with aqueous sodium carbonate (half saturated, 20 mL), water (20 mL) and brine (20 mL). The combined aqueous layers were extracted with ethyl acetate (20 mL) and the combined organic layers were dried over sodium sulfate. Concentration and purification by chromatography ($SiO_2$, heptane:ethyl acetate=80:20 to 0:100) afforded the title compound (656 mg, 64%) as a colorless oil. MS m/e: 379.3 $[M+H]^+$.

b) Step 2:

(R,S)-2-Amino-2-(4-chloro-phenyl)-N-(2,5-dimethyl-2H-pyrazol-3-yl)-N-[2-(4-trifluoromethyl-phenyl)-ethyl]-acetamide To a suspension of (R,S)-[(4-chloro-phenyl)-(2,5-dimethyl-2H-pyrazol-3-ylcarbamoyl)-methyl]-carbamic acid tert-butyl ester (600 mg, 1.58 mmol) and potassium carbonate (1.09 g, 7.91 mmol) in DMF (4 mL) was added under vigorously stirring at 90° C. a solution of 1-(2-bromo-ethyl)-4-trifluoromethyl-benzene (which might be prepared according to WO2005123748, 600 mg, 2.38 mmol) in DMF (2 mL) over a period of 1 h and stirring was continued for further 30 min. at 90° C. Further 1-(2-bromo-ethyl)-4-trifluoromethyl-benzene (600 mg, 2.38 mmol) in DMF (2 mL) was added over a period of 1 h and stirring was continued for further 18 h at 90° C. After cooling to ambient temperature the solution was diluted with ethyl acetate (20 mL) and washed with aqueous sodium carbonate (half saturated, 20 mL) and twice with brine (20 mL). The combined aqueous layers were extracted with ethyl acetate (20 mL) and the combined organic layers were dried over sodium sulfate. The concentrated filtrate was treated with TFA (1 mL, 13 mmol) and stirred for 3 h at ambient temperature. Concentration and purification by chromatography ($SiO_2$, heptane:ethyl acetate:methanol=90:10:0 to 50:45:5) afforded the title compound (43 mg, 6%) as a light brown oil. MS m/e: 451.0 $[M+H]^+$.

EXAMPLE 40

(R)-2-Amino-2-(4-chloro-phenyl)-N-(2,4-dimethyl-thiazol-5-yl)-N-(2-p-tolyl-ethyl)-acetamide

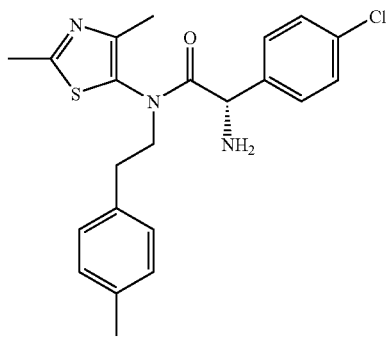

a) Step 1:

(2,4-Dimethyl-thiazol-5-yl)-(2-p-tolyl-ethyl)-amine

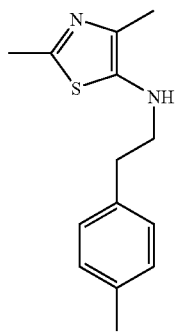

In analogy to the procedure described for the synthesis example 32 (step 1), the title compound (2,4-dimethyl-thiazol-5-yl)-(2-p-tolyl-ethyl)-amine (MS m/e: 247.0 [M+H]$^+$) was prepared from 5-bromo-2,4-dimethyl-1,3thiazole and 2-(p-tolyl)ethylamine.

b) Step 2:

(R,S)-{(4-Chloro-phenyl)-[(2,4-dimethyl-thiazol-5-yl)-(2-p-tolyl-ethyl)-carbamoyl]-methyl}-carbamic acid tert-butyl ester

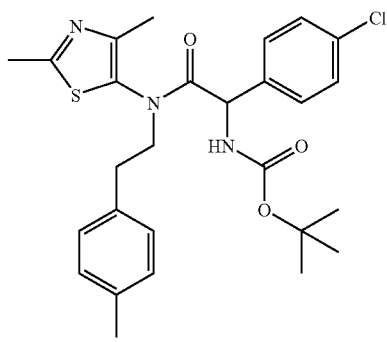

In analogy to the procedure described for the synthesis example 32 (step 2), the title compound (R,S)-{(4-Chloro-phenyl)-[(2,4-dimethyl-thiazol-5-yl)-(2-p-tolyl-ethyl)-carbamoyl]-methyl}-carbamic acid tert-butyl ester (MS m/e: 514.0 [M+H]$^+$) was prepared from (2,4-dimethyl-thiazol-5-yl)-(2-p-tolyl-ethyl)-amine and N-BOC-(4'-chlorophenyl) glycine.

c) Step 3:

(R,S)-2-Amino-2-(4-chloro-phenyl)-N-(2,4-dimethyl-thiazol-5-yl)-N-(2-p-tolyl-ethyl)-acetamide

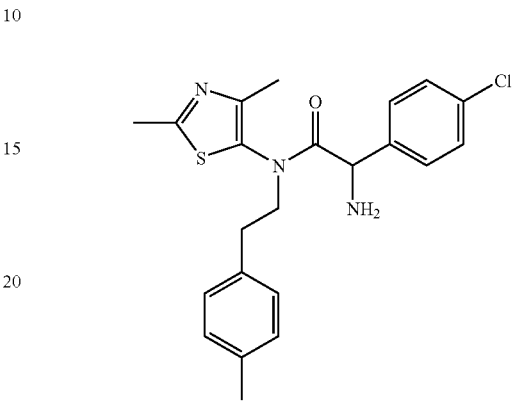

In analogy to the procedure described for the synthesis example 32 (step 3), the title compound (R,S)-2-amino-2-(4-chloro-phenyl)-N-(2,4-dimethyl-thiazol-5-yl)-N-(2-p-tolyl-ethyl)-acetamide (MS m/e: 414.4 [M+H]$^+$) was prepared from (R,S)-{(4-chloro-phenyl)-[(2,4-dimethyl-thiazol-5-yl)-(2-p-tolyl-ethyl)-carbamoyl]-methyl}-carbamic acid tert-butyl ester.

d) Step 4:

(S)-2-Amino-2-(4-chloro-phenyl)-N-(2,4-dimethyl-thiazol-5-yl)-N-(2-p-tolyl-ethyl)-acetamide (R,S)-2-Amino-2-(4-chloro-phenyl)-N-(2,4-dimethyl-thiazol-5-yl)-N-(2-p-tolyl-ethyl)-acetamide was separated on chiral phase HPLC (Chiralpak AD column) to provide the title compound (S)-2-amino-2-(4-chloro-phenyl)-N-(2,4-dimethyl-thiazol-5-yl)-N-(2-p-tolyl-ethyl)-acetamide (MS m/e: 414.2 [M+H]$^+$) as a light brown oil.

EXAMPLE 41

N-(2,5-Dimethyl-2H-pyrazol-3-yl)-2-oxo-2-phenyl-N-[2-(4-trifluoromethyl-phenyl)-ethyl]-acetamide

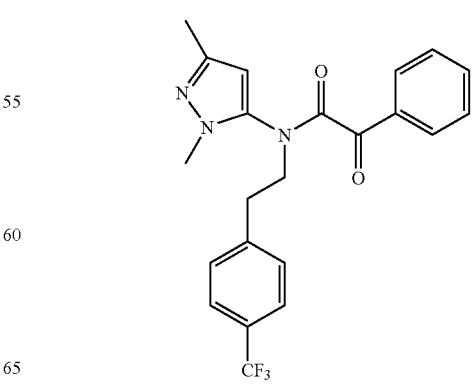

a) Step 1:

N-(2,5-Dimethyl-2H-pyrazol-3-yl)-2-oxo-2-phenyl-acetamide

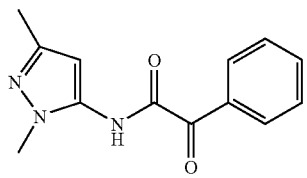

To a solution of 5-amino-1,3-dimethylpyrazole (2.00 g, 18.0 mmol) in THF (20 mL) was added at ambient temperature N,N-diisopropyl ethyl amine (4.62 mL, 27.0 mmol) and over a period of 5 min benzoylformic acid chloride (which might be prepared according to Synlett (11) 1763-1765, 1999, 3.64 g, 21.6 mmol) and the reaction mixture was stirred for 18 h at this temperature. It was diluted with TBME (50 mL) and washed twice with water (50 mL) and brine (50 mL). The combined aqueous layers were extracted with TBME (50 mL) and the combined organic layers were dried over sodium sulfate. Concentration and purification by chromatography (SiO$_2$, heptane:ethyl acetate=50:50 to 0:100) afforded the title compound (2.11 g, 48%) as a light brown oil. MS m/e: 244.3 [M+H]$^+$.

b) Step 2:

N-(2,5-Dimethyl-2H-pyrazol-3-yl)-2-oxo-2-phenyl-N-[2-(4-trifluoromethyl-phenyl)-ethyl]-acetamide To a solution of N-(2,5-dimethyl-2H-pyrazol-3-yl)-2-oxo-2-phenyl-acetamide (200 mg, 0.82 mmol) in DMF (2 mL) was added at 0° C. potassium bis(trimethylsilyl)amide (0.91 M in THF, 1.1 mL, 0.99 mmol) over a period of 5 min. The ice bath was removed and the solution was stirred for 1 h at ambient temperature. After the addition of 1-(2-bromo-ethyl)-4-trifluoromethyl-benzene (which might be prepared according to WO2005123748, 250 mg, 0.99 mmol) the reaction mixture was stirred for 18 h at ambient temperature. After the addition of cesium carbonate (1.40 g, 4.11 mmol) and further 1-(2-bromo-ethyl)-4-trifluoromethyl-benzene (996 mg, 3.95 mmol) it was stirred for 20 h at ambient temperature. The resulting mixture was diluted with TBME (15 mL) and washed twice with water (10 mL) and brine (10 mL). The combined aqueous layers were extracted with TBME (15 mL) and the combined organic layers were dried over sodium sulfate. Concentration and purification by chromatography (SiO$_2$, heptane:ethyl acetate=95:5 to 60:40) afforded the title compound (113 mg, 33%) as a light brown oil. MS m/e: 416.3 [M+H]$^+$.

EXAMPLE 42

(R,S)—N-(2,5-Dimethyl-2H-pyrazol-3-yl)-2-hydroxy-2-phenyl-N-[2-(4-trifluoromethyl-phenyl)-ethyl]-acetamide

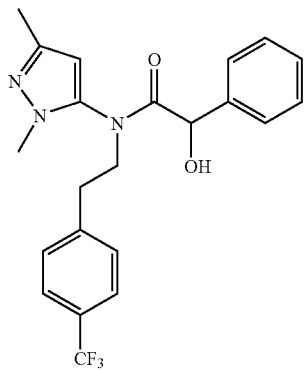

To a solution of N-(2,5-dimethyl-2H-pyrazol-3-yl)-2-oxo-2-phenyl-N-[2-(4-trifluoromethyl-phenyl)-ethyl]-acetamide (example 43, 85 mg, 0.21 mmol) in methanol (1 mL) was added sodium borohydride (12 mg, 0.31 mmol) and stirred for 3 h at ambient temperature. The solution was concentrated in vacuo and purified by chromatography (SiO$_2$, heptane:ethyl acetate=80:20 to 0:100) afforded the title compound (59 mg, 69%) as a light brown oil. MS m/e: 418.3 [M+H]$^+$.

EXAMPLE 43

(R,S)-2-Hydroxy-N-(5-methyl-pyridin-2-yl)-2-phenyl-N-[2-(4-trifluoromethyl-phenyl)-ethyl]-acetamide

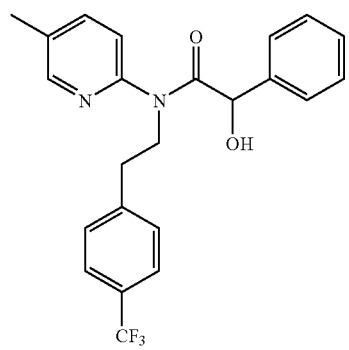

a) Step 1:

N-(6-Chloro-pyridin-3-yl)-2-oxo-2-phenyl-acetamide

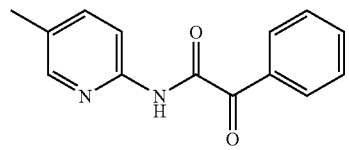

In analogy to the procedure described for the synthesis example 41 (step 1), the title compound N-(6-chloro-pyridin-3-yl)-2-oxo-2-phenyl-acetamide (MS m/e: 241.2 [M+H]$^+$) was prepared from 6-chloro-pyridin-3-ylamine and benzoyl-formic acid chloride.

b) Step 2:

N-(5-Methyl-pyridin-2-yl)-2-oxo-2-phenyl-N-[2-(4-trifluoromethyl-phenyl)-ethyl]-acetamide

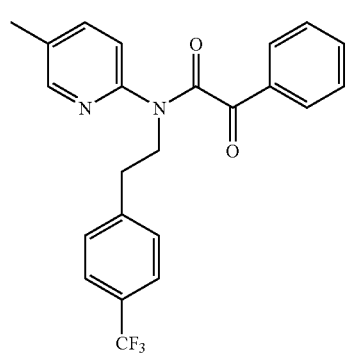

To a suspension of N-(6-chloro-pyridin-3-yl)-2-oxo-2-phenyl-acetamide (0.39 g, 1.64 mmol) and cesium carbonate (2.6 g, 8.2 mmol) in THF (5 mL) was added under a nitrogen atmosphere over a period of 3 h 1-(2-bromo-ethyl)-4-trifluoromethyl-benzene (which might be prepared according to WO2005123748, 1.20 g, 4.9 mmol). The reaction mixture was stirred for 18 h at ambient temperature. Concentration and purification by chromatography (SiO$_2$, heptane:ethyl acetate=50:50 to 30:70) afforded the title compound (120 mg, 18%) as a white solid. MS m/e: 413.1 [M+H]$^+$.

c) Step 3:

(R,S)-2-Hydroxy-N-(5-methyl-pyridin-2-yl)-2-phenyl-N-[2-(4-trifluoromethyl-phenyl)-ethyl]-acetamide In analogy to the procedure described for the synthesis example 42, the title compound (R,S)-2-hydroxy-N-(5-methyl-pyridin-2-yl)-2-phenyl-N-[2-(4-trifluoromethyl-phenyl)-ethyl]-acetamide (MS m/e: 415.3 [M+H]$^+$) was prepared from N-(5-methyl-pyridin-2-yl)-2-oxo-2-phenyl-N-[2-(4-trifluoromethyl-phenyl)-ethyl]-acetamide.

EXAMPLE 44

(R,S)-2-Hydroxy-N-(6-methyl-pyridin-3-yl)-2-phenyl-N-[2-(4-trifluoromethyl-phenyl)-ethyl]-acetamide

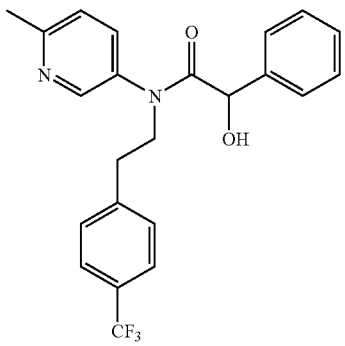

a) Step 1:

N-(6-Methyl-pyridin-3-yl)-2-oxo-2-phenyl-acetamide

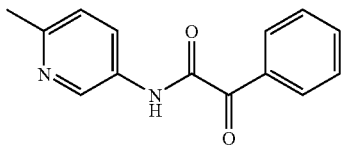

In analogy to the procedure described for the synthesis example 41 (step 1), the title compound N-(6-methyl-pyridin-3-yl)-2-oxo-2-phenyl-acetamide (MS m/e: 241.2 [M+H]$^+$) was prepared from 6-methyl-pyridin-3-ylamine and benzoyl-formic acid chloride.

b) Step 2:

N-(6-Methyl-pyridin-3-yl)-2-oxo-2-phenyl-N-[2-(4-trifluoromethyl-phenyl)-ethyl]-acetamide

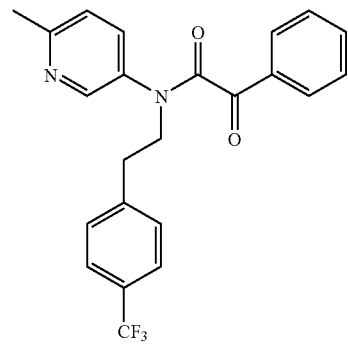

In analogy to the procedure described for the synthesis example 43 (step 2), the title compound N-(6-methyl-pyridin-3-yl)-2-oxo-2-phenyl-N-[2-(4-trifluoromethyl-phenyl)-ethyl]-acetamide (MS m/e: 413.2 [M+H]$^+$) was prepared from N-(6-methyl-pyridin-3-yl)-2-oxo-2-phenyl-acetamide and 1-(2-bromo-ethyl)-4-trifluoromethyl-benzene.

c) Step 3:

(R,S)-2-Hydroxy-N-(6-methyl-pyridin-3-yl)-2-phenyl-N-[2-(4-trifluoromethyl-phenyl)-ethyl]-acetamide In analogy to the procedure described for the synthesis example 42, the title compound (R,S)-2-hydroxy-N-(6-methyl-pyridin-3-yl)-2-phenyl-N-[2-(4-trifluoromethyl-phenyl)-ethyl]-acetamide (MS m/e: 415.2 [M+H]$^+$) was prepared from N-(6-methyl-pyridin-3-yl)-2-oxo-2-phenyl-N-[2-(4-trifluoromethyl-phenyl)-ethyl]-acetamide.

EXAMPLE 45

(R,S)—N-(6-Chloro-pyridin-3-yl)-2-hydroxy-2-phenyl-N-[2-(4-trifluoromethyl-phenyl)-ethyl]-acetamide

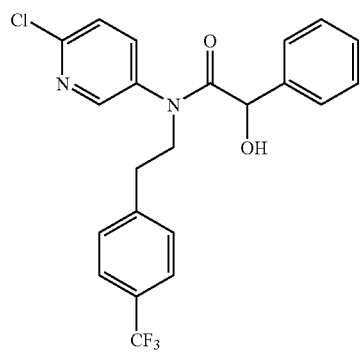

a) Step 1:

N-(6-Chloro-pyridin-3-yl)-2-oxo-2-phenyl-acetamide

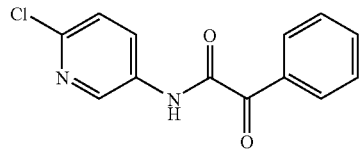

In analogy to the procedure described for the synthesis example 41 (step 1), the title compound N-(6-chloro-pyridin-3-yl)-2-oxo-2-phenyl-acetamide (MS m/e: 261.0 [M+H]$^+$) was prepared from 6-chloro-pyridin-3-ylamine and benzoylformic acid chloride.

b) Step 2:

N-(6-Chloro-pyridin-3-yl)-2-oxo-2-phenyl-N-[2-(4-trifluoromethyl-phenyl)-ethyl]-acetamide

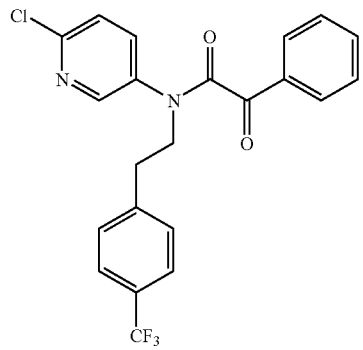

In analogy to the procedure described for the synthesis example 43 (step 2), the title compound N-(6-chloro-pyridin-3-yl)-2-oxo-2-phenyl-N-[2-(4-trifluoromethyl-phenyl)-ethyl]-acetamide (MS m/e: 433.2 [M+H]$^+$) was prepared from N-(6-chloro-pyridin-3-yl)-2-oxo-2-phenyl-acetamide and 1-(2-bromo-ethyl)-4-trifluoromethyl-benzene.

c) Step 3:

(R,S)—N-(6-Chloro-pyridin-3-yl)-2-hydroxy-2-phenyl-N-[2-(4-trifluoromethyl-phenyl)-ethyl]-acetamide In analogy to the procedure described for the synthesis example 42, the title compound (R,S)—N-(6-chloro-pyridin-3-yl)-2-hydroxy-2-phenyl-N-[2-(4-trifluoromethyl-phenyl)-ethyl]-acetamide (MS m/e: 435.2 [M+H]$^+$) was prepared from N-(6-chloro-pyridin-3-yl)-2-oxo-2-phenyl-N-[2-(4-trifluoromethyl-phenyl)-ethyl]-acetamide.

EXAMPLE 46

(R,S)-2-Hydroxy-N-(2-methyl-pyridin-4-yl)-2-phenyl-N-[2-(4-trifluoromethyl-phenyl)-ethyl]-acetamide

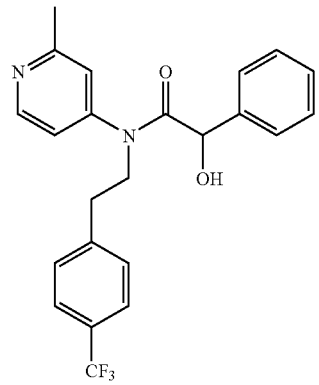

a) Step 1:

N-(2-Methyl-pyridin-4-yl)-2-oxo-2-phenyl-acetamide

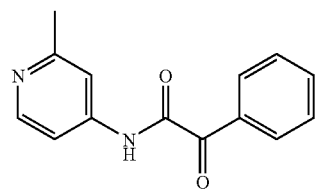

In analogy to the procedure described for the synthesis example 41 (step 1), the title compound N-(2-methyl-pyridin-4-yl)-2-oxo-2-phenyl-acetamide (MS m/e: 241.2 [M+H]$^+$) was prepared from 4-amino-2-picoline and benzoylformic acid chloride.

b) Step 2:

N-(2-Methyl-pyridin-4-yl)-2-oxo-2-phenyl-N-[2-(4-trifluoromethyl-phenyl)-ethyl]-acetamide

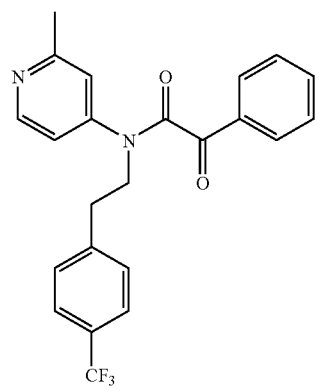

In analogy to the procedure described for the synthesis example 43 (step 2), the title compound N-(2-methyl-pyridin-4-yl)-2-oxo-2-phenyl-N-[2-(4-trifluoromethyl-phenyl)-ethyl]-acetamide (MS m/e: 413.2 [M+H]⁺) was prepared from N-(2-methyl-pyridin-4-yl)-2-oxo-2-phenyl-acetamide and 1-(2-bromo-ethyl)-4-trifluoromethyl-benzene.

c) Step 3:

(R,S)-2-Hydroxy-N-(2-methyl-pyridin-4-yl)-2-phenyl-N-[2-(4-trifluoromethyl-phenyl)-ethyl]-acetamide In analogy to the procedure described for the synthesis example 42, the title compound (R,S)-2-hydroxy-N-(2-methyl-pyridin-4-yl)-2-phenyl-N-[2-(4-trifluoromethyl-phenyl)-ethyl]-acetamide (MS m/e: 415.2 [M+H]⁺) was prepared from N-(2-methyl-pyridin-4-yl)-2-oxo-2-phenyl-N-[2-(4-trifluoromethyl-phenyl)-ethyl]-acetamide.

EXAMPLE 47

(S)—N-(1-Ethyl-3-methyl-1H-pyrazol-4-yl)-2-hydroxy-2-phenyl-N-[2-(6-trifluoromethyl-pyridin-3-yl)-ethyl]-acetamide

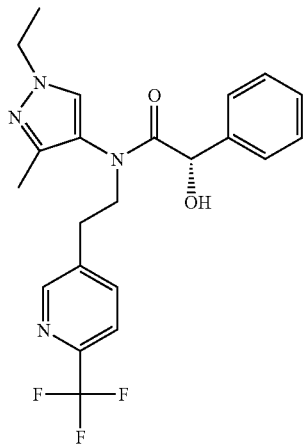

a) Step 1:

(6-Trifluoromethyl-pyridin-3-yl)-acetonitrile

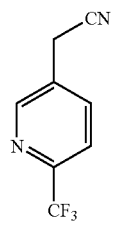

To a solution of (6-trifluoromethyl-pyridin-3-yl)-methanol (4.93 g, 27.8 mmol) in THF (50 mL) were added N,N-diisopropyl ethyl amine (5.7 mL, 33 mmol) and 4-dimethylaminopyridine (17 mg, 0.14 mmol). After cooling to 0° C. thionyl chloride (4.8 mL, 56 mmol) was added dropwise over a period of 10 min. After stirring for 30 min. at 0° C., the ice bath was replaced with a water bath and stirred for 2 h at ambient temperature. The resulting brown reaction mixture was concentrated in vacuo, diluted with TBME (50 mL) and cooled to 0° C. before aqueous NaHCO₃ (1M, 100 mL) was added. The mixture was stirred for 30 min., the aqueous layers were extracted with TBME (50 mL) and the combined organic layers were washed with aqueous NaHCO₃ (1M, 50 mL) and brine (50 mL). Drying over sodium sulphate was followed by concentration. The resulting oil (6.44 g) was dissolved in DMSO (15 mL) and sodium cyanide (1.36 g, 27.8 mmol) was added. The resulting dark reaction mixture was stirred for 18 h at ambient temperature under a nitrogen atmosphere. It was diluted with TBME (50 mL) and treated with ice (30 g) and water (50 mL). The aqueous layer was separated and extracted with TBME (50 mL). The organic layers were washed twice with water (50 mL) and brine (30 mL), dried over sodium sulfate and concentrated. Purification by chromatography (SiO₂, heptane:ethyl acetate=95:5 to 50:50) afforded the title compound (3.59 g, 59%) as a light brown oil. MS m/e: 185.3 [M−H]⁻.

b) Step 2:

(1-Ethyl-3-methyl-1H-pyrazol-4-yl)-[2-(6-trifluoromethyl-pyridin-3-yl)-ethyl]-amine

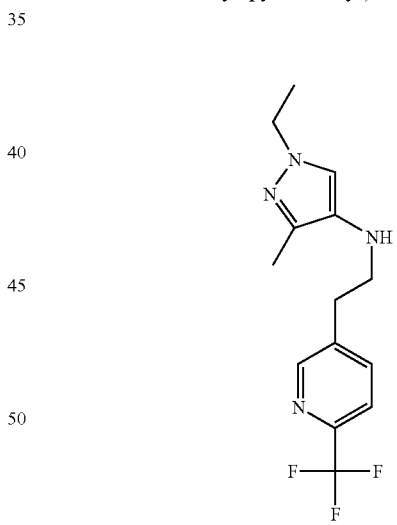

A solution of 1-ethyl-3-methyl-1H-pyrazol-4-ylamine (1.345 g, 10.75 mmol, commercially available) and (6-trifluoromethyl-pyridin-3-yl)-acetonitrile (distilled 166-175° C./2 mb, 1.0 g, 5.4 mmol) in MeOH (10 mL) was treated with HCO₂NH₄ (1.694 g, 26.86 mmol) and 10% Pd/C (200 mg) and stirred at 80° for 1.5 h. Filtration, concentration and purification by HPLC afforded the title compound (0.213 g, 13%) as a light brown oil. MS m/e: 299.3 [M+H]⁺.

c) Step 3:

N-(1-Ethyl-3-methyl-1H-pyrazol-4-yl)-2-oxo-2-phenyl-N-[2-(6-trifluoromethyl-pyridin-3-yl)-ethyl]-acetamide

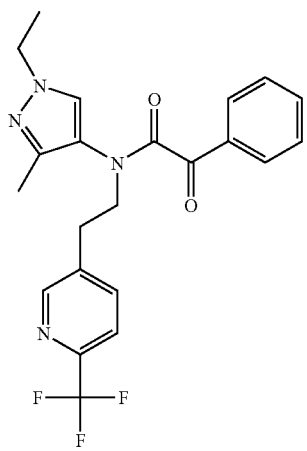

To a solution of (1-ethyl-3-methyl-1H-pyrazol-4-yl)-[2-(6-trifluoromethyl-pyridin-3-yl)-ethyl]-amine (100 mg) in CH$_2$Cl$_2$ (5 mL) was added under a nitrogen atmosphere at 0° C. benzoyl formic acid (1.1 eq., commercially available) and EDC (1.1 eq). After stirring for 12 h a rt, the mixture was washed with aqueous Na$_2$CO$_3$ (saturated, 2.5 mL) and water (2.5 mL), the combined aqueous layers were extracted with CH$_2$Cl$_2$ (3×2.5 mL) and the combined organic layers dried over sodium sulfate. Concentration afforded the title compound (161 mg, >100%) as a light yellow oil which was used without further purification for the next step. MS m/e: 431.2 [M+H]$^+$.

d) Step 4:

(S)—N-(1-Ethyl-3-methyl-1H-pyrazol-4-yl)-2-hydroxy-2-phenyl-N-[2-(6-trifluoromethyl-pyridin-3-yl)-ethyl]-acetamide A solution of N-(1-ethyl-3-methyl-1H-pyrazol-4-yl)-2-oxo-2-phenyl-N-[2-(6-trifluoromethyl-pyridin-3-yl)-ethyl]-acetamide (145 mg, 0.34 mmol) was dissolved in MeOH (4 mL), cooled to 0° C. and treated with NaBH$_4$ (38 mg, 1 mmol) and stirred for 12 h at ambient temperature. The reaction mixture was quenched with aqueous K$_2$CO$_3$ (2 M, 1 mL), concentrated, then redissolved in EtOAc (15 mL) and washed with aqueous K$_2$CO$_3$ (2 M, 3×15 mL). The combined aqueous layers were extracted with EtOAc (3×15 mL) and the combined organic layers dried over sodium sulfate. Concentration afforded the racemic compound (170 mg, >100%) as a light yellow oil. Separation by chromatography on a chiral column provided the title compound as a colourless oil (38 mg, 26%) MS m/e: 433.2 [M+H]$^+$ which crystallized upon standing.

EXAMPLE 48

(S)—N-(1-Ethyl-3-methyl-1H-indazol-5-yl)-2-hydroxy-2-phenyl-N-[2-(6-trifluoromethyl-pyridin-3-yl)-ethyl]-acetamide

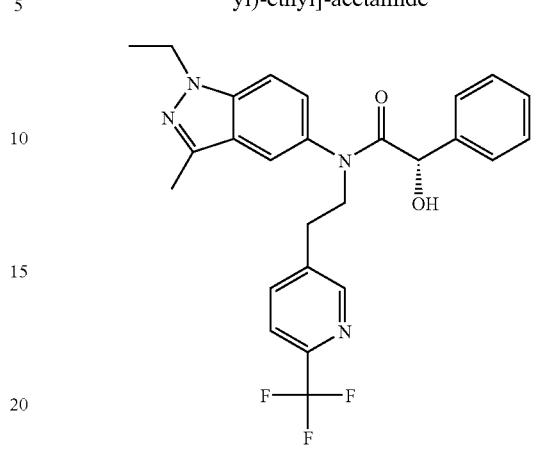

a) Step 1:

1-Ethyl-3-methyl-5-nitro-1H-indazole

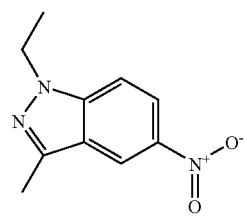

To a solution of 3-methyl-5-nitro-1H-indazole (1.50 g, 8.44 mmol, commercially available) in dry DMF (30 mL) under Argon was added NaH (0.43 g, 17.79 mmol) portionwise at 0° C. After 30 min, ethyl iodide (1.98 g, 1.03 mL, 12.7 mmol) was added and the mixture stirred at ambient temperature for 1 h then quenched by the addition of H$_2$O (2 mL), concentrated and redissolved in EtOAc (30 mL) then washed with H$_2$O (3×15 mL). The combined aqueous layers were extracted with EtOAc (3×15 mL) and the combined organic layers dried over Na$_2$SO$_4$, filtered and concentrated. Purification by chromatography (SiO$_2$, heptane:ethyl acetate=95:5 to 50:50) afforded the title compound (1.17 g, 67%) as a yellow solid. MS m/e: 206.0 [M+H]$^-$.

b) Step 2:

(1-Ethyl-3-methyl-1H-indazol-5-yl)-[2-(6-trifluoromethyl-pyridin-3-yl)-ethyl]-amine

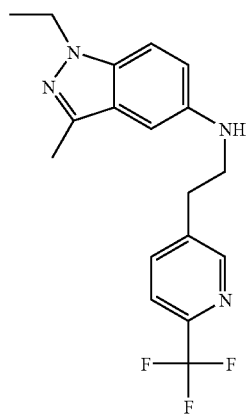

A solution of (6-trifluoromethyl-pyridin-3-yl)-acetonitrile (849 mg, 4.14 mmol, prepared as per example 47, step 1) and 1-ethyl-3-methyl-5-nitro-1H-indazole (700 mg, 3.76 mmol) in MeOH (10 mL) was treated with ammonium formate (5 eq.) and 10% Pd/C (140 mg) and stirred at 80° C. for 2 h. Filtration, concentration and purification by chromatography (SiO$_2$, heptane:ethyl acetate=95:5 to 60:40) afforded the title compound (794 mg, 61%) as a light yellow oil. MS m/e: 349.1 [M+H]$^+$.

c) Step 3:

Acetic acid (S)-{(1-ethyl-3-methyl-1H-indazol-5-yl)-[2-(6-trifluoromethyl-pyridin-3-yl)-ethyl]-carbamoyl}-phenyl-methyl ester

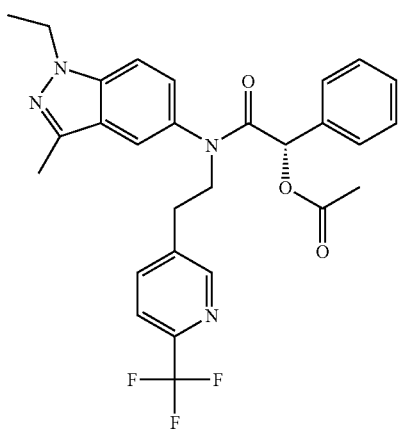

In analogy to example 47, step 3, (1-ethyl-3-methyl-1H-indazol-5-yl)-[2-(6-trifluoromethyl-pyridin-3-yl)-ethyl]-amine (100 mg, 0.287 mmol) was coupled to (S)-(+)-O-acetyl-L-mandelic acid (59 mg, 0.304 mmol) to give the title compound (179 mg, >100%) which was carried through to the next step without further purification.

d) Step 4:

(S)—N-(1-Ethyl-3-methyl-1H-indazol-5-yl)-2-hydroxy-2-phenyl-N-[2-(6-trifluoromethyl-pyridin-3-yl)-ethyl]-acetamide To a solution of acetic acid (S)-{(1-ethyl-3-methyl-1H-indazol-5-yl)-[2-(6-trifluoromethyl-pyridin-3-yl)-ethyl]-carbamoyl}-phenyl-methyl ester (150 mg, 0.286 mmol) in tetrahydrofuran (2.0 mL) were added 1.0 mL water and 20.0 mg (0.84 mmol) lithium hydroxide monohydrate. The mixture was stirred at room temperature for 2 h. The mixture was diluted with water and extracted 3 times with ethyl acetate. The combined organic layers were dried over Na$_2$SO$_4$, filtered and concentrated in vacuo. The crude oil was purified with flash column chromatography on silica eluting with a gradient formed from heptane and ethylacetate to provide 89 mg (65%) of the title compound as a colourless oil. MS(m/e): 483.1 [M+H]$^+$.

EXAMPLE 49

((S)-2-Hydroxy-2-phenyl-N-quinolin-3-yl-N-[2-(6-trifluoromethyl-pyridin-3-yl)-ethyl]-acetamide

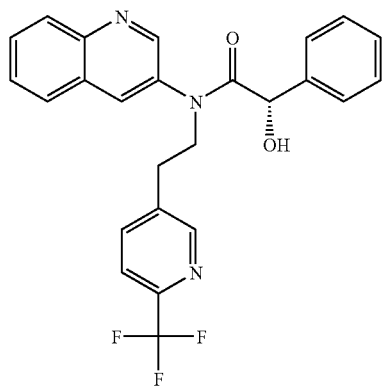

In analogy to example 47 (step 2) and example 48 (steps 3 & 4), Quinolin-3-ylamine, (6-Trifluoromethyl-pyridin-3-yl)-acetonitrile & (S)-(+)-O-acetyl-L-mandelic acid were successively coupled and hydrolysed to give the target compound. MS(m/e): 452.1 [M+H]$^+$.

EXAMPLE 50

(S)-2-Hydroxy-N-(6-methyl-pyridin-3-yl)-2-phenyl-N-[2-(6-trifluoromethyl-pyridin-3-yl)-ethyl]-acetamide

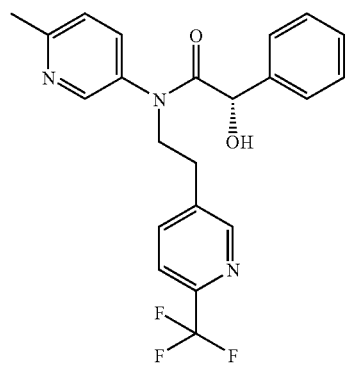

In analogy to example 49, 6-Methyl-pyridin-3-ylamine, (6-Trifluoromethyl-pyridin-3-yl)-acetonitrile & (S)-(+)-O-acetyl-L-mandelic acid were successively coupled and hydrolysed to give the target compound. MS(m/e): 416.1 [M+H]$^+$.

EXAMPLE 51

(S)-2-Hydroxy-N-(2-methyl-benzooxazol-5-yl)-2-phenyl-N-[2-(6-trifluoromethyl-pyridin-3-yl)-ethyl]-acetamide

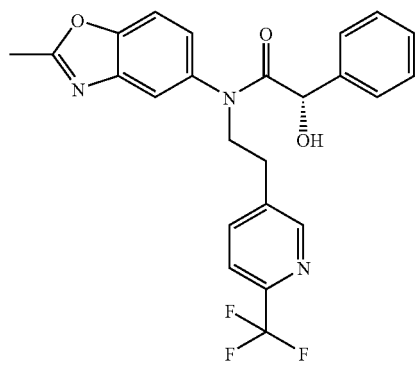

In analogy to example 49, 2-Methyl-benzooxazol-5-ylamine, (6-Trifluoromethyl-pyridin-3-yl)-acetonitrile & (S)-(+)-O-acetyl-L-mandelic acid were successively coupled and hydrolysed to give the target compound. MS(m/e): 456.1 [M+H]$^+$.

EXAMPLE 52

(S)-2-Hydroxy-N-(2-methyl-benzooxazol-6-yl)-2-phenyl-N-[2-(6-trifluoromethyl-pyridin-3-yl)-ethyl]-acetamide

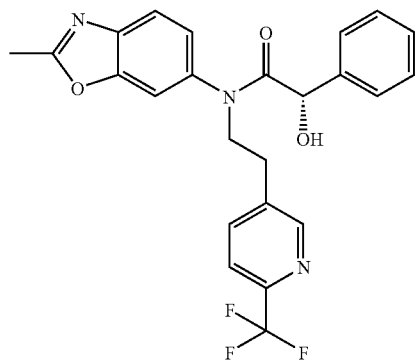

In analogy to example 49, 2-Methyl-benzooxazol-6-ylamine, (6-Trifluoromethyl-pyridin-3-yl)-acetonitrile & (S)-(+)-O-acetyl-L-mandelic acid were successively coupled and hydrolysed to give the target compound. MS(m/e): 456.1 [M+H]$^+$.

EXAMPLE 53

(S)-2-(4-Fluoro-phenyl)-2-hydroxy-N-(6-methyl-pyridin-3-yl)-N-[2-(6-trifluoromethyl-pyridin-3-yl)-ethyl]-acetamide

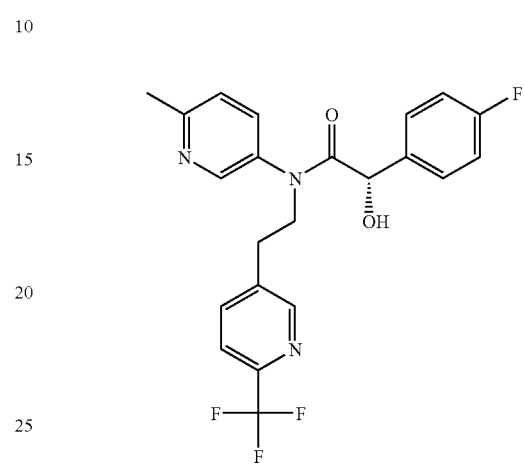

In analogy to example 47, steps 2, 3 & 4, 6-Methyl-pyridin-3-ylamine, (6-Trifluoromethyl-pyridin-3-yl)-acetonitrile & (4-Fluoro-phenyl)-oxo-acetic acid were successively coupled and reduced to give after separation by chromatography on a chiral column (+ve rotation) the target compound. MS(m/e): 434.1 [M+H]$^+$.

EXAMPLE 54

(R,S)-2-(4-Fluoro-phenyl)-2-hydroxy-N-(1-methyl-1H-indol-6-yl)-N-[2-(5-trifluoromethyl-pyridin-2-yl)-ethyl]-acetamide

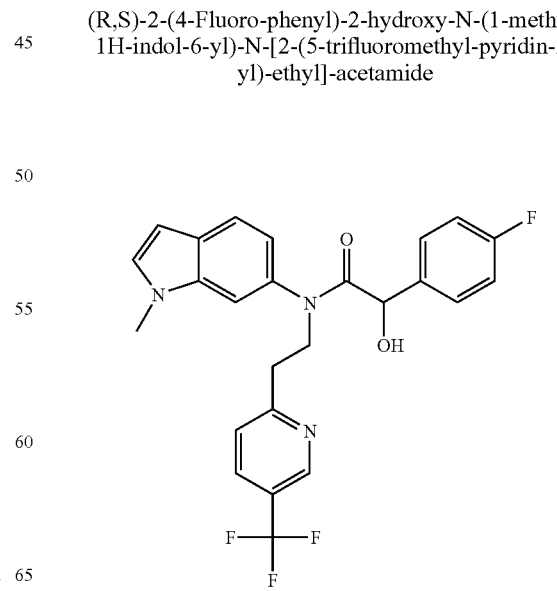

a) Step 1:

(1-Methyl-1H-indol-6-yl)-[2-(5-trifluoromethyl-pyridin-2-yl)-ethyl]-amine

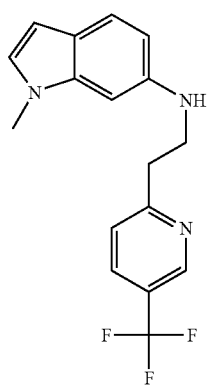

To 2-(5-trifluoromethyl-pyridin-2-yl)-ethylamine (200 mg, 1.05 mmol) was added 6-bromo-1-methyl-1H-indole (685 mg, 2.10 mmol), cuprous iodide (10 mg, 0.05 mmol) and cesium carbonate (685 mg, 2.1 mmol) under an argon atmosphere. Then DMF (400 μl) and 2-acetylcyclohexanone (28 μl, 0.21 mmol) were added and the reaction mixture was stirred for 4 h at 120° C. After cooling to ambient temperature the reaction mixture was separated between tert-butylmethylether (2×20 ml) and water (15 ml). The combined organic layers were washed with brine (15 ml) and dried over sodium sulfate. Concentration and purification by chromatography (SiO$_2$, heptane:ethyl acetate=100:0 to 67:33) afforded the title compound (114 mg, 34%) as a light brown oil. MS m/e: 320.1 [M+H]$^+$.

b) Step 2:

(R,S)-2-(4-Fluoro-phenyl)-2-hydroxy-N-(1-methyl-1H-indol-6-yl)-N-[2-(5-trifluoromethyl-pyridin-2-yl)-ethyl]-acetamide To a solution of (1-methyl-1H-indol-6-yl)-[2-(5-trifluoromethyl-pyridin-2-yl)-ethyl]-amine (105 mg, 0.33 mmol) and (R,S)-acetoxy-(4-fluoro-phenyl)-acetic acid (77 mg, 0.36 mmol) in dichloromethane (2.1 ml) was added 1-(3-dimethylaminopropyl)-3-ethylcarbodiimide hydrochloride (69 mg, 0.36 mmol) at 0° C. After stirring for 1.5 h at 0° C., the reaction mixture was washed with aqueous sodium carbonate (saturated, 20 ml) and water (20 ml). The combined aqueous layers were extracted with dichloromethane (2×30 ml). The combined organic layers were combined, dried over sodium sulfate and concentrated. The resulting residue was treated with lithium hydroxide monohydrate (15 mg, 0.36 mmol), THF (1.56 ml) and water (780 μl) and stirred for 18 h at ambient temperature. It was diluted with water (20 ml), and extracted with ethyl acetate (2×20 ml). The combined organic layers were dried over sodium sulfate. Concentration and purification by chromatography (SiO$_2$, heptane:ethyl acetate=90:10 to 25:75) afforded the title compound (124 mg, 80%) as a light yellow foam. MS m/e: 472.2 [M+H]$^+$.

EXAMPLE 55

(S)—N-(2,3-Dihydro-benzo[1,4]dioxin-6-yl)-2-hydroxy-2-phenyl-N-[2-(6-trifluoromethyl-pyridin-3-yl)-ethyl]-acetamide

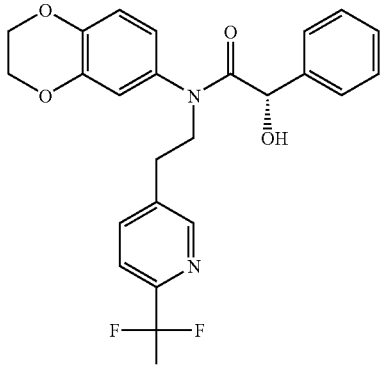

a) Step 1:

(2,3-Dihydro-benzo[1,4]dioxin-6-yl)-[2-(6-trifluoromethyl-pyridin-3-yl)-ethyl]-amine

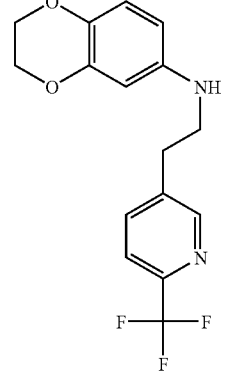

A solution of 5 mmol (6-trifluoromethyl-pyridin-3-yl)-acetonitrile (prepared as per example 47, step 1) and 1.1 eq. 2,3-Dihydro-benzo[1,4]dioxin-6-ylamine in MeOH (20 mL) was treated with ammonium formate (5 eq.) and 10% Pd/C (200 mg) and stirred at 80° C. for 2 h. Filtration, concentration and purification by chromatography (SiO$_2$, heptane:ethyl acetate=95:5 to 60:40) afforded the title compound (24%) as a light yellow oil. MS m/e: 325.0 [M+H]$^+$.

b) Step 2:

Acetic acid (S)-{(2,3-dihydro-benzo[1,4]dioxin-6-yl)-[2-(6-trifluoromethyl-pyridin-3-yl)-ethyl]-carbamoyl}-phenyl-methyl ester

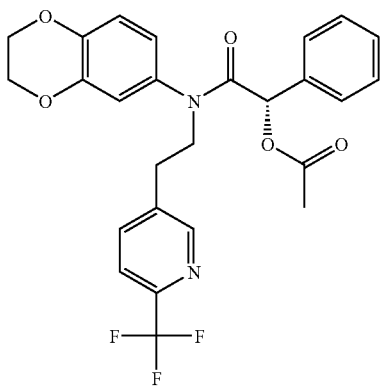

To a 0° C. solution of 100 mg ((2,3-Dihydro-benzo[1,4]dioxin-6-yl)-[2-(6-trifluoromethyl-pyridin-3-yl)-ethyl]-amine and 63 mg (S)-(+)-O-acetyl-L-mandelic acid in 4 mL dichloromethane was added 62 mg 1-(3-dimethylaminopropyl)-3-ethylcarbodiimide hydrochloride. The mixture was stirred at 0° C. for 30 minutes. The solution was washed once with a saturated NaHCO$_3$ solution and once with water. The washings were extracted once with dichloromethane. The combined organic layers were dried over Na$_2$SO$_4$, filtered and concentrated in vacuo. The crude oil (139 mg) was used directly for the next step.

c) Step 3:

(S)—N-(2,3-Dihydro-benzo[1,4]dioxin-6-yl)-2-hydroxy-2-phenyl-N-[2-(6-trifluoromethyl-pyridin-3-yl)-ethyl]-acetamide To a solution of acetic acid 139 mg Acetic acid (S)-{(2,3-dihydro-benzo[1,4]dioxin-6-yl)-[2-(6-trifluoromethyl-pyridin-3-yl)-ethyl]-carbamoyl}-phenyl-methyl ester in tetrahydrofuran (3.0 mL) were added 1.0 mL water and 13 mg lithium hydroxide monohydrate. The mixture was stirred at room temperature for 2 h. The mixture was diluted with water and extracted 3 times with ethyl acetate. The combined organic layers were dried over Na$_2$SO$_4$, filtered and concentrated in vacuo. The crude oil was purified with flash column chromatography on silica eluting with a gradient formed from heptane and ethylacetate to provide the title compound. MS(m/e): 459.1 [M+H]$^+$.

EXAMPLE 56

(S)-2-Hydroxy-N-(3-methoxy-phenyl)-2-phenyl-N-[2-(6-trifluoromethyl-pyridin-3-yl)-ethyl]-acetamide

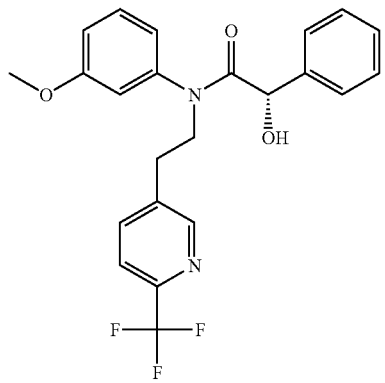

In analogy to example 55, 3-Methoxy-phenylamine, (6-Trifluoromethyl-pyridin-3-yl)-acetonitrile & (S)-(+)-O-acetyl-L-mandelic acid were successively coupled then hydrolysed to give the target compound. MS(m/e): 431.1 [M+H]$^+$.

EXAMPLE 57

(S)—N-(3,4-Dimethyl-phenyl)-2-(oxetan-3-ylamino)-2-phenyl-N-[2-(6-trifluoromethyl-pyridin-3-yl)-ethyl]-acetamide

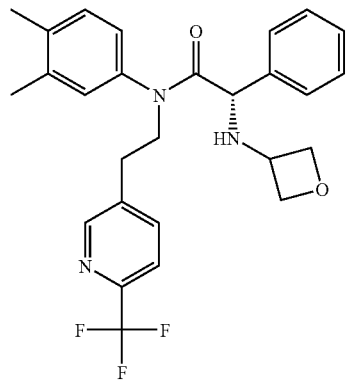

To a solution of 25 mg (S)-2-Amino-N-(3,4-dimethyl-phenyl)-2-phenyl-N-[2-(6-trifluoromethyl-pyridin-3-yl)-ethyl]-acetamide (from example 1) in 1.5 ml dry CH$_2$Cl$_2$ under argon in a sealed tube was added 1.1 eq. oxetan-3-one. The reaction mixture was stirred at RT for 20 min, followed by the addition of 3.0 eq., Sodium triacetoxyborohydride and the reaction stirred for 16 h at RT. The reaction mixture diluted with 10 ml CH$_2$Cl$_2$ and washed with 2M aq. Na$_2$CO$_3$ 2M, dried and concentrated then chromatographed on silica gel (EtOAc/Heptane, gradient elution) to give the desired compound. MS(m/e): 484.2 [M+H]$^+$.

EXAMPLE 58

(S)-2-Hydroxy-N-(3-methoxy-phenyl)-2-phenyl-N-[2-(6-trifluoromethyl-pyridin-3-yl)-ethyl]-acetamide

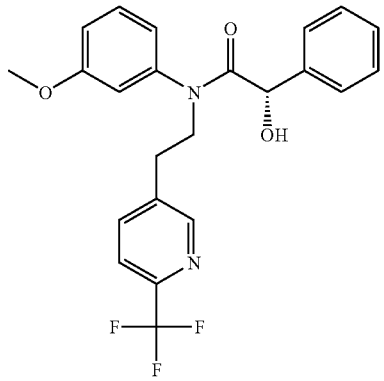

In analogy to example 55, 6-Amino-chroman-4-ol (as described in WO 2005037830), (6-Trifluoromethyl-pyridin-3-yl)-acetonitrile & (S)-(+)-O-acetyl-L-mandelic acid were successively coupled then hydrolysed to give the target compound. MS(m/e): 473.1 [M+H]+.

EXAMPLE 59

(S)—N-(2,2-Dimethyl-benzo[1,3]dioxol-5-yl)-2-hydroxy-2-phenyl-N-[2-(6-trifluoromethyl-pyridin-3-yl)-ethyl]-acetamide

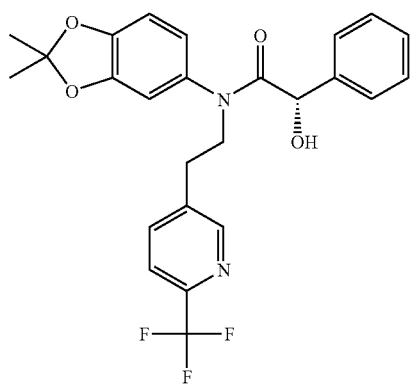

In analogy to example 55, 2,2-Dimethyl-benzo[1,3]dioxol-5-ylamine, (6-Trifluoromethyl-pyridin-3-yl)-acetonitrile & (S)-(+)-O-acetyl-L-mandelic acid were successively coupled then hydrolysed to give the target compound. MS(m/e): 473.1 [M+H]+.

EXAMPLE 60

(S)-2-(4-Fluoro-phenyl)-2-hydroxy-N-(5,6,7,8-tetrahydro-naphthalen-2-yl)-N-[2-(6-trifluoromethyl-pyridin-3-yl)-ethyl]-acetamide

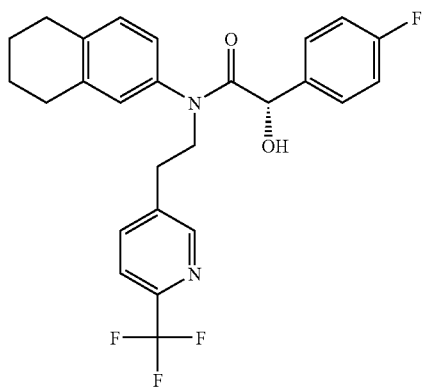

In analogy to example 47 (steps 3 & 4), 5,6,7,8-Tetrahydro-naphthalen-2-ylamine, (6-Trifluoromethyl-pyridin-3-yl)-acetonitrile & (4-Fluoro-phenyl)-oxo-acetic acid were successively coupled then reduced to give after chiral chromatography (+ve rotation) the target compound. MS(m/e): 473.1 [M+H]+.

EXAMPLE 61

(S)-2-(4-Fluoro-phenyl)-2-hydroxy-N-(3-methoxy-4-methyl-phenyl)-N-[2-(6-trifluoromethyl-pyridin-3-yl)-ethyl]-acetamide

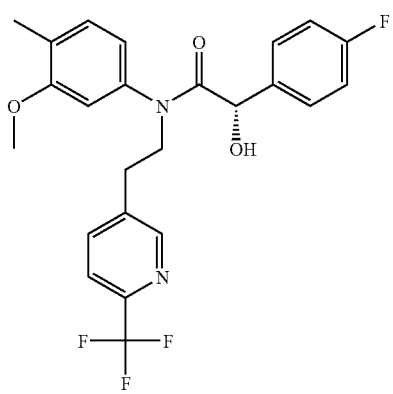

In analogy to example 47 (steps 3 & 4), 3-Methoxy-4-methyl-phenylamine, (6-Trifluoromethyl-pyridin-3-yl)-acetonitrile & (4-Fluoro-phenyl)-oxo-acetic acid were successively coupled then reduced to give after chiral chromatography (+ve rotation) the target compound. MS(m/e): 463.1 [M+H]+.

EXAMPLE 62

(S)-2-(4-Fluoro-phenyl)-2-hydroxy-N-(3-methoxy-4-methyl-phenyl)-N-[2-(6-trifluoromethyl-pyridin-3-yl)-ethyl]-acetamide

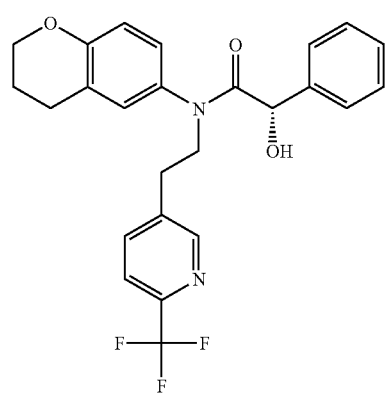

In analogy to example 55, Chroman-6-ylamine (described in WO2000000489), (6-Trifluoromethyl-pyridin-3-yl)-acetonitrile & (S)-(+)-O-acetyl-L-mandelic acid were successively coupled then hydrolysed to give the target compound. MS(m/e): 457.1 [M+H]+.

EXAMPLE 63

(S)-2-Hydroxy-N-((S)-4-hydroxy-chroman-6-yl)-2-phenyl-N-[2-(6-trifluoromethyl-pyridin-3-yl)-ethyl]-acetamide

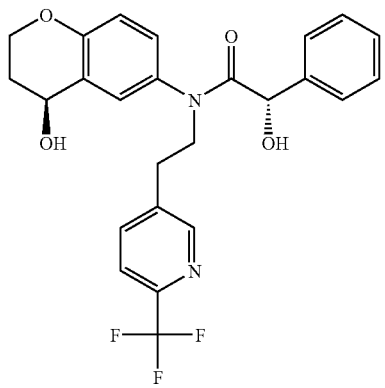

In analogy to example 55, 6-Amino-chroman-4-ol (WO 2003063794), (6-Trifluoromethyl-pyridin-3-yl)-acetonitrile & (S)-(+)-O-acetyl-L-mandelic acid were successively coupled then hydrolysed to give after silica gel chromatography the target compound. MS(m/e): 473.1 [M+H]+.

EXAMPLE 64

(S)-2-Hydroxy-N—((R)-4-hydroxy-chroman-6-yl)-2-phenyl-N-[2-(6-trifluoromethyl-pyridin-3-yl)-ethyl]-acetamide

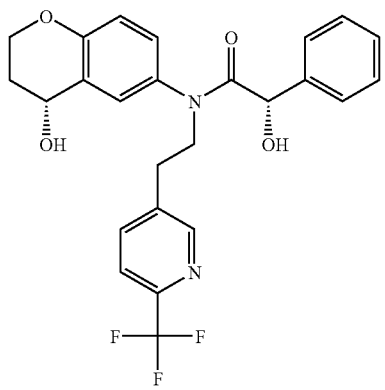

In analogy to example 55, 6-Amino-chroman-4-ol (WO 2003063794), (6-Trifluoromethyl-pyridin-3-yl)-acetonitrile & (S)-(+)-O-acetyl-L-mandelic acid were successively coupled then hydrolysed to give after silica gel chromatography the target compound. MS(m/e): 473.1 [M+H]+.

EXAMPLE 65

Acetic acid (S)-{(3,4-dimethyl-phenyl)-[2-(5-trifluoromethyl-pyridin-2-yl)-ethyl]-carbamoyl}-phenyl-methyl ester

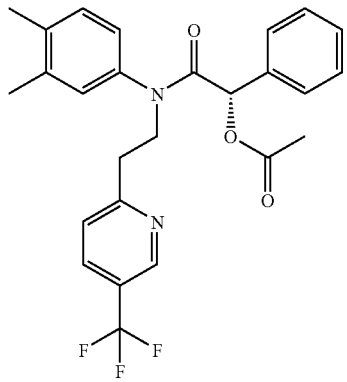

In analogy to the procedure described for the synthesis of example 26, step 1, the title compound was prepared from (3,4-dimethyl-phenyl)-[2-(5-trifluoromethyl-pyridin-2-yl)-ethyl]-amine (example 25, step 1) and (S)-(+)-O-acetyl-L-mandelic acid. MS(m/e): 471.2 [M+H]+.

EXAMPLE 66

(S)—N-[2-(5-Chloro-pyridin-2-yl)-ethyl]-N-(3,4-dimethyl-phenyl)-2-hydroxy-2-phenyl-acetamide

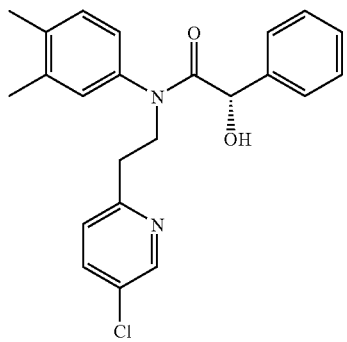

In analogy to example 25 step 1 and 26 step 1-2, [2-(5-Chloro-pyridin-2-yl)-ethyl]-(3,4-dimethyl-phenyl)-amine obtained by reacting 5-Chloro-2-vinyl-pyridine (CAS: 223445-06-5) with 3,4-dimethylaniline was coupled with (S)-(+)-O-acetyl-L-mandelic acid then hydrolysed to provide the title compound. MS(m/e): 395.1 [M+H]+.

EXAMPLE 67

(S)-2-Amino-N-(3,4-dimethyl-phenyl)-N-[2-(4-methyl-thiazol-2-yl)-ethyl]-2-phenyl-acetamide hydrochloride

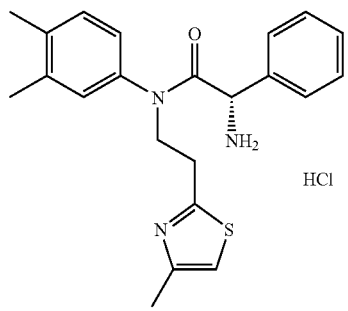

In analogy to example 21 step 1-4, the title compound was prepared from 3,4-dimethylaniline and 4-methylthiazol-2-yl)-acetic acid (commercial). MS(m/e): 380.3 [M+H]+.

EXAMPLE 68

(S)—N-(3,4-Dimethyl-phenyl)-N-[2-(5-fluoro-pyridin-2-yl)-ethyl]-2-hydroxy-2-phenyl-acetamide

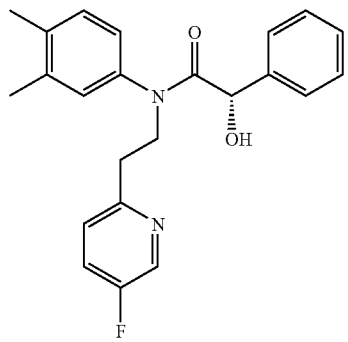

In analogy to example 25 step 1 and 26 step 1-2, (3,4-dimethyl-phenyl)-[2-(5-fluoro-pyridin-2-yl)-ethyl]-amine obtained by reacting 5-Fluoro-2-vinyl-pyridine (CAS: 869108-71-4) with 3,4-dimethylaniline was coupled with (S)-(+)-O-acetyl-L-mandelic acid then hydrolysed to provide the title compound. MS(m/e): 379.3 [M+H]+.

EXAMPLE 69

(S)—N-(3,4-Dimethyl-phenyl)-2-hydroxy-2-phenyl-N-(2-thiophen-3-yl-ethyl)-acetamide

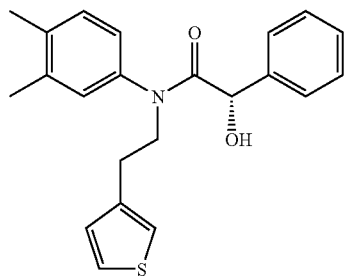

In analogy to example 22 step 1 and 26 step 1-2, (3,4-dimethyl-phenyl)-(2-thiophen-3-yl-ethyl)-amine obtained by reacting 2-thiophen-3-yl-ethylamine (commercial) with 4-iodo-o-xylene (commercial) was coupled with (S)-(+)-O-acetyl-L-mandelic acid then hydrolysed to provide the title compound. MS(m/e): 366.2 [M+H]+.

EXAMPLE 70

(S)—N-(3,4-Dimethyl-phenyl)-2-hydroxy-N-[2-(3-methyl-isoxazol-5-yl)-ethyl]-2-phenyl-acetamide

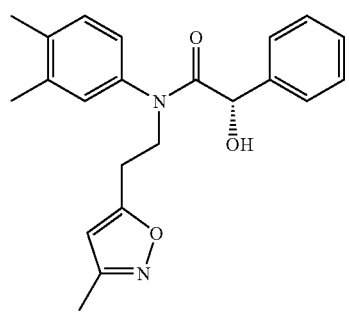

In analogy to example 21 step 1-2 and 26 step 1-2, the title compound was prepared from 3,4-dimethylaniline and 3-methyl-5-isoxazole acetic acid (commercial). MS(m/e): 365.2 [M+H]+.

EXAMPLE 71

(R,S)-N-(2,3-Dihydro-benzofuran-6-yl)-2-(4-fluorophenyl)-2-hydroxy-N-[2-(6-trifluoromethyl-pyridin-3-yl)-ethyl]-acetamide

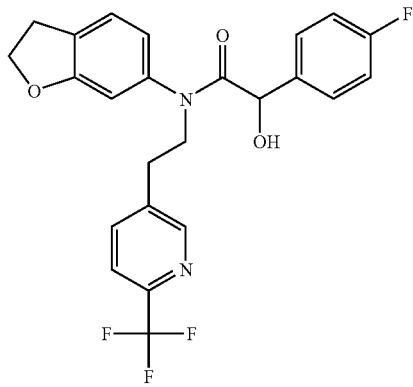

a) Step 1:

(2,3-Dihydro-benzofuran-6-yl)-[2-(6-trifluoromethyl-pyridin-3-yl)-ethyl]-amine

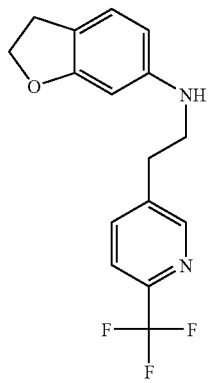

To 2-(6-trifluoromethyl-pyridin-3-yl)-ethylamine (955 mg, 5.0 mmol) were added 6-bromo-2,3-dihydro-benzofuran (1.00 g, 5.0 mmol), cuprous iodide (48 mg, 0.25 mmol) and cesium carbonate (3.27 g, 10.0 mmol) under an Ar-atmosphere. Then DMF (2.0 ml) and 2-acetylcyclohexanone (133 µl, 0.10 mmol) were added and the reaction mixture was stirred for 2 h at 120° C. It was cooled to ambient temperature and separated between TBME (40 ml) and water (15 ml). The organic layer was washed with brine (15 ml) and dried over sodium sulfate. Concentration and purification by chromatography (SiO$_2$, heptane:ethyl acetate=100:0 to 67:33) afforded the title compound (803 mg, 52%) as a yellow oil. MS m/e: 309.3 [M+H]$^+$.

b) Step 2:

N-(2,3-Dihydro-benzofuran-6-yl)-2-(4-fluor-phenyl)-2-oxo-N-[2-(6-trifluoromethyl-pyridin-3-yl)-ethyl]-acetamide

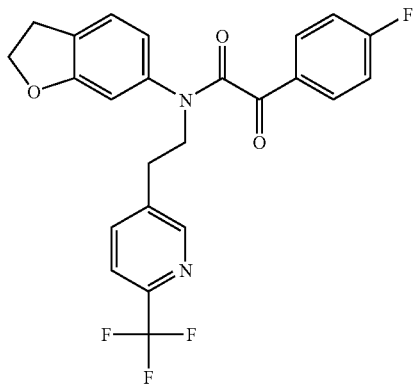

In analogy to the procedure described for the synthesis example 7 (step 1), the title compound N-(2,3-dihydro-benzofuran-6-yl)-2-(4-fluor-phenyl)-2-oxo-N-[2-(6-trifluoromethyl-pyridin-3-yl)-ethyl]-acetamide (MS m/e: 459.2 [M+H]$^+$) was prepared from (2,3-dihydro-benzofuran-6-yl)-[2-(6-trifluoromethyl-pyridin-3-yl)-ethyl]-amine instead of (3,4-dimethyl-phenyl)-[2-(6-trifluoromethyl-pyridin-3-yl)-ethyl]-amine.

c) Step 3:

(R,S)—N-(2,3-Dihydro-benzofuran-6-yl)-2-(4-fluoro-phenyl)-2-hydroxy-N-[2-(6-trifluoromethyl-pyridin-3-yl)-ethyl]-acetamide In analogy to the procedure described for the synthesis example 7 (step 2), the title compound (R,S)—N-(2,3-dihydro-benzofuran-6-yl)-2-(4-fluoro-phenyl)-2-hydroxy-N-[2-(6-trifluoromethyl-pyridin-3-yl)-ethyl]-acetamide (MS m/e: 461.3 [M+H]$^+$) was prepared from N-(2,3-dihydro-benzofuran-6-yl)-2-(4-fluor-phenyl)-2-oxo-N-[2-(6-trifluoromethyl-pyridin-3-yl)-ethyl]-acetamide, leaving out the separation step by chromatography on a chiral column.

EXAMPLE 72

(R,S)-3-Amino-N-(2,3-dihydro-benzofuran-6-yl)-2-phenyl-N-[2-(6-trifluoromethyl-pyridin-3-yl)-ethyl]-propionamide hydrochloride

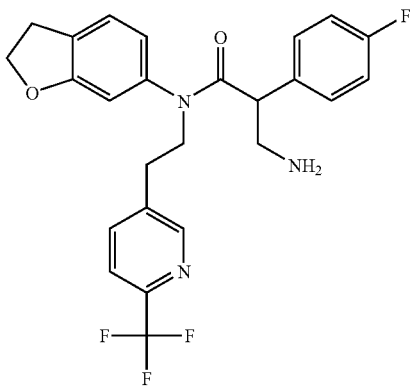

a) Step 1:

(R,S)-(2-{(2,3-Dihydro-benzofuran-6-yl)-[2-(6-trifluoromethyl-pyridin-3-yl)-ethyl]-carbamoyl}-2-phenyl-ethyl)-carbamic acid tert-butyl ester

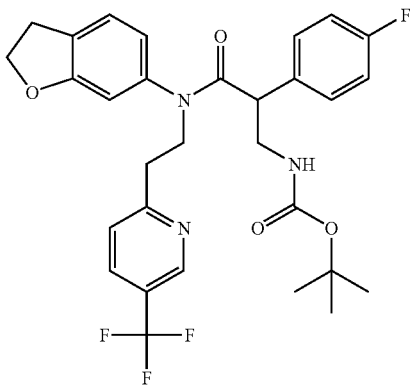

In analogy to the procedure described for the synthesis example 7 (step 1), the title compound (R,S)-(2-{(2,3-Dihydro-benzofuran-6-yl)-[2-(6-trifluoromethyl-pyridin-3-yl)-ethyl]-carbamoyl}-2-phenyl-ethyl)-carbamic acid tert-butyl ester (MS m/e: 456.2 [M+H—BOC]⁺) was prepared from (2,3-dihydro-benzofuran-6-yl)-[2-(6-trifluoromethyl-pyridin-3-yl)-ethyl]-amine instead of (3,4-dimethyl-phenyl)-[2-(6-trifluoromethyl-pyridin-3-yl)-ethyl]-amine and (R,S)-3-tert-butoxycarbonylamino-2-phenyl-propionic acid instead of (4-fluoro-phenyl)-oxo-acetic acid.

b) Step 2:

(R,S)-3-Amino-N-(2,3-dihydro-benzofuran-6-yl)-2-phenyl-N-[2-(6-trifluoromethyl-pyridin-3-yl)-ethyl]-propionamide hydrochloride (R,S)-(2-{(2,3-Dihydro-benzofuran-6-yl)-[2-(6-trifluoromethyl-pyridin-3-yl)-ethyl]-carbamoyl}-2-phenyl-ethyl)-carbamic acid tert-butyl ester (47 mg, 0.09 mmol) was taken up in hydrogen chloride solution (4 M in dioxan, 1.5 ml, 6.0 mmol) and stirred for 2 h at ambient temperature. Concentration afforded the title compound (46 mg, 99%) as a light-brown semisolid. MS m/e: 456.2 [M+H—HCl]⁺.

EXAMPLE 73

(R,S)-2-(4-Fluoro-phenyl)-2-hydroxy-N-indan-5-yl-N-[2-(5-trifluoromethyl-pyridin-2-yl)-ethyl]-acetamide

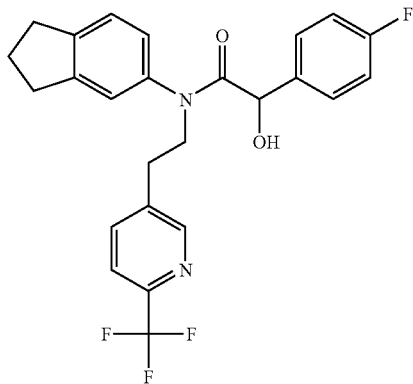

a) Step 1:

Indan-5-yl-[2-(5-trifluoromethyl-pyridin-2-yl)-ethyl]-amine

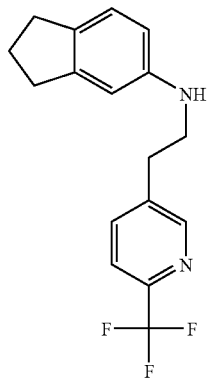

In analogy to the procedure described for the synthesis example 25 (step 1), the title compound Indan-5-yl-[2-(5-trifluoromethyl-pyridin-2-yl)-ethyl]-amine (MS m/e: 307.2 [M+H]⁺) was prepared from 5-amino-indan instead of 3,4-dimethylaniline and 5-trifluoromethyl-2-vinyl-pyridine.

b) Step 2:

(R,S)-Acetic acid (4-fluoro-phenyl)-{indan-5-yl-[2-(5-trifluoromethyl-pyridin-2-yl)-ethyl]-carbamoyl}-methyl ester

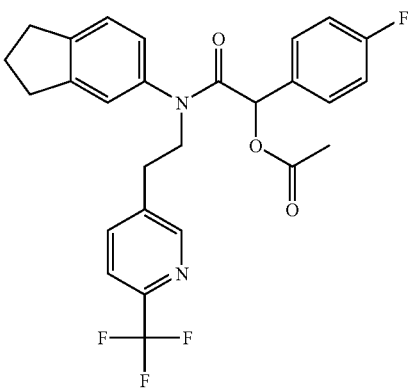

In analogy to the procedure described for the synthesis example 7 (step 1), the title compound (R,S)-Acetic acid (4-fluoro-phenyl)-{indan-5-yl-[2-(5-trifluoromethyl-pyridin-2-yl)-ethyl]-carbamoyl}-methyl ester (MS m/e: 501.1 [M+H]⁺) was prepared from indan-5-yl-[2-(5-trifluoromethyl-pyridin-2-yl)-ethyl]-amine instead of (3,4-dimethyl-phenyl)-[2-(6-trifluoromethyl-pyridin-3-yl)-ethyl]-amine and (R,S)-acetoxy-(4-fluoro-phenyl)-acetic acid instead of (4-fluoro-phenyl)-oxo-acetic acid.

b) Step 3:

(R,S)-2-(4-Fluoro-phenyl)-2-hydroxy-N-indan-5-yl-N-[2-(5-trifluoromethyl-pyridin-2-yl)-ethyl]-acetamide (R,S)-Acetic acid (4-fluoro-phenyl)-{indan-5-yl-[2-(5-trifluoromethyl-pyridin-2-yl)-ethyl]-carbamoyl}-methyl ester (150 mg, 0.30 mmol) was dissolved in THF (1.5 mL) and water (0.8 mL). Lithium hydroxide monohydrate (14 mg, 0.33 mmol) was added and the reaction mixture was stirred at ambient temperature for 18 h. Water (8 mL) was added and after extraction with ethyl acetate the combined organic layers were washed with water, and dried over sodium sulfate. Concentration and purification by chromatography (SiO₂, heptane:ethyl acetate=100:0 to 60:40) afforded the title compound (91 mg, 66%) as a light yellow oil. MS m/e: 459.2 [M+H]⁺.

EXAMPLE 74

(R,S)-2-(4-Fluoro-phenyl)-2-hydroxy-N-(4-isopropyl-phenyl)-N-[2-(5-trifluoromethyl-pyridin-2-yl)-ethyl]-acetamide

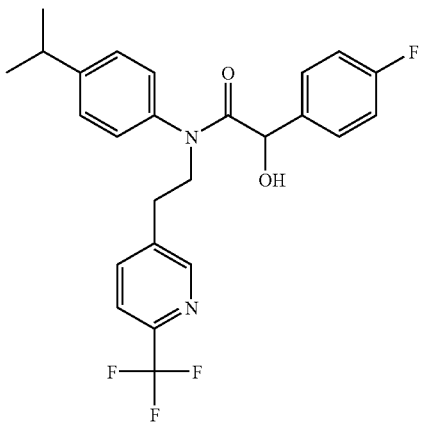

a) Step 1:

(4-Isopropyl-phenyl)-[2-(5-trifluoromethyl-pyridin-2-yl)-ethyl]-amine

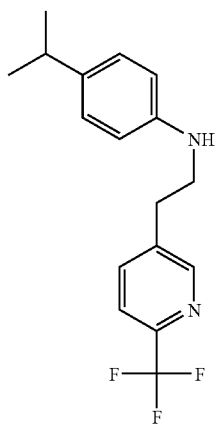

In analogy to the procedure described for the synthesis example 25 (step 1), the title compound (4-isopropyl-phenyl)-[2-(5-trifluoromethyl-pyridin-2-yl)-ethyl]-amine (MS m/e: 309.2 [M+H]$^+$) was prepared from 4-isopropylaniline instead of 3,4-dimethylaniline and 5-trifluoromethyl-2-vinyl-pyridine.

b) Step 2:

(R,S)-Acetic acid (4-fluoro-phenyl)-{(4-isopropyl-phenyl)-[2-(5-trifluoromethyl-pyridin-2-yl)-ethyl]-carbamoyl}-methyl ester

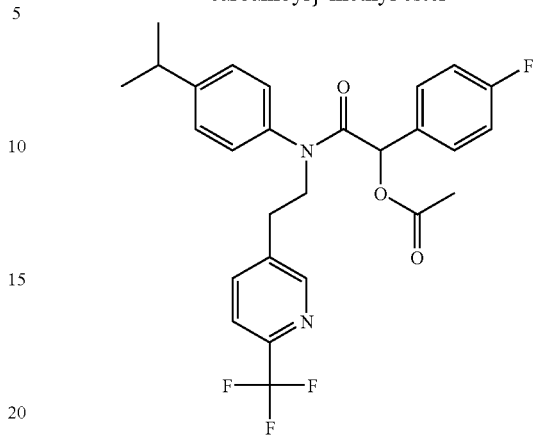

In analogy to the procedure described for the synthesis example 7 (step 1), the title compound (R,S)-Acetic acid (4-fluoro-phenyl)-{(4-isopropyl-phenyl)-[2-(5-trifluoromethyl-pyridin-2-yl)-ethyl]-carbamoyl}-methyl ester (MS m/e: 503.2 [M+H]$^+$) was prepared from (4-isopropyl-phenyl)-[2-(5-trifluoromethyl-pyridin-2-yl)-ethyl]-amine instead of (3,4-dimethyl-phenyl)-[2-(6-trifluoromethyl-pyridin-3-yl)-ethyl]-amine and (R,S)-acetoxy-(4-fluoro-phenyl)-acetic acid instead of (4-fluoro-phenyl)-oxo-acetic acid.

c) Step 3:

(R,S)-2-(4-Fluoro-phenyl)-2-hydroxy-N-(4-isopropyl-phenyl)-N-[2-(5-trifluoromethyl-pyridin-2-yl)-ethyl]-acetamide In analogy to the procedure described for the synthesis example 73 (step 3), the title compound (R,S)-2-(4-fluoro-phenyl)-2-hydroxy-N-(4-isopropyl-phenyl)-N-[2-(5-trifluoromethyl-pyridin-2-yl)-ethyl]-acetamide (MS m/e: 461.2 [M+H]$^+$) was prepared from (R,S)-acetic acid (4-fluoro-phenyl)-{(4-isopropyl-phenyl)-[2-(5-trifluoromethyl-pyridin-2-yl)-ethyl]-carbamoyl}-methyl ester instead of (R,S)-acetic acid (4-fluoro-phenyl)-{indan-5-yl-[2-(5-trifluoromethyl-pyridin-2-yl)-ethyl]-carbamoyl}-methyl ester.

EXAMPLE 75

(R,S)—N-(2,3-Dihydro-benzofuran-5-yl)-2-(4-fluoro-phenyl)-2-hydroxy-N-[2-(5-trifluoromethyl-pyridin-2-yl)-ethyl]-acetamide

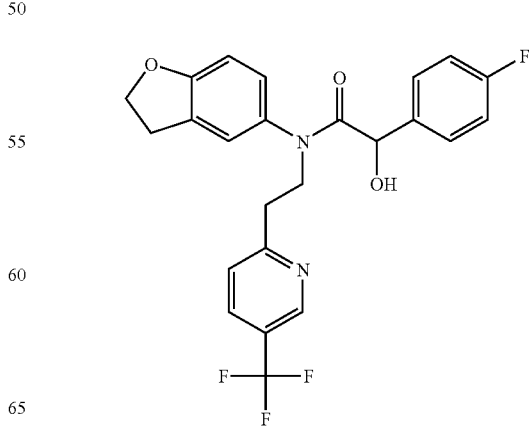

a) Step 1:

(2,3-Dihydro-benzofuran-5-yl)-[2-(5-trifluoromethyl-pyridin-2-yl)-ethyl]-amine

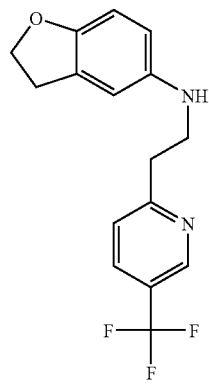

In analogy to the procedure described for the synthesis example 71 (step 1), the title compound (2,3-dihydro-benzofuran-5-yl)-[2-(5-trifluoromethyl-pyridin-2-yl)-ethyl]-amine (MS m/e: 309.0 [M+H]$^+$) was prepared from 5-bromo-2,3-dihydro-1-benzofuran instead of 6-bromo-2,3-dihydro-benzofuran and 2-(5-trifluoromethyl-pyridin-2-yl)-ethylamine instead of 2-(6-trifluoromethyl-pyridin-3-yl)-ethylamine.

b) Step 2:

(R,S)-Acetic acid {(2,3-dihydro-benzofuran-5-yl)-[2-(5-trifluoromethyl-pyridin-2-yl)-ethyl]-carbamoyl}-(4-fluoro-phenyl)-methyl ester

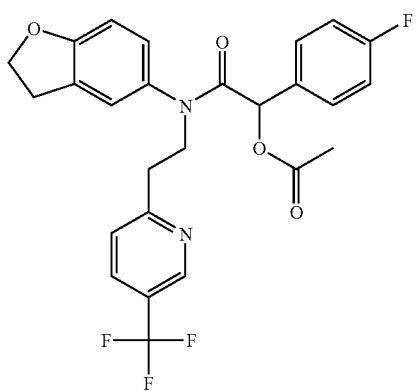

In analogy to the procedure described for the synthesis example 7 (step 1), the title compound (R,S)-acetic acid {(2,3-dihydro-benzofuran-5-yl)-[2-(5-trifluoromethyl-pyridin-2-yl)-ethyl]-carbamoyl}-(4-fluoro-phenyl)-methyl ester (MS m/e: 503.2 [M+H]$^+$) was prepared from (2,3-dihydro-benzofuran-5-yl)-[2-(5-trifluoromethyl-pyridin-2-yl)-ethyl]-amine instead of (3,4-dimethyl-phenyl)-[2-(6-trifluoromethyl-pyridin-3-yl)-ethyl]-amine and (R,S)-acetoxy-(4-fluoro-phenyl)-acetic acid instead of (4-fluoro-phenyl)-oxo-acetic acid.

c) Step 3:

(R,S)—N-(2,3-Dihydro-benzofuran-5-yl)-2-(4-fluoro-phenyl)-2-hydroxy-N-[2-(5-trifluoromethyl-pyridin-2-yl)-ethyl]-acetamide In analogy to the procedure described for the synthesis example 73 (step 3), the title compound (R,S)—N-(2,3-dihydro-benzofuran-5-yl)-2-(4-fluoro-phenyl)-2-hydroxy-N-[2-(5-trifluoromethyl-pyridin-2-yl)-ethyl]-acetamide (MS m/e: 461.3 [M+H]$^+$) was prepared from (R,S)-acetic acid {(2,3-dihydro-benzofuran-5-yl)-[2-(5-trifluoromethyl-pyridin-2-yl)-ethyl]-carbamoyl}-(4-fluoro-phenyl)-methyl ester instead of (R,S)-acetic acid (4-fluoro-phenyl)-{indan-5-yl-[2-(5-trifluoromethyl-pyridin-2-yl)-ethyl]-carbamoyl}-methyl ester.

EXAMPLE 76

(R,S)-2-(4-Fluoro-phenyl)-2-hydroxy-N-(3-methoxy-phenyl)-N-[2-(5-trifluoromethyl-pyridin-2-yl)-ethyl]-acetamide

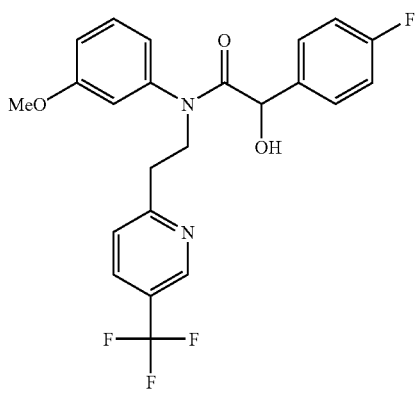

a) Step 1:

(3-Methoxy-phenyl)-[2-(5-trifluoromethyl-pyridin-2-yl)-ethyl]-amine

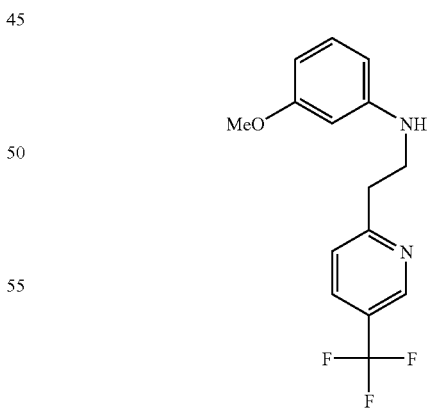

In analogy to the procedure described for the synthesis example 71 (step 1), the title compound (3-methoxy-phenyl)-[2-(5-trifluoromethyl-pyridin-2-yl)-ethyl]-amine (MS m/e: 297.2 [M+H]$^+$) was prepared from 3-bromo-anisol instead of 6-bromo-2,3-dihydro-benzofuran and 2-(5-trifluoromethyl-pyridin-2-yl)-ethylamine instead of 2-(6-trifluoromethyl-pyridin-3-yl)-ethylamine.

b) Step 2:

(R,S)-Acetic acid (4-fluoro-phenyl)-{(3-methoxy-phenyl)-[2-(5-trifluoromethyl-pyridin-2-yl)-ethyl]-carbamoyl}-methyl ester

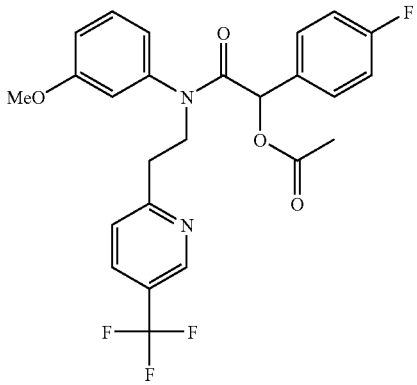

In analogy to the procedure described for the synthesis example 7 (step 1), the title compound (R,S)-acetic acid (4-fluoro-phenyl)-{(3-methoxy-phenyl)-[2-(5-trifluoromethyl-pyridin-2-yl)-ethyl]-carbamoyl}-methyl ester (MS m/e: 491.2 [M+H]$^+$) was prepared from (3-methoxy-phenyl)-[2-(5-trifluoromethyl-pyridin-2-yl)-ethyl]-amine instead of (3,4-dimethyl-phenyl)-[2-(6-trifluoromethyl-pyridin-3-yl)-ethyl]-amine and (R,S)-acetoxy-(4-fluoro-phenyl)-acetic acid instead of (4-fluoro-phenyl)-oxo-acetic acid.

c) Step 3:

(R,S)-2-(4-Fluoro-phenyl)-2-hydroxy-N-(3-methoxy-phenyl)-N-[2-(5-trifluoromethyl-pyridin-2-yl)-ethyl]-acetamide In analogy to the procedure described for the synthesis example 73 (step 3), the title compound (R,S)-2-(4-fluoro-phenyl)-2-hydroxy-N-(3-methoxy-phenyl)-N-[2-(5-trifluoromethyl-pyridin-2-yl)-ethyl]-acetamide (MS m/e: 449.2 [M+H]$^+$) was prepared from (R,S)-acetic acid (4-fluoro-phenyl)-{(3-methoxy-phenyl)-[2-(5-trifluoromethyl-pyridin-2-yl)-ethyl]-carbamoyl}-methyl ester instead of (R,S)-acetic acid (4-fluoro-phenyl)-{indan-5-yl-[2-(5-trifluoromethyl-pyridin-2-yl)-ethyl]-carbamoyl}-methyl ester.

EXAMPLE 77

(R,S)—N-(4-Fluoro-3-methyl-phenyl)-2-(4-fluoro-phenyl)-2-hydroxy-N-[2-(5-trifluoromethyl-pyridin-2-yl)-ethyl]-acetamide

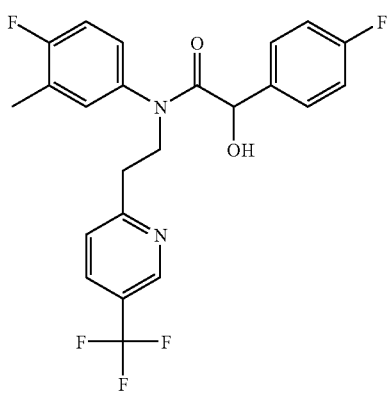

a) Step 1:

(4-Fluoro-3-methyl-phenyl)-[2-(5-trifluoromethyl-pyridin-2-yl)-ethyl]-amine

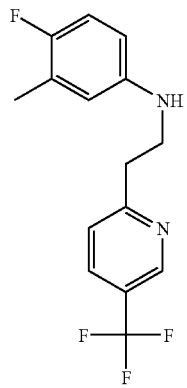

In analogy to the procedure described for the synthesis example 71 (step 1), the title compound (4-fluoro-3-methyl-phenyl)-[2-(5-trifluoromethyl-pyridin-2-yl)-ethyl]-amine (MS m/e: 299.3 [M+H]$^+$) was prepared from 5-bromo-2-fluorotoluene instead of 6-bromo-2,3-dihydro-benzofuran and 2-(5-trifluoromethyl-pyridin-2-yl)-ethylamine instead of 2-(6-trifluoromethyl-pyridin-3-yl)-ethylamine.

b) Step 2:

(R,S)—N-(4-Fluoro-3-methyl-phenyl)-2-(4-fluoro-phenyl)-2-hydroxy-N-[2-(5-trifluoromethyl-pyridin-2-yl)-ethyl]-acetamide To a solution of (4-fluoro-3-methyl-phenyl)-[2-(5-trifluoromethyl-pyridin-2-yl)-ethyl]-amine (193 mg, 0.65 mmol) and (R,S)-acetoxy-(4-fluoro-phenyl)-acetic acid (151 mg, 0.71 mmol) in dichloromethane (4 mL) was added 1-(3-dimethylaminopropyl)-3-ethylcarbodiimide hydrochloride (136 mg, 0.71 mmol) at 0° C. After stirring for 3.5 h at 0° C., the reaction mixture was washed with aqueous sodium carbonate (saturated, 20 ml) and water (20 ml). The aqueous layers were extracted with dichloromethane (30 ml). The combined organic layers were dried over sodium sulfate and concentrated. This intermediate was treated with lithium hydroxide monohydrate (30 mg, 0.71 mmol), THF (3.0 ml) and water (1.5 ml) and stirred for 18 h at ambient temperature. It was diluted with water (20 ml), and extracted with ethyl acetate (40 ml).

The organic layers were combined and dried over sodium sulfate. Concentration and purification by chromatography (SiO$_2$, heptane:ethyl acetate=100:0 to 67:33) afforded the title compound (268 mg, 92%) as a colorless oil. MS m/e: 451.2 [M+H]$^+$.

EXAMPLE 78

(R,S)—N-(3-Fluoro-4-methyl-phenyl)-2-(4-fluoro-phenyl)-2-hydroxy-N-[2-(5-trifluoromethyl-pyridin-2-yl)-ethyl]-acetamide

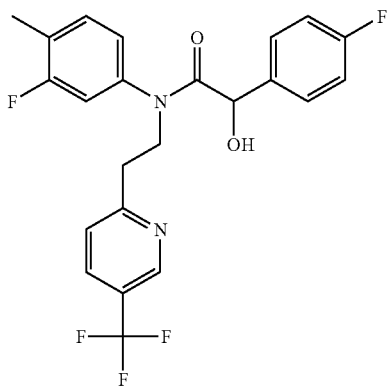

a) Step 1:

(3-Fluoro-4-methyl-phenyl)-[2-(5-trifluoromethyl-pyridin-2-yl)-ethyl]-amine

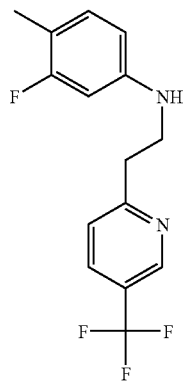

In analogy to the procedure described for the synthesis example 71 (step 1), the title compound (3-fluoro-4-methyl-phenyl)-[2-(5-trifluoromethyl-pyridin-2-yl)-ethyl]-amine (MS m/e: 299.3 [M+H]$^+$) was prepared from 4-bromo-2-fluorotoluene instead of 6-bromo-2,3-dihydro-benzofuran and 2-(5-trifluoromethyl-pyridin-2-yl)-ethylamine instead of 2-(6-trifluoromethyl-pyridin-3-yl)-ethylamine.

b) Step 2:

(R,S)—N-(3-Fluoro-4-methyl-phenyl)-2-(4-fluoro-phenyl)-2-hydroxy-N-[2-(5-trifluoromethyl-pyridin-2-yl)-ethyl]-acetamide In analogy to the procedure described for the synthesis example 77 (step 2), the title compound (R,S)—N-(3-fluoro-4-methyl-phenyl)-2-(4-fluoro-phenyl)-2-hydroxy-N-[2-(5-trifluoromethyl-pyridin-2-yl)-ethyl]-acetamide (MS m/e: 451.2 [M+H]$^+$) was prepared from (3-fluoro-4-methyl-phenyl)-[2-(5-trifluoromethyl-pyridin-2-yl)-ethyl]-amine instead of (4-fluoro-3-methyl-phenyl)-[2-(5-trifluoromethyl-pyridin-2-yl)-ethyl]-amine.

EXAMPLE 79

(R,S)—N-(4-Chloro-3-methoxy-phenyl)-2-(4-fluoro-phenyl)-2-hydroxy-N-[2-(5-trifluoromethyl-pyridin-2-yl)-ethyl]-acetamide

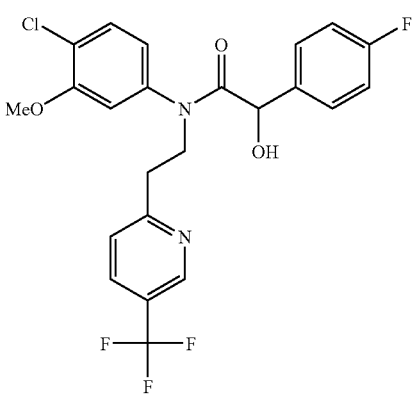

a) Step 1:

(4-Chloro-3-methoxy-phenyl)-[2-(5-trifluoromethyl-pyridin-2-yl)-ethyl]-amine

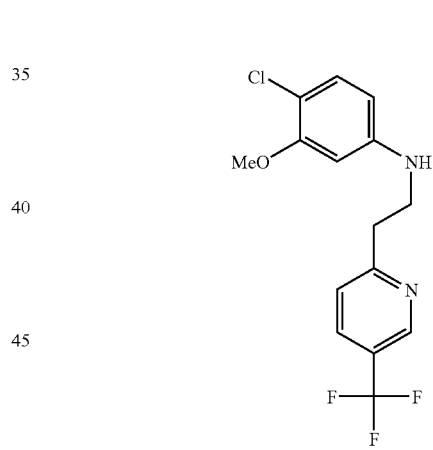

In analogy to the procedure described for the synthesis example 71 (step 1), the title compound (4-chloro-3-methoxy-phenyl)-[2-(5-trifluoromethyl-pyridin-2-yl)-ethyl]-amine (MS m/e: 331.1 [M+H]$^+$) was prepared from 5-bromo-2-chloro-anisol instead of 6-bromo-2,3-dihydro-benzofuran and 2-(5-trifluoromethyl-pyridin-2-yl)-ethylamine instead of 2-(6-trifluoromethyl-pyridin-3-yl)-ethylamine.

b) Step 2:

(R,S)—N-(4-Chloro-3-methoxy-phenyl)-2-(4-fluoro-phenyl)-2-hydroxy-N-[2-(5-trifluoromethyl-pyridin-2-yl)-ethyl]-acetamide In analogy to the procedure described for the synthesis example 77 (step 2), the title compound (R,S)—N-(4-chloro-3-methoxy-phenyl)-2-(4-fluoro-phenyl)-2-hydroxy-N-[2-(5-trifluoromethyl-pyridin-2-yl)-ethyl]-acetamide (MS m/e:

483.1 [M+H]⁺) was prepared from (4-chloro-3-methoxy-phenyl)-[2-(5-trifluoromethyl-pyridin-2-yl)-ethyl]-amine instead of (4-fluoro-3-methyl-phenyl)-[2-(5-trifluoromethyl-pyridin-2-yl)-ethyl]-amine.

EXAMPLE 80

(S)—N-(3-Fluoro-4-methyl-phenyl)-2-(4-fluoro-phenyl)-2-hydroxy-N-[2-(5-trifluoromethyl-pyridin-2-yl)-ethyl]-acetamide

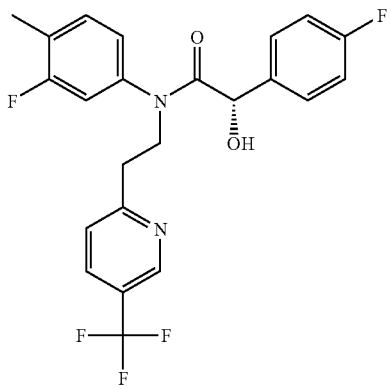

(R,S)—N-(3-Fluoro-4-methyl-phenyl)-2-(4-fluoro-phenyl)-2-hydroxy-N-[2-(5-trifluoromethyl-pyridin-2-yl)-ethyl]-acetamide was separated on chiral phase HPLC (Chiralpak AD column) to provide the title compound (S)—N-(3-fluoro-4-methyl-phenyl)-2-(4-fluoro-phenyl)-2-hydroxy-N-[2-(5-trifluoromethyl-pyridin-2-yl)-ethyl]-acetamide (MS m/e: 451.2 [M+H]⁺) as a colorless oil.

EXAMPLE 81

(S)—N-(4-Fluoro-3-methyl-phenyl)-2-(4-fluoro-phenyl)-2-hydroxy-N-[2-(5-trifluoromethyl-pyridin-2-yl)-ethyl]-acetamide

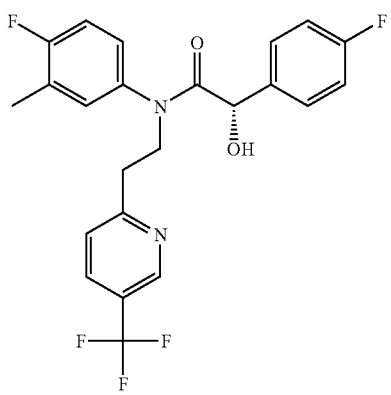

(R,S)—N-(4-Fluoro-3-methyl-phenyl)-2-(4-fluoro-phenyl)-2-hydroxy-N-[2-(5-trifluoromethyl-pyrisin-2-yl)-ethyl]-acetamide was separated on chiral phase HPLC (Chiralpak AD column) to provide the title compound (S)—N-(4-fluoro-3-methyl-phenyl)-2-(4-fluoro-phenyl)-2-hydroxy-N-[2-(5-trifluoromethyl-pyridin-2-yl)-ethyl]-acetamide (MS m/e: 451.2 [M+H]⁺) as a colorless oil.

EXAMPLE 82

(R,S)—N-(4-Ethyl-phenyl)-2-(4-fluoro-phenyl)-2-hydroxy-N-[2-(5-trifluoromethyl-pyridin-2-yl)-ethyl]-acetamide

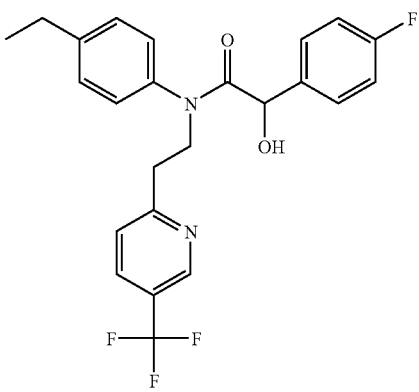

a) Step 1:

(4-Ethyl-phenyl)-[2-(5-trifluoromethyl-pyridin-2-yl)-ethyl]-amine

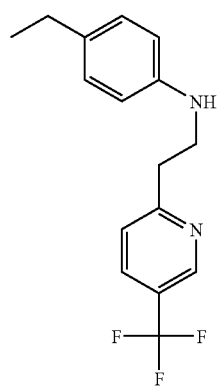

In analogy to the procedure described for the synthesis example 71 (step 1), the title compound (4-ethyl-phenyl)-[2-(5-trifluoromethyl-pyridin-2-yl)-ethyl]-amine (MS m/e: 295.2 [M+H]⁺) was prepared from 1-bromo-4-ethyl-benzene instead of 6-bromo-2,3-dihydro-benzofuran and 2-(5-trifluoromethyl-pyridin-2-yl)-ethylamine instead of 2-(6-trifluoromethyl-pyridin-3-yl)-ethylamine.

b) Step 2:

(R,S)—N-(4-Ethyl-phenyl)-2-(4-fluoro-phenyl)-2-hydroxy-N-[2-(5-trifluoromethyl-pyridin-2-yl)-ethyl]-acetamide In analogy to the procedure described for the synthesis example 77 (step 2), the title compound (R,S)—N-(4-ethyl-phenyl)-2-(4-fluoro-phenyl)-2-hydroxy-N-[2-(5-trifluoromethyl-pyridin-2-yl)-ethyl]-acetamide (MS m/e: 447.2

[M+H]⁺) was prepared from (4-ethyl-phenyl)-[2-(5-trifluoromethyl-pyridin-2-yl)-ethyl]-amine instead of (4-fluoro-3-methyl-phenyl)-[2-(5-trifluoromethyl-pyridin-2-yl)-ethyl]-amine.

EXAMPLE 83

(R,S)-2-(4-Fluoro-phenyl)-2-hydroxy-N-(4-methyl-3-oxo-3,4-dihydro-2H-benzo[1,4]oxazin-6-yl)-N-[2-(5-trifluoromethyl-pyridin-2-yl)-ethyl]-acetamide

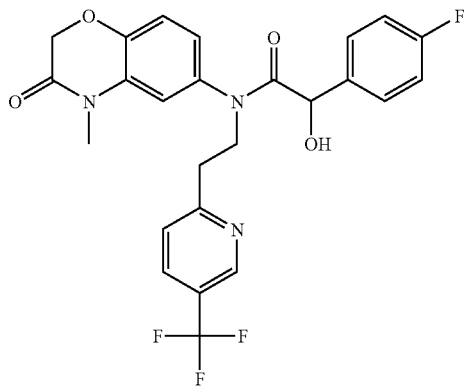

a) Step 1:

4-Methyl-6-[2-(5-trifluoromethyl-pyridin-2-yl)-ethylamino]-4H-benzo[1,4]oxazin-3-one

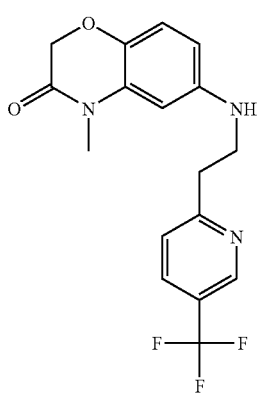

In analogy to the procedure described for the synthesis example 71 (step 1), the title compound 4-methyl-6-[2-(5-trifluoromethyl-pyridin-2-yl)-ethylamino]-4H-benzo[1,4]oxazin-3-one (MS m/e: 352.2 [M+H]⁺) was prepared from 6-bromo-4-methyl-4H-benzo[1,4]oxazin-3-one instead of 6-bromo-2,3-dihydro-benzofuran and 2-(5-trifluoromethyl-pyridin-2-yl)-ethylamine instead of 2-(6-trifluoromethyl-pyridin-3-yl)-ethylamine.

b) Step 2:

(R,S)-2-(4-Fluoro-phenyl)-2-hydroxy-N-(4-methyl-3-oxo-3,4-dihydro-2H-benzo[1,4]oxazin-6-yl)-N-[2-(5-trifluoromethyl-pyridin-2-yl)-ethyl]-acetamide In analogy to the procedure described for the synthesis example 77 (step 2), the title compound (R,S)-2-(4-fluoro-phenyl)-2-hydroxy-N-(4-methyl-3-oxo-3,4-dihydro-2H-benzo[1,4]oxazin-6-yl)-N-[2-(5-trifluoromethyl-pyridin-2-yl)-ethyl]-acetamide (MS m/e: 504.1 [M+H]⁺) was prepared from 4-methyl-6-[2-(5-trifluoromethyl-pyridin-2-yl)-ethylamino]-4H-benzo[1,4]oxazin-3-one instead of (4-fluoro-3-methyl-phenyl)-[2-(5-trifluoromethyl-pyridin-2-yl)-ethyl]-amine.

EXAMPLE 84

(R,S)-2-(4-Fluoro-phenyl)-2-hydroxy-N-(1-methyl-2-oxo-1,2,3,4-tetrahydro-quinolin-6-yl)-N-[2-(5-trifluoromethyl-pyridin-2-yl)-ethyl]-acetamide

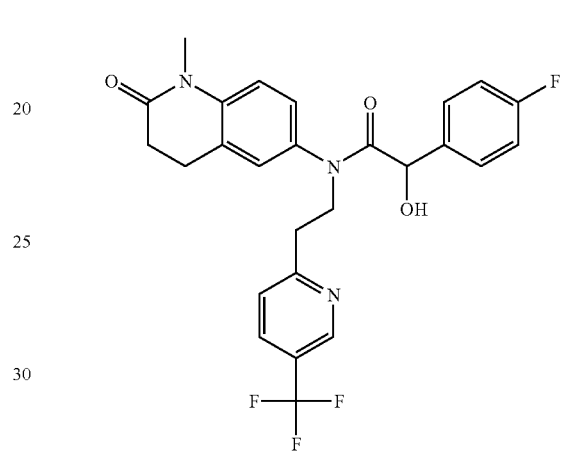

a) Step 1:

1-Methyl-6-[2-(5-trifluoromethyl-pyridin-2-yl)-ethylamino]-3,4-dihydro-1H-quinolin-2-one

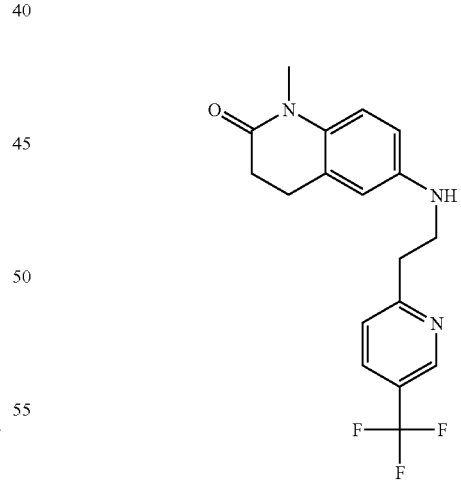

In analogy to the procedure described for the synthesis example 71 (step 1), the title compound 1-methyl-6-[2-(5-trifluoromethyl-pyridin-2-yl)-ethylamino]-3,4-dihydro-1H-quinolin-2-one (MS m/e: 350.3 [M+H]⁺) was prepared from 6-bromo-1-methyl-3,4-dihydro-1H-quinolin-2-one instead of 6-bromo-2,3-dihydro-benzofuran and 2-(5-trifluoromethyl-pyridin-2-yl)-ethylamine instead of 2-(6-trifluoromethyl-pyridin-3-yl)-ethylamine.

b) Step 2:

(R,S)-2-(4-Fluoro-phenyl)-2-hydroxy-N-(1-methyl-2-oxo-1,2,3,4-tetrahydro-quinolin-6-yl)-N-[2-(5-trifluoromethyl-pyridin-2-yl)-ethyl]-acetamide In analogy to the procedure described for the synthesis example 77 (step 2), the title compound (R,S)-2-(4-fluoro-phenyl)-2-hydroxy-N-(1-methyl-2-oxo-1,2,3,4-tetrahydro-quinolin-6-yl)-N-[2-(5-trifluoromethyl-pyridin-2-yl)-ethyl]-acetamide (MS m/e: 502.1 [M+H]$^+$) was prepared from 1-methyl-6-[2-(5-trifluoromethyl-pyridin-2-yl)-ethylamino]-3,4-dihydro-1H-quinolin-2-one instead of (4-fluoro-3-methyl-phenyl)-[2-(5-trifluoromethyl-pyridin-2-yl)-ethyl]-amine.

EXAMPLE 85

(S)-2-(4-Fluoro-phenyl)-2-hydroxy-N-(3-methoxy-phenyl)-N-[2-(5-trifluoromethyl-pyridin-2-yl)-ethyl]-acetamide

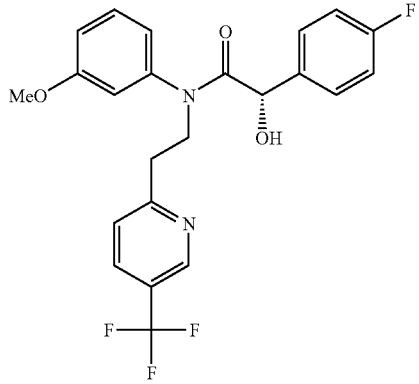

(R,S)-2-(4-Fluoro-phenyl)-2-hydroxy-N-(3-methoxy-phenyl)-N-[2-(5-trifluoromethyl-pyridin-2-yl)-ethyl]-acetamide was separated on chiral phase HPLC (Chiralpak AD column) to provide the title compound (S)-2-(4-fluoro-phenyl)-2-hydroxy-N-(3-methoxy-phenyl)-N-[2-(5-trifluoromethyl-pyridin-2-yl)-ethyl]-acetamide (MS m/e: 449.2 [M+H]$^+$) as a colorless oil.

EXAMPLE 86

(S)-2-(4-Fluoro-phenyl)-2-hydroxy-N-indan-5-yl-N-[2-(5-trifluoromethyl-pyridin-2-yl)-ethyl]-acetamide

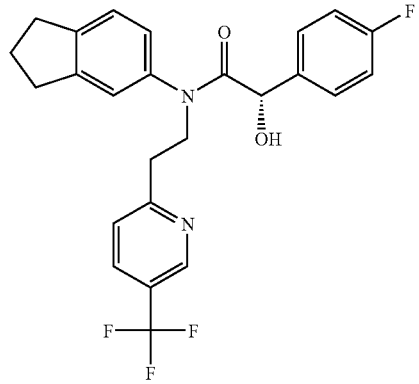

(R,S)-2-(4-Fluoro-phenyl)-2-hydroxy-N-indan-5-yl-N-[2-(5-trifluoromethyl-pyridin-2-yl)-ethyl]-acetamide was separated on chiral phase HPLC (Chiralpak AD column) to provide the title compound (S)-2-(4-fluoro-phenyl)-2-hydroxy-N-indan-5-yl-N-[2-(5-trifluoromethyl-pyridin-2-yl)-ethyl]-acetamide (MS m/e: 459.2 [M+H]$^+$) as a colorless oil.

EXAMPLE 87

(S)—N-(2,3-Dihydro-benzofuran-5-yl)-2-(4-fluoro-phenyl)-2-hydroxy-N-[2-(5-trifluoromethyl-pyridin-2-yl)-ethyl]-acetamide

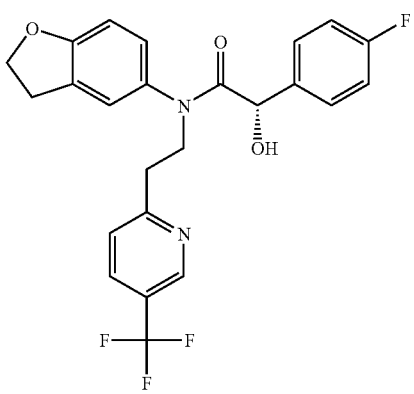

(R,S)—N-(2,3-Dihydro-benzofuran-5-yl)-2-(4-fluoro-phenyl)-2-hydroxy-N-[2-(5-trifluoromethyl-pyridin-2-yl)-ethyl]-acetamide was separated on chiral phase HPLC (Chiralpak AD column) to provide the title compound (S)—N-(2,3-dihydro-benzofuran-5-yl)-2-(4-fluoro-phenyl)-2-hydroxy-N-[2-(5-trifluoromethyl-pyridin-2-yl)-ethyl]-acetamide (MS m/e: 461.1 [M+H]$^+$) as a colorless oil.

EXAMPLE 88

(R,S)—N-(4-Fluoro-3-methoxy-phenyl)-2-(4-fluoro-phenyl)-2-hydroxy-N-[2-(5-trifluoromethyl-pyridin-2-yl)-ethyl]-acetamide

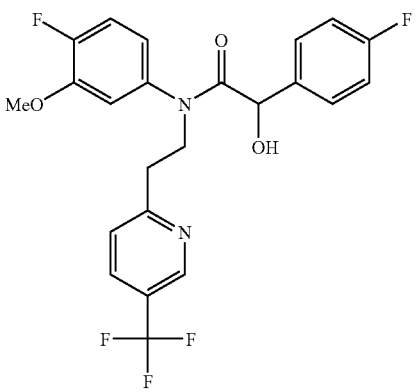

a) Step 1:

(4-Fluoro-3-methoxy-phenyl)-[2-(5-trifluoromethyl-pyridin-2-yl)-ethyl]-amine

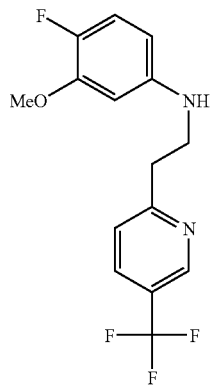

In analogy to the procedure described for the synthesis example 71 (step 1), the title compound (4-fluoro-3-methoxy-phenyl)-[2-(5-trifluoromethyl-pyridin-2-yl)-ethyl]-amine (MS m/e: 315.1 [M+H]$^+$) was prepared from 5-bromo-2-fluoro-anisole instead of 6-bromo-2,3-dihydro-benzofuran and 2-(5-trifluoromethyl-pyridin-2-yl)-ethylamine instead of 2-(6-trifluoromethyl-pyridin-3-yl)-ethylamine.

b) Step 2:

(R,S)—N-(4-Fluoro-3-methoxy-phenyl)-2-(4-fluoro-phenyl)-2-hydroxy-N-[2-(5-trifluoromethyl-pyridin-2-yl)-ethyl]-acetamide In analogy to the procedure described for the synthesis example 77 (step 2), the title compound (R,S)—N-(4-fluoro-3-methoxy-phenyl)-2-(4-fluoro-phenyl)-2-hydroxy-N-[2-(5-trifluoromethyl-pyridin-2-yl)-ethyl]-acetamide (MS m/e: 467.2 [M+H]$^+$) was prepared from (4-fluoro-3-methoxy-phenyl)-[2-(5-trifluoromethyl-pyridin-2-yl)-ethyl]-amine instead of (4-fluoro-3-methyl-phenyl)-[2-(5-trifluoromethyl-pyridin-2-yl)-ethyl]-amine.

EXAMPLE 89

(R,S)—N-(4-Cyclopropyl-phenyl)-2-(4-fluoro-phenyl)-2-hydroxy-N-[2-(5-trifluoromethyl-pyridin-2-yl)-ethyl]-acetamide

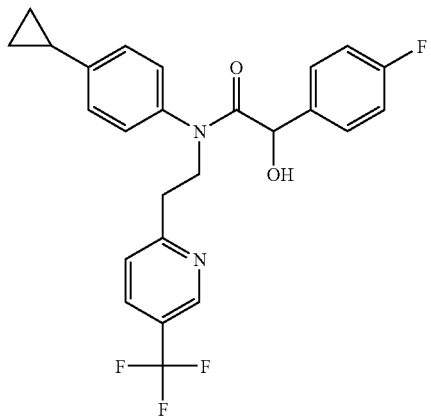

a) Step 1:

(4-Cyclopropyl-phenyl)-[2-(5-trifluoromethyl-pyridin-2-yl)-ethyl]-amine

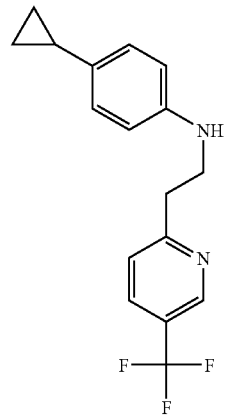

In analogy to the procedure described for the synthesis example 71 (step 1), the title compound (4-cyclopropyl-phenyl)-[2-(5-trifluoromethyl-pyridin-2-yl)-ethyl]-amine (MS m/e: 307.2 [M+H]$^+$) was prepared from 1-bromo-4-cyclopropyl-benzene instead of 6-bromo-2,3-dihydro-benzofuran and 2-(5-trifluoromethyl-pyridin-2-yl)-ethylamine instead of 2-(6-trifluoromethyl-pyridin-3-yl)-ethylamine.

b) Step 2:

(R,S)—N-(4-Cyclopropyl-phenyl)-2-(4-fluoro-phenyl)-2-hydroxy-N-[2-(5-trifluoromethyl-pyridin-2-yl)-ethyl]-acetamide In analogy to the procedure described for the synthesis example 77 (step 2), the title compound (R,S)—N-(4-cyclopropyl-phenyl)-2-(4-fluoro-phenyl)-2-hydroxy-N-[2-(5-trifluoromethyl-pyridin-2-yl)-ethyl]-acetamide (MS m/e: 459.2 [M+H]$^+$) was prepared from (4-cyclopropyl-phenyl)-[2-(5-trifluoromethyl-pyridin-2-yl)-ethyl]-amine instead of (4-fluoro-3-methyl-phenyl)-[2-(5-trifluoromethyl-pyridin-2-yl)-ethyl]-amine.

EXAMPLE 90

(R,S)—N-(4-Fluoro-3-hydroxymethyl-phenyl)-2-(4-fluoro-phenyl)-2-hydroxy-N-[2-(5-trifluoromethyl-pyridin-2-yl)-ethyl]-acetamide

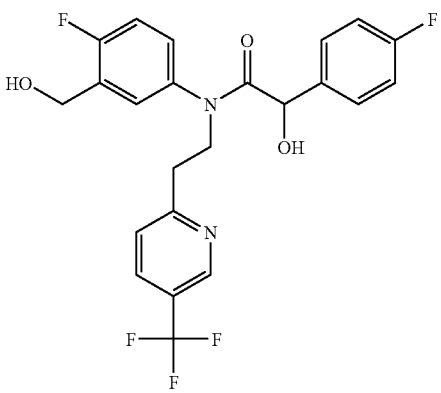

a) Step 1:

{2-Fluoro-5-[2-(5-trifluoromethyl-pyridin-2-yl)-ethylamino]-phenyl}-methanol

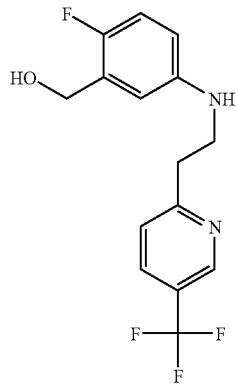

In analogy to the procedure described for the synthesis example 71 (step 1), the title compound {2-fluoro-5-[2-(5-trifluoromethyl-pyridin-2-yl)-ethylamino]-phenyl}-methanol (MS m/e: 315.1 [M+H]$^+$) was prepared from (5-bromo-2-fluoro-phenyl)-methanol instead of 6-bromo-2,3-dihydro-benzofuran and 2-(5-trifluoromethyl-pyridin-2-yl)-ethylamine instead of 2-(6-trifluoromethyl-pyridin-3-yl)-ethylamine.

b) Step 2:

(R,S)—N-(4-Fluoro-3-hydroxymethyl-phenyl)-2-(4-fluoro-phenyl)-2-hydroxy-N-[2-(5-trifluoromethyl-pyridin-2-yl)-ethyl]-acetamide In analogy to the procedure described for the synthesis example 77 (step 2), the title compound (R,S)—N-(4-fluoro-3-hydroxymethyl-phenyl)-2-(4-fluoro-phenyl)-2-hydroxy-N-[2-(5-trifluoromethyl-pyridin-2-yl)-ethyl]-acetamide (MS m/e: 467.2 [M+H]$^+$) was prepared from ({2-fluoro-5-[2-(5-trifluoromethyl-pyridin-2-yl)-ethylamino]-phenyl}-methanol instead of (4-fluoro-3-methyl-phenyl)-[2-(5-trifluoromethyl-pyridin-2-yl)-ethyl]-amine.

EXAMPLE 91

(R,S)—N-(4-Cyano-phenyl)-2-(4-fluoro-phenyl)-2-hydroxy-N-[2-(5-trifluoromethyl-pyridin-2-yl)-ethyl]-acetamide

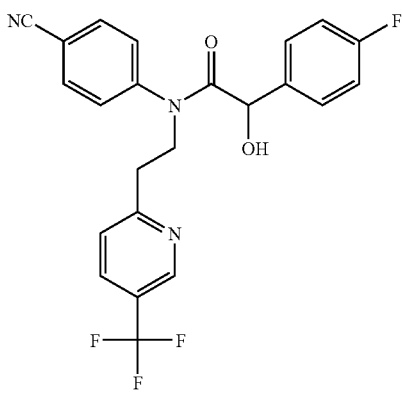

a) Step 1:

(4-Bromo-phenyl)-[2-(5-trifluoromethyl-pyridin-2-yl)-ethyl]-amine

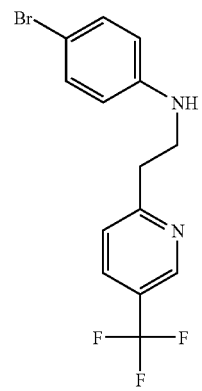

In analogy to the procedure described for the synthesis example 71 (step 1), the title compound (4-bromo-phenyl)-[2-(5-trifluoromethyl-pyridin-2-yl)-ethyl]-amine (MS m/e: 347.0 [M+H]$^+$) was prepared from 1-bromo-4-iodo-benzene instead of 6-bromo-2,3-dihydro-benzofuran and 2-(5-trifluoromethyl-pyridin-2-yl)-ethylamine instead of 2-(6-trifluoromethyl-pyridin-3-yl)-ethylamine.

b) Step 2:

(R,S)-Acetic acid {(4-bromo-phenyl)-[2-(5-trifluoromethyl-pyridin-2-yl)-ethyl]-carbamoyl}-(4-fluoro-phenyl)-methyl ester

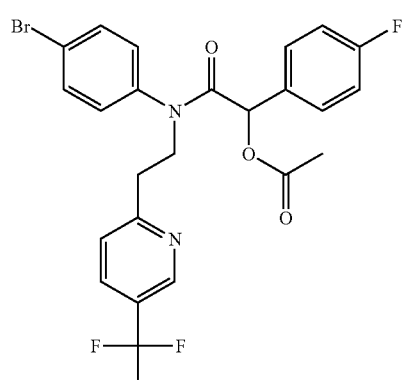

In analogy to the procedure described for the synthesis example 7 (step 1), the title compound (R,S)-acetic acid {(4-bromo-phenyl)-[2-(5-trifluoromethyl-pyridin-2-yl)-ethyl]-carbamoyl}-(4-fluoro-phenyl)-methyl ester (MS m/e: 541.1 [M+H]$^+$) was prepared from (4-bromo-phenyl)-[2-(5-trifluoromethyl-pyridin-2-yl)-ethyl]-amine instead of (3,4-dimethyl-phenyl)-[2-(6-trifluoromethyl-pyridin-3-yl)-ethyl]-amine and (R,S)-acetoxy-(4-fluoro-phenyl)-acetic acid instead of (4-fluoro-phenyl)-oxo-acetic acid.

c) Step 3:

(R,S)—N-(4-Cyano-phenyl)-2-(4-fluoro-phenyl)-2-hydroxy-N-[2-(5-trifluoromethyl-pyridin-2-yl)-ethyl]-acetamide

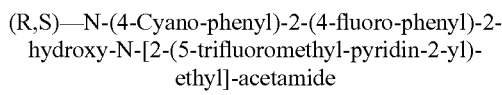

Under an atmosphere of nitrogen was added to a solution of (R,S)-acetic acid {(4-bromo-phenyl)-[2-(5-trifluoromethyl-pyridin-2-yl)-ethyl]-carbamoyl}-(4-fluoro-phenyl)-methyl ester (190 mg, 0.352 mmol) in NMP (2 mL) copper (I) cyanide (38 mg, 0.42 mmol) and the reaction mixture was stirred for 30 min at 150° C. Further copper(I) cyanide (88 mg, 0.989 mmol) was added and stirring was continued for 18 h at 150° C. The resulting mixture was cooled to ambient temperature, treated with water (1 mL) and lithium hydroxide monohydrate (30 mg, 0.70 mmol) and stirred for 24 h at ambient temperature.

The resulting dark brown mixture was diluted with TBME (15 mL) and washed with water (15 mL) and with aqueous sodium carbonate (saturated, 15 mL). The aqueous layers were extracted with TBME (15 mL) and dried over sodium sulfate. Concentration and purification by chromatography (SiO$_2$, heptane:ethyl acetate=80:20 to 50:50) afforded the title compound (33 mg, 21%) as a light brown oil. MS m/e: 444.2 [M+H]$^+$.

EXAMPLE 92

(S)—N-(4-Fluoro-3-methoxy-phenyl)-2-(4-fluoro-phenyl)-2-hydroxy-N-[2-(5-trifluoromethyl-pyridin-2-yl)-ethyl]-acetamide

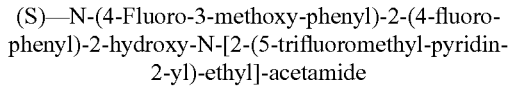

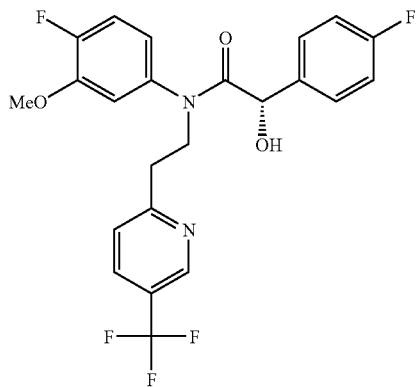

(R,S)—N-(4-Fluoro-3-methoxy-phenyl)-2-(4-fluoro-phenyl)-2-hydroxy-N-[2-(5-trifluoromethyl-pyridin-2-yl)-ethyl]-acetamide was separated on chiral phase HPLC (Chiralpak AD column) to provide the title compound (S)—N-(4-fluoro-3-methoxy-phenyl)-2-(4-fluoro-phenyl)-2-hydroxy-N-[2-(5-trifluoromethyl-pyridin-2-yl)-ethyl]-acetamide (MS m/e: 461.1 [M+H]$^+$) as a colorless viscous oil.

EXAMPLE 93

(R,S)-2-(4-Fluoro-phenyl)-2-hydroxy-N-(4-methoxy-3-methyl-phenyl)-N-[2-(5-trifluoromethyl-pyridin-2-yl)-ethyl]-acetamide

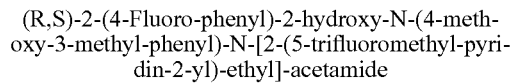

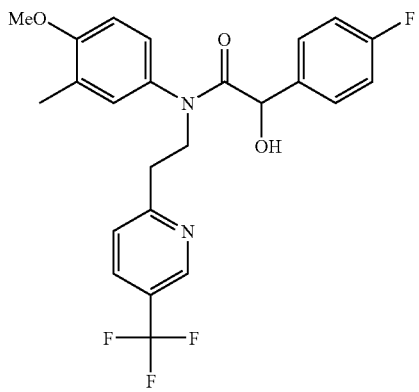

a) Step 1:

(4-Methoxy-3-methyl-phenyl)-[2-(5-trifluoromethyl-pyridin-2-yl)-ethyl]-amine

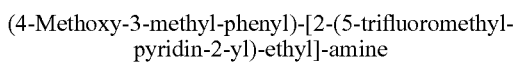

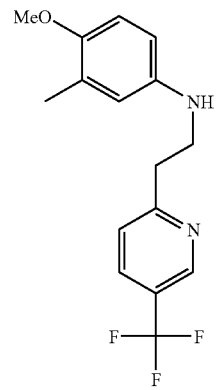

In analogy to the procedure described for the synthesis example 71 (step 1), the title compound (4-methoxy-3-methyl-phenyl)-[2-(5-trifluoromethyl-pyridin-2-yl)-ethyl]-amine (MS m/e: 311.3 [M+H]$^+$) was prepared from 4-bromo-2-methyl-anisole instead of 6-bromo-2,3-dihydro-benzofuran and 2-(5-trifluoromethyl-pyridin-2-yl)-ethylamine instead of 2-(6-trifluoromethyl-pyridin-3-yl)-ethylamine.

b) Step 2:

(R,S)-2-(4-Fluoro-phenyl)-2-hydroxy-N-(4-methoxy-3-methyl-phenyl)-N-[2-(5-trifluoromethyl-pyridin-2-yl)-ethyl]-acetamide

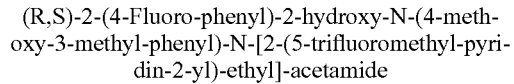

In analogy to the procedure described for the synthesis example 77 (step 2), the title compound (R,S)-2-(4-fluoro-phenyl)-2-hydroxy-N-(4-methoxy-3-methyl-phenyl)-N-[2-(5-trifluoromethyl-pyridin-2-yl)-ethyl]-acetamide (MS m/e: 463.2 [M+H]$^+$) was prepared from (4-methoxy-3-methyl-phenyl)-[2-(5-trifluoromethyl-pyridin-2-yl)-ethyl]-amine instead of (4-fluoro-3-methyl-phenyl)-[2-(5-trifluoromethyl-pyridin-2-yl)-ethyl]-amine.

EXAMPLE 94

(R,S)—N-(2,2-Dioxo-2,3-dihydro-1H-2lambda(6)-benzo[c]thiophen-5-yl)-2-(4-fluoro-phenyl)-2-hydroxy-N-[2-(5-trifluoromethyl-pyridin-2-yl)-ethyl]-acetamide

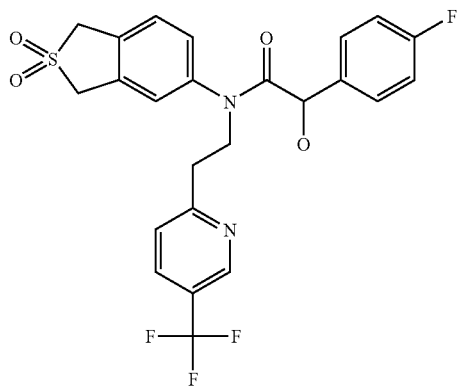

a) Step 1:

(2,2-Dioxo-2,3-dihydro-1H-2lambda(6)-benzo[c]thiophen-5-yl)-[2-(5-trifluoromethyl-pyridin-2-yl)-ethyl]-amine

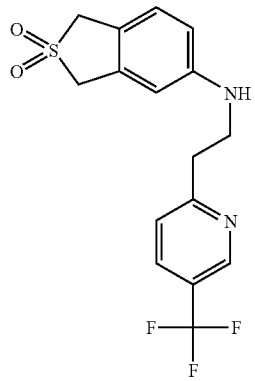

In analogy to the procedure described for the synthesis example 25 (step 1), the title compound (2,2-dioxo-2,3-dihydro-1H-2lambda(6)-benzo[c]thiophen-5-yl)-[2-(5-trifluoromethyl-pyridin-2-yl)-ethyl]-amine (MS m/e: 357.1 [M+H]$^+$) was prepared from 5-amino-2,3-dihydro-1H-2lambda(6)-benzo[c]thiophene-2,2-dione instead of 3,4-dimethylaniline and 5-trifluoromethyl-2-vinyl-pyridine.

b) Step 2:

(R,S)—N-(2,2-Dioxo-2,3-dihydro-1H-2lambda(6)-benzo[c]thiophen-5-yl)-2-(4-fluoro-phenyl)-2-hydroxy-N-[2-(5-trifluoromethyl-pyridin-2-yl)-ethyl]-acetamide In analogy to the procedure described for the synthesis example 77 (step 2), the title compound (R,S)—N-(2,2-dioxo-2,3-dihydro-1H-2lambda(6)-benzo[c]thiophen-5-yl)-2-(4-fluoro-phenyl)-2-hydroxy-N-[2-(5-trifluoromethyl-pyridin-2-yl)-ethyl]-acetamide (MS m/e: 509.1 [M+H]$^+$) was prepared from (4-methoxy-3-methyl-phenyl)-[2-(5-trifluoromethyl-pyridin-2-yl)-ethyl]-amine instead of (4-fluoro-3-methyl-phenyl)-[2-(5-trifluoromethyl-pyridin-2-yl)-ethyl]-amine.

EXAMPLE 95

(R,S)-N-(3-Difluoromethoxy-4-methyl-phenyl)-2-(4-fluoro-phenyl)-2-hydroxy-N-[2-(5-trifluoromethyl-pyridin-2-yl)-ethyl]-acetamide

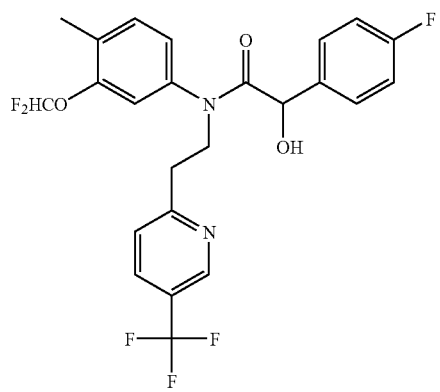

a) Step 1:

(3-Difluoromethoxy-4-methyl-phenyl)-[2-(5-trifluoromethyl-pyridin-2-yl)-ethyl]-amine

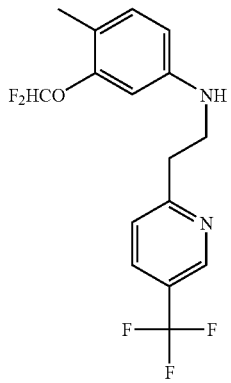

In analogy to the procedure described for the synthesis example 71 (step 1), the title compound (3-difluoromethoxy-4-methyl-phenyl)-[2-(5-trifluoromethyl-pyridin-2-yl)-ethyl]-amine (MS m/e: 347.1 [M+H]$^+$) was prepared from 4-iodo-2-difluoromethoxy-toluene instead of 6-bromo-2,3-dihydro-benzofuran and 2-(5-trifluoromethyl-pyridin-2-yl)-ethylamine instead of 2-(6-trifluoromethyl-pyridin-3-yl)-ethylamine.

b) Step 2:

(R,S)—N-(3-Difluoromethoxy-4-methyl-phenyl)-2-(4-fluoro-phenyl)-2-hydroxy-N-[2-(5-trifluoromethyl-pyridin-2-yl)-ethyl]-acetamide In analogy to the procedure described for the synthesis example 77 (step 2), the title compound (R,S)—N-(3-difluoromethoxy-4-methyl-phenyl)-2-(4-fluoro-phenyl)-2-hydroxy-N-[2-(5-trifluoromethyl-pyridin-2-yl)-ethyl]-acetamide (MS m/e: 499.2 [M+H]⁺) was prepared from (3-difluoromethoxy-4-methyl-phenyl)-[2-(5-trifluoromethyl-pyridin-2-yl)-ethyl]-amine instead of (4-fluoro-3-methyl-phenyl)-[2-(5-trifluoromethyl-pyridin-2-yl)-ethyl]-amine.

EXAMPLE 96

(R,S)—N-(3,4-Bis-difluoromethoxy-phenyl)-2-(4-fluoro-phenyl)-2-hydroxy-N-[2-(5-trifluoromethyl-pyridin-2-yl)-ethyl]-acetamide

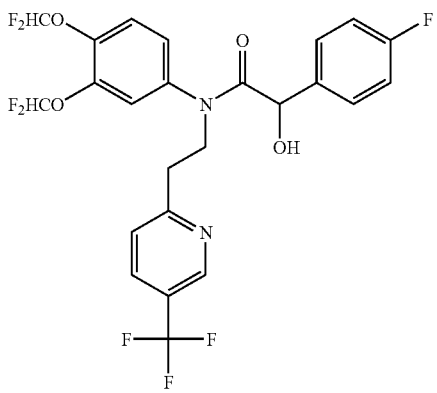

a) Step 1:

(3,4-Bis-difluoromethoxy-phenyl)-[2-(5-trifluoromethyl-pyridin-2-yl)-ethyl]-amine

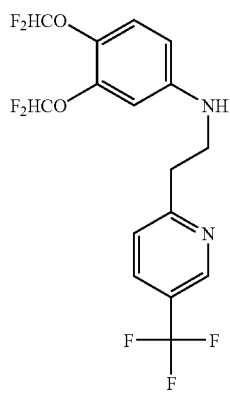

In analogy to the procedure described for the synthesis example 71 (step 1), the title compound (3,4-bis-difluoromethoxy-phenyl)-[2-(5-trifluoromethyl-pyridin-2-yl)-ethyl]-amine (MS m/e: 399.1 [M+H]⁺) was prepared from 1,2-bis-difluoromethoxy-4-iodo-benzene instead of 6-bromo-2,3-dihydro-benzofuran and 2-(5-trifluoromethyl-pyridin-2-yl)-ethylamine instead of 2-(6-trifluoromethyl-pyridin-3-yl)-ethylamine.

b) Step 2:

(R,S)—N-(3,4-Bis-difluoromethoxy-phenyl)-2-(4-fluoro-phenyl)-2-hydroxy-N-[2-(5-trifluoromethyl-pyridin-2-yl)-ethyl]-acetamide In analogy to the procedure described for the synthesis example 77 (step 2), the title compound (R,S)—N-(3,4-bis-difluoromethoxy-phenyl)-2-(4-fluoro-phenyl)-2-hydroxy-N-[2-(5-trifluoromethyl-pyridin-2-yl)-ethyl]-acetamide (MS m/e: 551.2 [M+H]⁺) was prepared from (3,4-bis-difluoromethoxy-phenyl)-[2-(5-trifluoromethyl-pyridin-2-yl)-ethyl]-amine instead of (4-fluoro-3-methyl-phenyl)-[2-(5-trifluoromethyl-pyridin-2-yl)-ethyl]-amine.

EXAMPLE 97

(R,S)-N-(4-Chloro-3-ethyl-phenyl)-2-(4-fluoro-phenyl)-2-hydroxy-N-[2-(5-trifluoromethyl-pyridin-2-yl)-ethyl]-acetamide

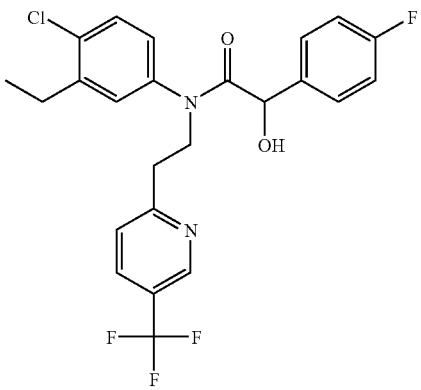

a) Step 1:

(4-Chloro-3-ethyl-phenyl)-[2-(5-trifluoromethyl-pyridin-2-yl)-ethyl]-amine

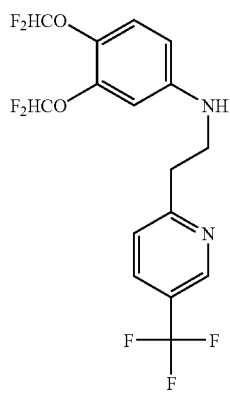

In analogy to the procedure described for the synthesis example 71 (step 1), the title compound (4-chloro-3-ethyl-phenyl)-[2-(5-trifluoromethyl-pyridin-2-yl)-ethyl]-amine (MS m/e: 329.2 [M+H]⁺) was prepared from 4-bromo-1-chloro-2-ethylbenzene instead of 6-bromo-2,3-dihydro-benzofuran and 2-(5-trifluoromethyl-pyridin-2-yl)-ethylamine instead of 2-(6-trifluoromethyl-pyridin-3-yl)-ethylamine.

b) Step 2:

(R,S)—N-(4-Chloro-3-ethyl-phenyl)-2-(4-fluoro-phenyl)-2-hydroxy-N-[2-(5-trifluoromethyl-pyridin-2-yl)-ethyl]-acetamide In analogy to the procedure described for the synthesis example 77 (step 2), the title compound (R,S)—N-(4-chloro-3-ethyl-phenyl)-2-(4-fluoro-phenyl)-2-hydroxy-N-[2-(5-trifluoromethyl-pyridin-2-yl)-ethyl]-acetamide (MS m/e: 481.2 [M+H]+) was prepared from (4-chloro-3-ethyl-phenyl)-[2-(5-trifluoromethyl-pyridin-2-yl)-ethyl]-amine instead of (4-fluoro-3-methyl-phenyl)-[2-(5-trifluoromethyl-pyridin-2-yl)-ethyl]-amine.

EXAMPLE 98

(R,S)—N-(4-Chloro-3-hydroxymethyl-phenyl)-2-(4-fluoro-phenyl)-2-hydroxy-N-[2-(5-trifluoromethyl-pyridin-2-yl)-ethyl]-acetamide

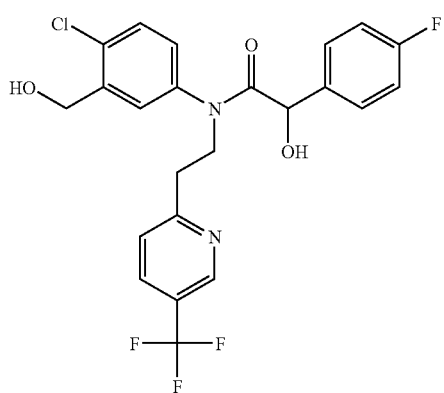

a) Step 1:

(5-Bromo-2-chloro-benzyloxy)-tert-butyl-dimethyl-silane

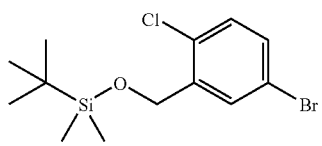

To a solution of 5-bromo-2-chlorobenzyl alcohol (3.00 g, 13.6 mmol) in DMF (10 ml) was added under a nitrogen atmosphere imidazole (2.89 g, 42.0 mmol). After cooling to 0° C. tert-butyldimethylchlorsilan (3.37 g, 22.3 mmol) was added and the reaction mixture was stirred for 18 h in a thawing ice bath. It was diluted with water (20 ml) and extracted with EtOAc (20 ml). The aqueous layer was extracted with ethyl acetate (20 ml) and the organic layers were washed with water (20 ml) and brine (20 ml) and were dried over sodium sulfate. Concentration and purification by chromatography (SiO₂, heptane:ethyl acetate=100:0 to 80:20) afforded the title compound (4.35 g, 96%) as a colorless liquid. MS m/e: 279.0 [M−tBu]+.

b) Step 2:

[3-(tert-Butyl-dimethyl-silanyloxymethyl)-4-chloro-phenyl]-[2-(5-trifluoromethyl-pyridin-2-yl)-ethyl]-amine

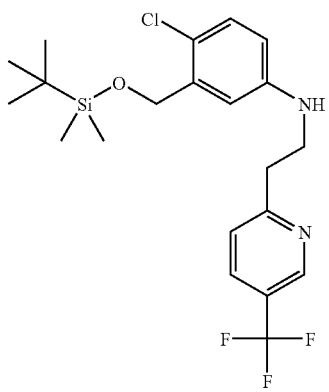

In analogy to the procedure described for the synthesis example 71 (step 1), the title compound [3-(tert-butyl-dimethyl-silanyloxymethyl)-4-chloro-phenyl]-[2-(5-trifluoromethyl-pyridin-2-yl)-ethyl]-amine (MS m/e: 445.3 [M+H]+) was prepared from (5-bromo-2-chloro-benzyloxy)-tert-butyl-dimethyl-silane instead of 6-bromo-2,3-dihydro-benzofuran and 2-(5-trifluoromethyl-pyridin-2-yl)-ethylamine instead of 2-(6-trifluoromethyl-pyridin-3-yl)-ethylamine.

c) Step 3:

(R,S)-Acetic acid {(4-chloro-3-hydroxymethyl-phenyl)-[2-(5-trifluoromethyl-pyridin-2-yl)-ethyl]-carbamoyl}-(4-fluoro-phenyl)-methyl ester

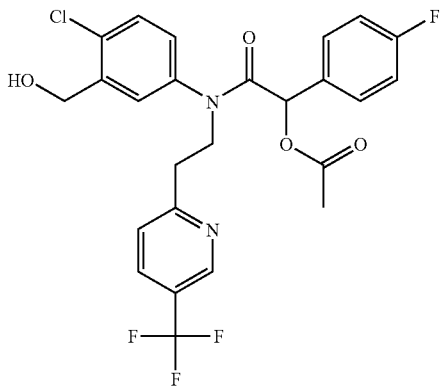

After cooling a solution of [3-(tert-butyl-dimethyl-silanyloxymethyl)-4-chloro-phenyl]-[2-(5-trifluoromethyl-pyridin-2-yl)-ethyl]-amine (400 mg, 0.894 mmol) in dichloromethane (4 ml) to 0° C. (R,S)-acetoxy-(4-fluoro-phenyl)-acetic acid (209 mg, 0.984 mmol) and 1-(3-dimethylaminopropyl)-3-ethylcarbodiimide hydrochloride (189 mg, 0.984 mmol) were added and reacted for 1 h at 0° C. and 2 h at ambient temperature. The reaction mixture was treated with hydrochloric acid (4 M in dioxane, 2.2 ml, 8.9 mmol) and stirred for 18 h at ambient temperature. The resulting light brown solution was diluted with TBME (10 ml) and basified by addition of aqueous sodium carbonate (saturated, 15 ml). The aqueous layer was extracted with TBME (15 ml) and dried over sodium sulfate. Concentration and purification by chromatography (SiO₂, heptane:ethyl acetate=70:30 to 40:60) afforded the title compound (452 mg, 96%) as a white semisolid. MS m/e: 525.3 [M+H]+ d) Step 4:

(R,S)—N-(4-Chloro-3-hydroxymethyl-phenyl)-2-(4-fluoro-phenyl)-2-hydroxy-N-[2-(5-trifluoromethyl-pyridin-2-yl)-ethyl]-acetamide

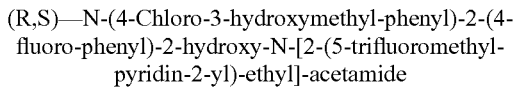

To a solution (R,S)-acetic acid {(4-chloro-3-hydroxymethyl-phenyl)-[2-(5-trifluoromethyl-pyridin-2-yl)-ethyl]-carbamoyl}-(4-fluoro-phenyl)-methyl ester (137 mg, 0.261 mmol) in THF (1 ml) and water (0.5 ml) was added lithium hydroxide monohydrate (12 mg, 0.29 mmol) and the reaction mixture was stirred for 24 h at ambient temperature.

The light brown solution was diluted with TBME (10 ml) and washed with brine (10 ml). The organic layer was dried over sodium sulfate. Concentration and purification by chromatography (SiO$_2$, heptane:ethyl acetate=70:30 to 40:60) afforded the title compound (72 mg, 57%) as a light brown oil. MS m/e: 483.1 [M+H]$^+$

EXAMPLE 99

(R,S)-2-Chloro-5-{[2-(4-fluoro-phenyl)-2-hydroxy-acetyl]-[2-(5-trifluoromethyl-pyridin-2-yl)-ethyl]-amino}-benzoic acid methyl ester

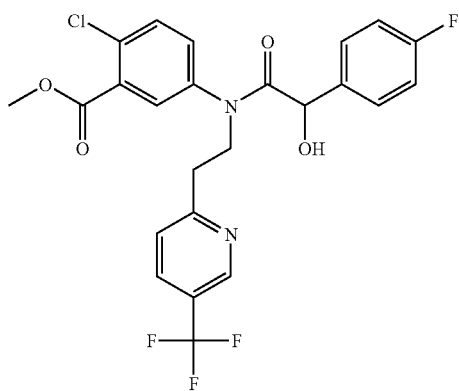

a) Step 1:

2-Chloro-5-[2-(5-trifluoromethyl-pyridin-2-yl)-ethylamino]-benzoic acid methyl ester

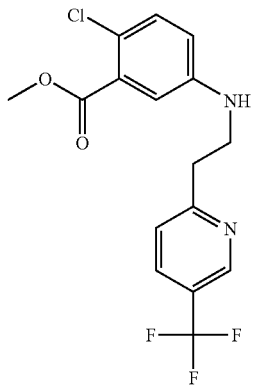

In a flask witch was protected with aluminium foil was placed (R,S)-acetic acid {(4-chloro-3-hydroxymethyl-phenyl)-[2-(5-trifluoromethyl-pyridin-2-yl)-ethyl]-carbamoyl}-(4-fluoro-phenyl)-methyl ester (337 mg, 0.642 mmol), calcium hypochlorite (459 mg, 3.21 mmol), acetic acid (367 µl, 6.42 mmol), methanol (859 µl, 21.2 mmol) and finely powdered molecular sieves (900 mg). The reaction mixture was stirred for 3 d at ambient temperature. After the addition of sodium thiosulfate pentahydrate (500 mg) it was stirred for 15 min at ambient temperature before it was diluted with TBME (15 ml) and washed with water (15 ml) and brine (15 ml). The aqueous layers were extracted with TBME (15 ml) and dried over sodium sulfate. After concentration, the residue was dissolved in methanol (3 ml) and sodium cyanide (115 mg, 2.34 mmol) was added. The reaction mixture was stirred for 15 min until the sodium cyanide went into solution. After the addition of manganese (IV) oxide (611 mg, 7.03 mmol) it was stirred for 18 h at ambient temperature. It was filtered over Hyflo® and washed with methanol. The filtrate was concentrated. Purification by chromatography (SiO$_2$, heptane:ethyl acetate=70:30 to 40:60) afforded the title compound (61 mg, 27%) as a light brown oil. MS m/e: 359.0 [M+H]$^+$ b) Step 2:

(R,S)-2-Chloro-5-{[2-(4-fluoro-phenyl)-2-hydroxy-acetyl]-[2-(5-trifluoromethyl-pyridin-2-yl)-ethyl]-amino}-benzoic acid methyl ester After cooling a solution of 2-chloro-5-[2-(5-trifluoromethyl-pyridin-2-yl)-ethylamino]-benzoic acid methyl ester (61 mg, 0.170 mmol) in dichloromethane (1 ml) to 0° C. (R,S)-acetoxy-(4-fluoro-phenyl)-acetic acid (40 mg, 0.19 mmol) and 1-(3-dimethylaminopropyl)-3-ethylcarbodiimide hydrochloride (36 mg, 0.19 mmol) was added and reacted for 1 h at 0° C. and 2 h at ambient temperature. The reaction mixture was treated with methylamine (41% solution in water, 287 µl, 3.40 mmol) and stirred for 3 d ambient temperature. The light brown solution was diluted with ethyl acetate (10 ml) and washed with brine (15 ml). The aqueous layer was extacted with ethyl acetate (15 ml). The combined organic layers were dried over sodium sulfate. Concentration and purification by chromatography (SiO$_2$, heptane:ethyl acetate=80:20 to 0:100) afforded the title compound (34 mg, 39%) as a white solid. MS m/e: 511.2 [M+H]$^+$

EXAMPLE 100

2-Chloro-5-{[2-(4-fluoro-phenyl)-2-oxo-acetyl]-[2-(5-trifluoromethyl-pyridin-2-yl)-ethyl]-amino}-N-methyl-benzamide

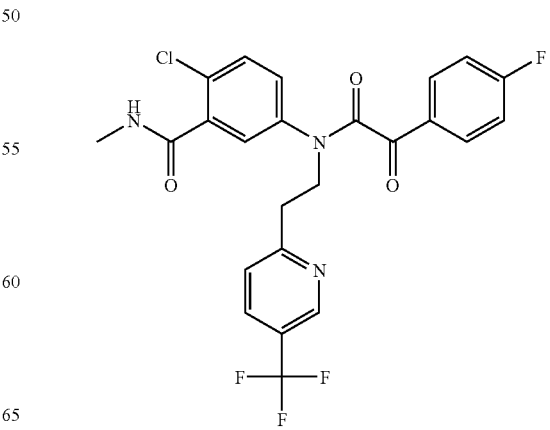

After cooling a solution of 2-chloro-5-[2-(5-trifluoromethyl-pyridin-2-yl)-ethylamino]-benzoic acid methyl ester (61 mg, 0.170 mmol) in dichloromethane (1 ml) to 0° C. (R,S)-acetoxy-(4-fluoro-phenyl)-acetic acid (40 mg, 0.19 mmol) and 1-(3-dimethylaminopropyl)-3-ethylcarbodiimide hydrochloride (36 mg, 0.19 mmol) was added and reacted for 1 h at 0° C. and 2 h at ambient temperature. The reaction mixture was treated with methylamine (41% solution in water, 287 μl, 3.40 mmol) and stirred for 3 d ambient temperature. The light brown solution was diluted with ethyl acetate (10 ml) and washed with brine (15 ml). The aqueous layer was extacted with ethyl acetate (15 ml). The combined organic layers were dried over sodium sulfate. Concentration and purification by chromatography (SiO$_2$, heptane:ethyl acetate=80:20 to 0:100) afforded the title compound (18 mg, 21%) as a light brown oil. MS m/e: 508.0 [M+H]$^+$

EXAMPLE 101

(S)-2-(4-Fluoro-phenyl)-2-hydroxy-N—((R or S)-4-hydroxy-chroman-6-yl)-N-[2-(6-trifluoromethyl-pyridin-3-yl)-ethyl]-acetamide

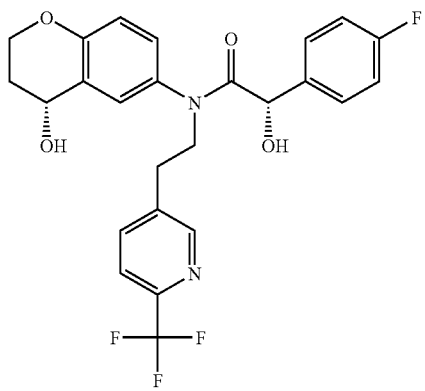

In analogy to example 7 (steps 1 & 2), 6-Amino-chroman-4-ol (WO 2003063794), (6-Trifluoromethyl-pyridin-3-yl)-acetonitrile & (4-fluoro-phenyl)-oxo-acetic acid were successively coupled then reduced to give after silica gel and chiral chromatography the target compound. MS(m/e): 491.1 [M+H]$^+$.

EXAMPLE 102

(S)-2-(4-Fluoro-phenyl)-2-hydroxy-N-((S or R)-4-hydroxy-chroman-6-yl)-N-[2-(6-trifluoromethyl-pyridin-3-yl)-ethyl]-acetamide

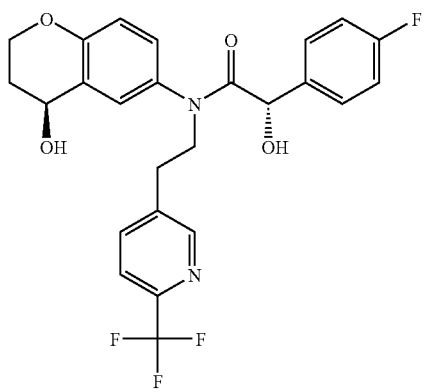

In analogy to example 7 (steps 1 & 2), 6-Amino-chroman-4-ol (WO 2003063794), (6-Trifluoromethyl-pyridin-3-yl)-acetonitrile & (4-fluoro-phenyl)-oxo-acetic acid were successively coupled then reduced to give after silica gel and chiral chromatography the target compound. MS(m/e): 491.1 [M+H]$^+$.

EXAMPLE 103

(R,S)—N-(4-Chloro-3-cyclopropoxy-phenyl)-2-(4-fluoro-phenyl)-2-hydroxy-N-[2-(5-trifluoromethyl-pyridin-2-yl)-ethyl]-acetamide

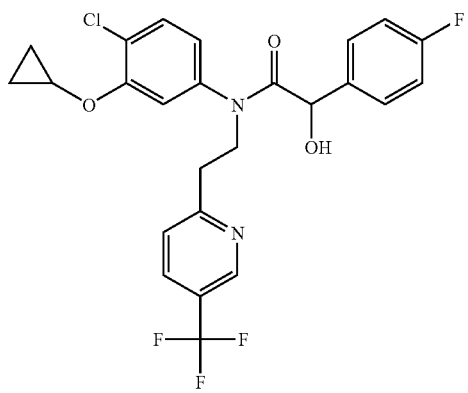

a) Step 1:

4-Bromo-1-chloro-2-cyclopropoxy-benzene

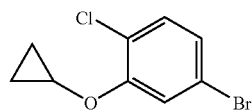

A mixture of 5-bromo-2-chlorophenol (543 mg, 2.62 mmol), bromocyclopropane (836 μl, 10.47 mmol) and caesium carbonate (1.701 g, 5.24 mmol) in N,N-dimethylacetamide (7.5 ml) was stirred for 47 h at 150° C. After 25.25 h further bromocyclopropane (836 μl, 10.47 mmol) was added. The reaction mixture was poured onto ice-water (40 ml) and set to pH=2 with aqueous HCl (1 N, 9.5 ml). This mixture was extracted with TBME (twice 50 ml). The organic layers were washed with brine (40 ml), combined and dried over sodium sulfate. Concentration and purification by chromatography (SiO$_2$, heptane:ethyl acetate=100:0 to 67:33) afforded the title compound (570 mg, 87%) as a light yellow oil. MS m/e: 248.0 [M+H]$^+$ b) Step 2:

(4-Chloro-3-cyclopropoxy-phenyl)-[2-(5-trifluoromethyl-pyridin-2-yl)-ethyl]-amine

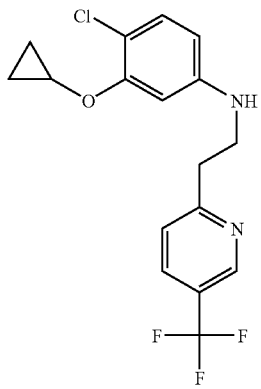

In analogy to the procedure described for the synthesis example 71 (step 1), the title compound (4-chloro-3-cyclopropoxy-phenyl)-[2-(5-trifluoromethyl-pyridin-2-yl)-ethyl]-amine (MS m/e: 357.1 [M+H]$^+$) was prepared from (4-bromo-1-chloro-2-cyclopropoxy-benzene instead of 6-bromo-2,3-dihydro-benzofuran and 2-(5-trifluoromethyl-pyridin-2-yl)-ethylamine instead of 2-(6-trifluoromethyl-pyridin-3-yl)-ethylamine.

c) Step 3:

(R,S)—N-(4-Chloro-3-cyclopropoxy-phenyl)-2-(4-fluoro-phenyl)-2-hydroxy-N-[2-(5-trifluoromethyl-pyridin-2-yl)-ethyl]-acetamide In analogy to the procedure described for the synthesis example 77 (step 2), the title compound (R,S)—N-(4-chloro-3-cyclopropoxy-phenyl)-2-(4-fluoro-phenyl)-2-hydroxy-N-[2-(5-trifluoromethyl-pyridin-2-yl)-ethyl]-acetamide (MS m/e: 509.1 [M+H]$^+$) was prepared from (4-chloro-3-cyclopropoxy-phenyl)-[2-(5-trifluoromethyl-pyridin-2-yl)-ethyl]-amine instead of (4-fluoro-3-methyl-phenyl)-[2-(5-trifluoromethyl-pyridin-2-yl)-ethyl]-amine.

EXAMPLE 104

(S)-2-Hydroxy-2-phenyl-N-quinolin-3-yl-N-[2-(4-trifluoromethyl-phenyl)-ethyl]-acetamide

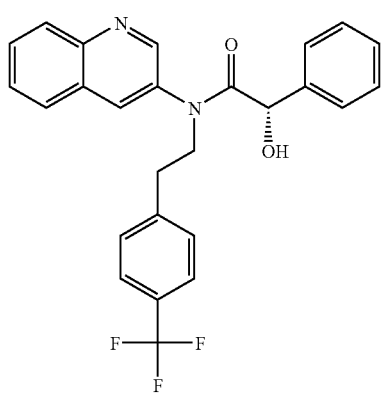

a) Step 1:

Quinolin-3-yl-[2-(4-trifluoromethyl-phenyl)-ethyl]-amine

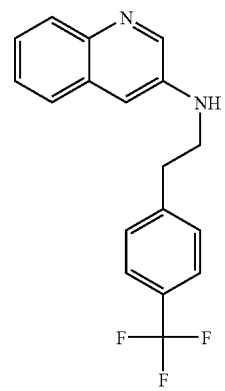

A solution of 10.4 mmol 4-(trifluoromethyl)phenylacetonitrile (commercially available) and 3.5 eq. aminoquinoline in MeOH (10 mL) was treated with ammonium formate (5 eq.) and 10% Pd/C (100 mg) and stirred at 80° C. for 2 h. Filtration, concentration and purification by chromatography (SiO$_2$, CH$_2$Cl$_2$/MeOH) afforded the title compound (73%) as a yellow oil. MS m/e: 317.1 [M+H]$^+$.

b) Step 2:

Acetic acid (S)-phenyl-{quinolin-3-yl-[2-(4-trifluoromethyl-phenyl)-ethyl]-carbamoyl}-methyl ester

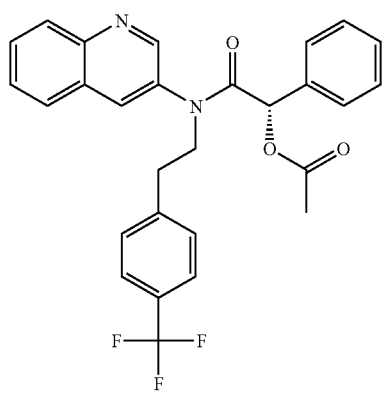

To a solution of 0.32 mmol Quinolin-3-yl-[2-(4-trifluoromethyl-phenyl)-ethyl]-amine in dry CH$_2$Cl$_2$ was added 0.35 mmol (+)-O-Acetyl-L-Mandelic Acid, 0.35 mmol 2-chloro-1-methylpyridinium iodide and 0.63 mmol of Et$_3$N and the reaction mixture stirred for 16 h at rt. The solution was washed once with a saturated NaHCO$_3$ solution and once with water. The washings were extracted once with dichloromethane. The combined organic layers were dried over Na$_2$SO$_4$, filtered and concentrated in vacuo. The crude oil (155 mg) was used directly for the next step.

c) Step 3:

(S)-2-Hydroxy-2-phenyl-N-quinolin-3-yl-N-[2-(4-trifluoromethyl-phenyl)-ethyl]-acetamide To a solution of 155 mg acetic acid (S)-phenyl-{quinolin-3-yl-[2-(4-trifluoromethyl-phenyl)-ethyl]-carbamoyl}-methyl ester in tetrahydrofuran (6.0 mL) were added 3.0 mL water and 20 mg lithium hydroxide monohydrate. The mixture was stirred at room temperature for 2 h. The mixture was diluted with water and extracted 3 times with ethyl acetate. The combined organic layers were dried over $Na_2SO_4$, filtered and concentrated in vacuo. The crude oil was purified with flash column chromatography on silica eluting with a gradient formed from heptane and ethylacetate to provide the title compound. MS(m/e): 451.1 $[M+H]^+$.

EXAMPLE 105

(S)-2-Hydroxy-2-phenyl-N-quinolin-6-yl-N-[2-(4-trifluoromethyl-phenyl)-ethyl]-acetamide

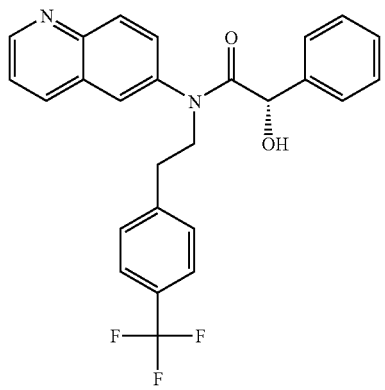

In analogy to example 104 quinolin-6-ylamine, 4-(trifluoromethyl)phenylacetonitrile & (+)-O-Acetyl-L-Mandelic Acid were successively coupled then hydrolysed to give after silica gel chromatography the target compound. MS(m/e): 451.1 $[M+H]^+$.

EXAMPLE 106

(S)-2-(4-Fluoro-phenyl)-2-hydroxy-N-(3-methyl-1H-indazol-5-yl)-N-[2-(6-trifluoromethyl-pyridin-3-yl)-ethyl]-acetamide

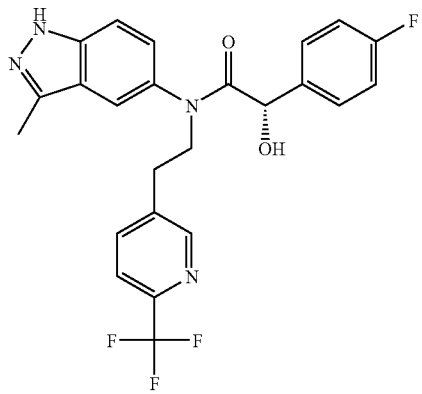

In analogy to example 47, 3-Methyl-1H-indazol-5-ylamine, (6-Trifluoromethyl-pyridin-3-yl)-acetonitrile & (4-fluoro-phenyl)-oxo-acetic acid were successively coupled then reduced to give after silica gel and chiral chromatography the target compound. MS(m/e): 473.1 $[M+H]^+$.

EXAMPLE 107

(S)—N-(1,3-Dimethyl-1H-indazol-5-yl)-2-(4-fluoro-phenyl)-2-hydroxy-N-[2-(6-trifluoromethyl-pyridin-3-yl)-ethyl]-acetamide

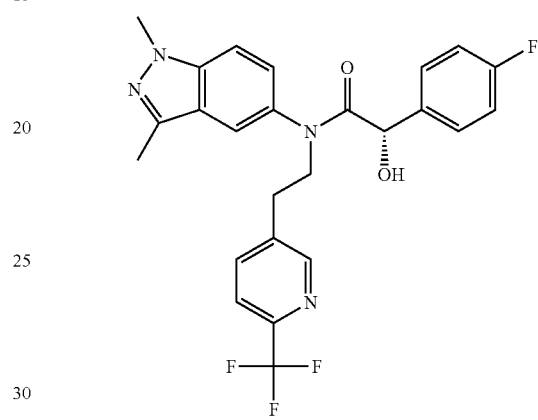

a) Step 1

2-(4-Fluoro-phenyl)-N-(3-methyl-1H-indazol-5-yl)-2-oxo-N-[2-(6-trifluoromethyl-pyridin-3-yl)-ethyl]-acetamide

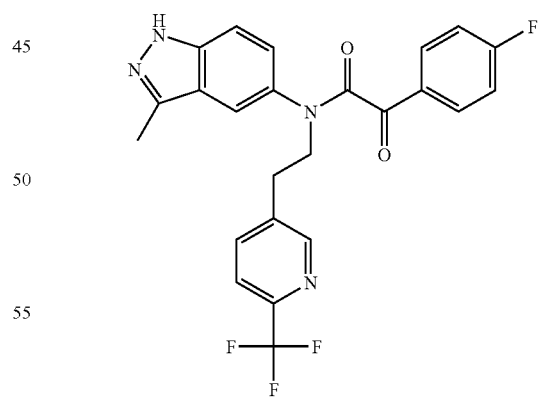

In analogy to example 47 (steps 1-3), 3-Methyl-1H-indazol-5-ylamine, (6-Trifluoromethyl-pyridin-3-yl)-acetonitrile & (4-fluoro-phenyl)-oxo-acetic acid were successively coupled to give after silica gel chromatography the target compound. MS(m/e): 471.1 $[M+H]^+$.

b) Step 2

N-(1,3-Dimethyl-1H-indazol-5-yl)-2-(4-fluoro-phenyl)-2-oxo-N-[2-(6-trifluoromethyl-pyridin-3-yl)-ethyl]-acetamide

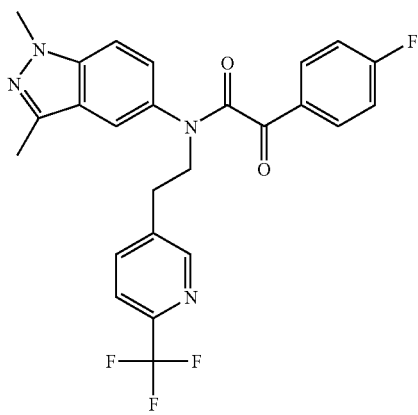

To a solution of 0.32 mmol 2-(4-Fluoro-phenyl)-N-(3-methyl-1H-indazol-5-yl)-2-oxo-N-[2-(6-trifluoromethyl-pyridin-3-yl)-ethyl]-acetamide (step 1) in 5 ml dry DMF was added 1.1 eq. NaH and the RM stirred at RT for 30 min. 5 eq. MeI was added and stirring continued for 5 h. Addition of 5 ml H$_2$O, concentration, repartitioning between EtOAc and H$_2$O, gave after separation of the layers and concentration the target compound (157 mg) MS(m/e): 485.1 [M+H]$^+$ which was used directly for the next step.

c) Step 3:

(S)—N-(1,3-Dimethyl-1H-indazol-5-yl)-2-(4-fluoro-phenyl)-2-hydroxy-N-[2-(6-trifluoromethyl-pyridin-3-yl)-ethyl]-acetamide In analogy to example 47 (step 4), N-(1,3-dimethyl-1H-indazol-5-yl)-2-(4-fluoro-phenyl)-2-oxo-N-[2-(6-trifluoromethyl-pyridin-3-yl)-ethyl]-acetamide was reduced to give after silica gel and chiral chromatography the target compound. MS(m/e): 487.1 [M+H]$^+$.

The invention claimed is:

1. A compound of formula

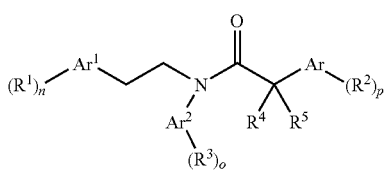

I wherein
i) Ar$^1$ is heteroaryl;
   Ar$^2$ is phenyl and
   Ar is phenyl or heteroaryl; or
ii) Ar$^1$ is phenyl;
    Ar$^2$ is heteroaryl and
    Ar is phenyl or heteroaryl; or
iii) Ar$^1$ is heteroaryl;
     Ar$^2$ is heteroaryl and
     Ar is phenyl or heteroaryl;

R$^1$ is hydrogen, halogen, lower alkyl, lower alkyl substituted by halogen or lower alkoxy;
R$^2$ is hydrogen, halogen, lower alkyl, lower alkyl substituted by halogen, lower alkoxy or lower alkoxy substituted by halogen;
each R$^3$ is independently hydrogen, halogen, lower alkyl, lower alkyl substituted by halogen, lower alkyl substituted by hydroxy, lower alkyl substituted by cycloalkyl, C(O)O-lower alkyl, C(O)NH-lower alkyl, —(CH$_2$)$_m$—O-lower alkyl, lower alkoxy, lower alkoxy substituted by halogen, cyano, SO$_2$-lower alkyl, cycloalkyl, or
where Ar$^2$ is phenyl and o is 2, R$^3$ optionally is R$^3$ and R$^{3'}$ which together with the corresponding carbon atoms to which they are attached form a non aromatic ring containing the groups —(CH$_2$)$_4$—, —(CH$_2$)$_3$—, —CH$_2$—S(O)$_2$—CH$_2$—, —N(CH$_3$)—C(O)—N(CH$_3$)—, —(CH$_2$)$_2$—O—, —O—(CH$_2$)$_2$—O—, —O—(CH$_2$)$_2$—CH(OH)—, —O—(CH$_2$)$_2$—, —O—(CH$_2$)$_3$—, —O—CH$_2$—C(O)—N(CH$_3$)—, —N(CH$_3$)—C(O)—(CH$_2$)$_2$—, or —O—C(CH$_3$)$_2$—O—;
R$^4$ and R$^5$ are each independently hydrogen, hydroxy, lower alkyl, lower alkoxy, CH$_2$NH$_2$, O—C(O)-lower alkyl, or —NRR' or R$^4$ and R$^5$ together are =O;
R and R' are each independently hydrogen, —S(O)$_2$-lower alkyl, cycloalkyl, —(CH$_2$)$_m$—OH, —(CH$_2$)$_m$—O-lower alkyl, —C(O)CH(NH$_2$)-phenyl, or oxetan-3-yl optionally substituted by CH$_2$NH$_2$, or
R and R' together with the N atom to which they are attached form a heterocycloalkyl ring, optionally containing in addition to the N atom a further heteroatom, selected from the group consisting of N, S and O;
n is 1, 2 or 3;
o is 1, 2 or 3;
p is 1, 2 or 3; and
m is 0, 1 or 2;
or a pharmaceutically suitable acid addition salt, optically pure enantiomer, racemate or diastereomeric mixture thereof.

2. The compound of claim 1 having formula IA

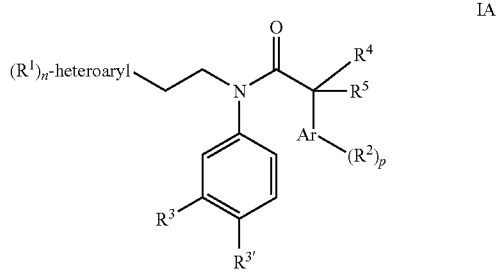

IA wherein
Ar is phenyl or heteroaryl;
R$^1$ is hydrogen, halogen, lower alkyl, lower alkyl substituted by halogen or lower alkoxy;
R$^2$ is hydrogen, halogen, lower alkyl, lower alkyl substituted by halogen, lower alkoxy or lower alkoxy substituted by halogen;
R$^3$ and R$^{3'}$ are each independently hydrogen, halogen, lower alkyl, lower alkyl substituted by halogen, lower alkyl substituted by hydroxy, lower alkyl substituted by cycloalkyl, C(O)O-lower alkyl, C(O)NH-lower alkyl, —(CH$_2$)$_m$-O-lower alkyl, lower alkoxy, lower alkoxy substituted by halogen, cyano, SO$_2$-lower alkyl, or cycloalkyl, or R³ and R³' together with the corresponding carbon atoms to which they are attached form a non aromatic ring containing the groups —(CH₂)₄—, —(CH₂)₃—, —CH₂—S(O)₂—CH₂—, —N(CH₃)—C(O)—N(CH₃)—, —(CH₂)₂—O—, —O—(CH₂)₂—O—, —O—(CH₂)₂—CH(OH)—, —O—(CH₂)₂—, —O—(CH₂)₃—, —O—CH₂—C(O)—N(CH₃)—, —N(CH₃)—C(O)—(CH₂)₂—, or —O—C(CH₃)₂—O—;

R⁴ and R⁵ are each independently hydrogen, hydroxy, lower alkyl, lower alkoxy, CH₂NH₂, O—C(O)-lower alkyl, or —NRR' or R⁴ and R⁵ together are =O;

R and R' are each independently hydrogen, —S(O)₂-lower alkyl, cycloalkyl, —(CH₂)ₘ—OH, —(CH₂)ₘ—O-lower alkyl,—C(O)CH(NH₂)-phenyl, or oxetan-3-yl optionally substituted by CH₂NH₂, or R and R' together with the N atom to which they are attached form a heterocycloalkyl ring, optionally containing in addition to the N atom a further heteroatom, selected from the group consisting of N, S and O;

n is 1, 2 or 3;
p is 1, 2 or 3; and
m is 0, 1 or 2;

or a pharmaceutically suitable acid addition salt, optically pure enantiomer, racemate or diastereomeric mixture thereof.

3. The compound of claim 2, selected from the group consisting of
(S)-2-amino-N-(3,4-dimethyl-phenyl)-2-phenyl-N-[2-(6-trifluoromethyl-pyridin-3-yl)-ethyl]-acetamide;
(S)—N-(3,4-dimethyl-phenyl)-2-hydroxy-2-phenyl-N-[2-(6-trifluoromethyl-pyridin-3-yl)-ethyl]-acetamide;
(R)—N-(3,4-dimethyl-phenyl)-2-hydroxy-2-phenyl-N-[2-(6-trifluoromethyl-pyridin-3-yl)-ethyl]-acetamide;
(S)-2-((S)-2-amino-2-phenyl-acetylamino)-N-(3,4-dimethoxy-phenyl)-2-phenyl-N-[2-(6-trifluoromethyl-pyridin-3-yl)-ethyl]-acetamide;
(S)-2-amino-N-(3,4-dimethoxy-phenyl)-2-phenyl-N-[2-(6-trifluoromethyl-pyridin-3-yl)-ethyl]-acetamide;
(S)—N-(3,4-dimethyl-phenyl)-2-(4-fluoro-phenyl)-2-hydroxy-N-[2-(6-trifluoromethyl-pyridin-3-yl)-ethyl]-acetamide;
(S)-2-(3-aminomethyl-oxetan-3-ylamino)-N-(3,4-dimethyl-phenyl)-2-phenyl-N-[2-(6-trifluoromethyl-pyridin-3-yl)-ethyl]acetamide;
(S)-2-amino-2-phenyl-N-(5,6,7,8-tetrahydro-naphthalen-2-yl)-N-[2-(6-trifluoromethyl-pyridin-3-yl)-ethyl]-acetamide;
(S)-2-amino-N-(3,4-dimethyl-phenyl)-2-(4-fluoro-phenyl)-N-[2-(6-trifluoromethyl-pyridin-3-yl)-ethyl]-acetamide;
(S)-2-hydroxy-2-phenyl-N-(5,6,7,8-tetrahydro-naphthalen-2-yl)-N-[2-(6-trifluoromethyl-pyridin-3-yl)-ethyl]-acetamide; and
(S)-2-hydroxy-2-phenyl-N-p-tolyl-N-[2-(6-trifluoromethyl-pyridin-3-yl)-ethyl]-acetamide.

4. The compound of claim 2, selected from the group consisting of
N-(3,4-dimethyl-phenyl)-2-phenyl-N-[2-(6-trifluoromethyl-pyridin-3-yl)-ethyl]-acetamide;
(S)-2-hydroxy-N-(3-methoxy-4-methyl-phenyl)-2-phenyl-N-[2-(6-trifluoromethyl-pyridin-3-yl)-ethyl]-acetamide;
N-(3,4-dimethyl-phenyl)-2-oxo-2-phenyl-N-[2-(6-trifluoromethyl-pyridin-3-yl)-ethyl]-acetamide;
(S)-2-amino-N-(3,4-dimethyl-phenyl)-N-[2-(5-methyl-pyridin-2-yl)-ethyl]-2-phenyl-acetamide;
(S)—N-(3,4-dimethyl-phenyl)-2-phenyl-N-[2-(6-trifluoromethyl-pyridin-3-yl)-ethyl]-propionamide;
(S)-2-amino-N-(3,4-dimethyl-phenyl)-2-phenyl-N-[2-(5-trifluoromethyl-pyridin-2-yl)-ethyl]-acetamide;
(S)—N-(3,4-dimethyl-phenyl)-2-hydroxy-2-phenyl-N-[2-(5-trifluoromethyl-pyridin-2-yl)-ethyl]-acetamide;
(R,S)—N-(3,4-dimethyl-phenyl)-2-hydroxy-2-phenyl-N-[2-(6-trifluoromethyl-pyridin-3-yl)-ethyl]-propionamide;
(S)—N-(2,3-dihydro-benzo[1,4]dioxin-6-yl)-2-hydroxy-2-phenyl-N-[2-(6-trifluoromethyl-pyridin-3-yl)-ethyl]-acetamide;
(S)-2-hydroxy-N-(3-methoxy-phenyl)-2-phenyl-N-[2-(6-trifluoromethyl-pyridin-3-yl)-ethyl]-acetamide; and
(S)—N-(3,4-dimethyl-phenyl)-2-(oxetan-3-ylamino)-2-phenyl-N-[2-(6-trifluoromethyl-pyridin-3-yl)-ethyl]-acetamide.

5. The compound of claim 2, selected from the group consisting of
(S)-2-hydroxy-N-(3-methoxy-phenyl)-2-phenyl-N-[2-(6-trifluoromethyl-pyridin-3-yl)-ethyl]-acetamide;
(S)-2-(4-fluoro-phenyl)-2-hydroxy-N-(5,6,7,8-tetrahydro-naphthalen-2-yl)-N-[2-(6-trifluoromethyl-pyridin-3-yl)-ethyl]-acetamide;
(S)-2-(4-fluoro-phenyl)-2-hydroxy-N-(3-methoxy-4-methyl-phenyl)-N-[2-(6-trifluoromethyl-pyridin-3-yl)-ethyl]-acetamide;
(S)-2-(4-fluoro-phenyl)-2-hydroxy-N-(3-methoxy-4-methyl-phenyl)-N-[2-(6-trifluoromethyl-pyridin-3-yl)-ethyl]-acetamide;
(S)-2-hydroxy-N-((S)-4-hydroxy-chroman-6-yl)-2-phenyl-N-[2-(6-trifluoromethyl-pyridin-3-yl)-ethyl]-acetamide;
acetic acid (S)-{(3,4-dimethyl-phenyl)-[2-(5-trifluoromethyl-pyridin-2-yl)-ethyl]-carbamoyl}-phenyl-methyl Ester;
(S)—N-[2-(5-chloro-pyridin-2-yl)-ethyl]-N-(3,4-dimethyl-phenyl)-2-hydroxy-2-phenyl-acetamide;
(S)-2-amino-N-(3,4-dimethyl-phenyl)-N-[2-(4-methyl-thiazol-2-yl)-ethyl]-2-phenyl-acetamide;
(S)—N-(3,4-dimethyl-phenyl)-N-[2-(5-fluoro-pyridin-2-yl)-ethyl]-2-hydroxy-2-phenyl-acetamide;
(S)—N-(3,4-dimethyl-phenyl)-2-hydroxy-N-[2-(3-methyl-isoxazol-5-yl)-ethyl]-2-phenyl-acetamide; and
(R,S)-2-(4-fluoro-phenyl)-2-hydroxy-N-indan-5-yl-N-[2-(5-trifluoromethyl-pyridin-2-yl)-ethyl]-acetamide.

6. The compound of claim 2, selected from the group consisting of
(R,S)—N-(2,3-dihydro-benzofuran-5-yl)-2-(4-fluoro-phenyl)-2-hydroxy-N-[2-(5-trifluoromethyl-pyridin-2-yl)-ethyl]-acetamide;
(R,S)-2-(4-fluoro-phenyl)-2-hydroxy-N-(3-methoxy-phenyl)-N-[2-(5-trifluoromethyl-pyridin-2-yl)-ethyl]-acetamide;;
(R,S)—N-(4-fluoro-3-methyl-phenyl)-2-(4-fluoro-phenyl)-2-hydroxy-N-[2-(5-trifluoromethyl-pyridin-2-yl)-ethyl]-acetamide;
(R,S)—N-(3-fluoro-4-methyl-phenyl)-2-(4-fluoro-phenyl)-2-hydroxy-N-[2-(5-trifluoromethyl-pyridin-2-yl)-ethyl]-acetamide;
(R,S)—N-(4-chloro-3-methoxy-phenyl)-2-(4-fluoro-phenyl)-2-hydroxy-N-[2-(5-trifluoromethyl-pyridin-2-yl)-ethyl]-acetamide;
(S)—N-(3-fluoro-4-methyl-phenyl)-2-(4-fluoro-phenyl)-2-hydroxy-N-[2-(5-trifluoromethyl-pyridin-2-yl)-ethyl]-acetamide;

(S)—N-(4-fluoro-3-methyl-phenyl)-2-(4-fluoro-phenyl)-2-hydroxy-N-[2-(5-trifluoromethyl-pyridin-2-yl)-ethyl]-acetamide;

(S)-2-(4-fluoro-phenyl)-2-hydroxy-N-indan-5-yl-N-[2-(5-trifluoromethyl-pyridin-2-yl)-ethyl]-acetamide;

(S)—N-(2,3-dihydro-benzofuran-5-yl)-2-(4-fluoro-phenyl)-2-hydroxy-N-[2-(5-trifluoromethyl-pyridin-2-yl)-ethyl]-acetamide;

(R,S)—N-(4-fluoro-3-methoxy-phenyl)-2-(4-fluoro-phenyl)-2-hydroxy-N-[2-(5-trifluoromethyl-pyridin-2-yl)-ethyl]-acetamide; and (R,S)—N-(4-fluoro-3-hydroxymethyl-phenyl)-2-(4-fluoro-phenyl)-2-hydroxy-N-[2-(5-trifluoromethyl-pyridin-2-yl)-ethyl]-acetamide.

7. The compound of claim 2, selected from the group consisting of (S)—N-(4-fluoro-3-methoxy-phenyl)-2-(4-fluoro-phenyl)-2-hydroxy-N-[2-(5-trifluoromethyl-pyridin-2-yl)-ethyl]-acetamide;

(R,S)-2-(4-fluoro-phenyl)-2-hydroxy-N-(4-methoxy-3-methyl-phenyl)-N-[2-(5-trifluoromethyl-pyridin-2-yl)-ethyl]-acetamide;

(R,S)—N-(3-difluoromethoxy-4-methyl-phenyl)-2-(4-fluoro-phenyl)-2-hydroxy-N-[2-(5-trifluoromethyl-pyridin-2-yl)-ethyl]-acetamide;

(R,S)—N-(3,4-bis-difluoromethoxy-phenyl)-2-(4-fluoro-phenyl)-2-hydroxy-N-[2-(5-trifluoromethyl-pyridin-2-yl)-ethyl]-acetamide;

(R,S)—N-(4-chloro-3-ethyl-phenyl)-2-(4-fluoro-phenyl)-2-hydroxy-N-[2-(5-trifluoromethyl-pyridin-2-yl)-ethyl]-acetamide;

(R,S)—N-(4-chloro-3-hydroxymethyl-phenyl)-2-(4-fluoro-phenyl)-2-hydroxy-N-[2-(5-trifluoromethyl-pyridin-2-yl)-ethyl]-acetamide;

(R,S)-2-chloro-5-{[2-(4-fluoro-phenyl)-2-hydroxy-acetyl]-[2-(5-trifluoromethyl-pyridin-2-yl)-ethyl]-amino}-benzoic acid methyl Ester;

(S)-2-(4-fluoro-phenyl)-2-hydroxy-N—((R or S)-4-hydroxy-chroman-6-yl)-N-[2-(6-trifluoromethyl-pyridin-3-yl)-ethyl]-acetamide;

(S)-2-(4-fluoro-phenyl)-2-hydroxy-N—((S or R)-4-hydroxy-chroman-6-yl)-N-[2-(6-trifluoromethyl-pyridin-3-yl)-ethyl]-acetamide; and (R,S)—N-(4-chloro-3-cyclopropoxy-phenyl)-2-(4-fluoro-phenyl)-2-hydroxy-N-[2-(5-trifluoromethyl-pyridin-2-yl)-ethyl]-acetamide.

8. The compound of claim 1 having formula IB

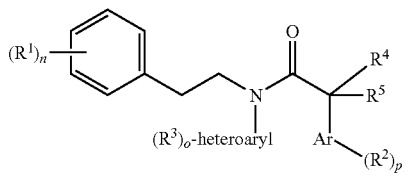

IB wherein

Ar is phenyl or heteroaryl;

$R^1$ is hydrogen, lower alkyl or lower alkyl substituted by halogen;

$R^2$ is hydrogen, halogen or lower alkoxy;

each $R^3$ is independently hydrogen, halogen, lower alkyl, lower alkyl substituted by halogen, lower alkyl substituted by hydroxy, lower alkyl substituted by cycloalkyl, C(O)O-lower alkyl, C(O)NH-lower alkyl, —(CH$_2$)$_m$—O-lower alkyl, lower alkoxy, lower alkoxy substituted by halogen, cyano, SO$_2$-lower alkyl or cycloalkyl;

$R^4$ and $R^5$ are each independently hydrogen, hydroxy, or —NRR' or $R^4$ and $R^5$ together are =O;

R and R' are each independently hydrogen, —S(O)$_2$-lower alkyl, cycloalkyl, —(CH$_2$)$_m$—OH, —(CH$_2$)$_m$—O-lower alkyl, —C(O)CH(NH$_2$)-phenyl, or oxetan-3-yl optionally substituted by CH$_2$NH$_2$, or R and R' together with the N atom to which they are attached form a heterocycloalkyl ring, optionally containing in addition to the N atom a further heteroatom, selected from the group consisting of N, S and O;

n is 1, 2 or 3;

o is 1, 2 or 3;

p is 1, 2 or 3; and m is 0, 1 or 2;

or a pharmaceutically suitable acid addition salt, optically pure enantiomer, racemate or diastereomeric mixture thereof.

9. The compound of claim 8, selected from the group consisting of (R,S)-2-amino-2-(4-chloro-phenyl)-N-(2,4-dimethyl-thiazol-5-yl)-N-(2-p-tolyl-ethyl)-acetamide;

(R,S)-2-amino-N-(6-methoxy-pyridin-3-yl)-2-phenyl-N-[2-(4-trifluoromethyl-phenyl)-ethyl]-acetamide;

(R,S)-2-amino-2-(4-chloro-phenyl)-N-(2,5-dimethyl-2H-pyrazol-3-yl)-N-[2-(4-trifluoromethyl-phenyl)-ethyl]-acetamide; and (R,S)—N-(2,5-dimethyl-2H-pyrazol-3-yl)-2-hydroxy-2-phenyl-N-[2-(4-trifluoromethyl-phenyl)-ethyl]-acetamide.

10. A compound of claim 1 having formula IC

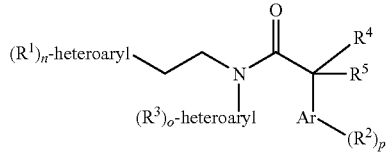

IC wherein

Ar is phenyl or heteroaryl;

$R^1$ is hydrogen, halogen, lower alkyl, lower alkyl substituted by halogen or lower alkoxy;

$R^2$ is hydrogen, halogen, lower alkyl, lower alkyl substituted by halogen, lower alkoxy or lower alkoxy substituted by halogen;

each $R^3$ is independently hydrogen, halogen, lower alkyl, lower alkyl substituted by halogen, lower alkyl substituted by hydroxy, lower alkyl substituted by cycloalkyl, C(O)O-lower alkyl, C(O)NH-lower alkyl, —(CH$_2$)$_m$—O-lower alkyl, lower alkoxy, lower alkoxy substituted by halogen, cyano, SO$_2$-lower alkyl or cycloalkyl;

$R^4$ and $R^5$ are each independently hydrogen, hydroxy, lower alkyl, lower alkoxy, CH$_2$NH$_2$, O—C(O)-lower alkyl, or —NRR' or $R^4$ and $R^5$ together are =O;

R and R' are each independently hydrogen, —S(O)$_2$-lower alkyl, cycloalkyl, —(CH$_2$)$_m$—OH, —(CH$_2$)$_m$—O-lower alkyl,—C(O)CH(NH$_2$)-phenyl, or oxetan-3-yl optionally substituted by CH$_2$NH$_2$, or R and R' together with the N atom to which they are attached form a heterocycloalkyl ring, optionally containing in addition to the N atom a further heteroatom, selected from the group consisting of N, S and O;

n is 1, 2 or 3;

o is 1, 2 or 3;

p is 1, 2 or 3; and m is 0, 1 or 2;

or a pharmaceutically suitable acid addition salt, optically pure enantiomer, racemate or diastereomeric mixture thereof.

11. The compound of claim 10, selected from the group consisting of
- (S)—N-(1-ethyl-3-methyl-1H-indazol-5-yl)-2-hydroxy-2-phenyl-N-[2-(6-trifluoromethyl-pyridin-3-yl)-ethyl]-acetamide;
- ((S)-2-hydroxy-2-phenyl-N-quinolin-3-yl-N-[2-(6-trifluoromethyl-pyridin-3-yl)-ethyl]-acetamide;
- (R,S)-2-(4-fluoro-phenyl)-2-hydroxy-N-(1-methyl-1H-indol-6-yl)-N-[2-(5-trifluoromethyl-pyridin-2-yl)-ethyl]-acetamide;
- (S)-2-(4-fluoro-phenyl)-2-hydroxy-N-(3-methyl-1H-indazol-5-yl)-N-[2-(6-trifluoromethyl-pyridin-3-yl)-ethyl]-acetamide; and
- (S)—N-(1,3-dimethyl-1H-indazol-5-yl)-2-(4-fluoro-phenyl)-2-hydroxy-N-[2-(6-trifluoromethyl-pyridin-3-yl)-ethyl]-acetamide.

12. The compound of claim 1, wherein $R^1$ is hydrogen, halogen, lower alkyl or lower alkyl substituted by fluoro.

13. The compound of claim 12, wherein $R^1$ is methyl, trifluoromethyl, fluoro or chloro.

14. The compound of claim 1, wherein $R^2$ is hydrogen, halogen or lower alkoxy.

15. The compound of claim 14, wherein $R^2$ is hydrogen, fluoro or chloro.

16. The compound of claim 1, wherein $R^3$ is hydrogen, halogen, cyano, lower alkyl, lower alkyl substituted by fluoro, lower alkyl substituted by hydroxy, lower alkoxy, lower alkoxy substituted by fluoro, C(O)O-lower alkyl, C(O)NH-lower alkyl or cycloalkyl.

17. The compound of claim 16, wherein $R^3$ is hydrogen, halogen, lower alkyl, lower alkyl substituted by hydroxy, lower alkoxy, lower alkoxy substituted by fluoro or C(O)O-lower alkyl.

18. The compound of claim 17, wherein $R^3$ is hydrogen, methyl, methoxy, fluoro, chloro, hydroxymethyl, difluoromethoxy or $C(O)OCH_3$.

19. The compound of claim 1, wherein $R^4$ is hydrogen or lower alkyl.

20. The compound of claim 19, wherein $R^4$ is hydrogen or methyl.

21. The compound of claim 1, wherein $R^5$ is hydrogen, $NH_2$, hydroxy, lower alkyl, $NHC(O)CH(NH_2)$-phenyl, NH(oxetan-3-yl), $NH(3-(CH_2NH_2)$-oxetan-3-yl), NH—$SO_2$-lower alkyl, NH-cycloalkyl, OC(O)-lower alkyl or $CH_2NH_2$.

22. The compound of claim 21, wherein $R^5$ is hydrogen, $NH_2$, hydroxy, $CH_3$, $NHC(O)CH(NH_2)$-phenyl, NH(oxetan-3-yl), $NH(3-(CH_2NH_2)$-oxetan-3-yl) or OC(O)—$CH_3$.

23. The compound of claim 1, wherein $R^4$ and $R^5$ together are =O.

24. The compound of claim 1, wherein $Ar^1$ is heteroaryl.

25. The compound of claim 24, wherein the heteroaryl is pyridinyl, thiazolyl, thienyl or isoxazolyl.

26. The compound of claim 1, wherein $Ar^1$ is heteroaryl.

27. The compound of claim 26, wherein the heteroaryl is pyridine-2-yl, pyridine-3-yl, thiazol-2-yl or isoxazol-5-yl.

28. The compound of claim 1, wherein $Ar^2$ is heteroaryl.

29. The compound of claim 28, wherein the heteroaryl is pyridinyl, thiazolyl, benzothiazolyl, pyrazolyl, indazolyl, quinolinyl, benzooxazolyl or indolyl.

30. The compound of claim 29, wherein the heteroaryl is pyridine-3-yl, thiazol-5-yl, pyrazol-3-yl, indazol-5-yl, quinolin-3-yl or indol-3-yl.

31. The compound of claim 1, wherein Ar is heteroaryl.

32. The compound of claim 31, wherein the heteroaryl is pyridinyl or benzoimidazolyl.

33. The compound of claim 1, wherein Ar is phenyl.

34. The compound of claim 1, wherein n is 1.

35. The compound of claim 1, wherein p is 1.

36. The compound of claim 1, wherein o is 1 or 2.

37. A pharmaceutical composition comprising a compound of formula I

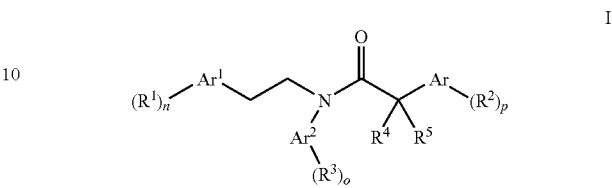

wherein
i) $Ar^1$ is heteroaryl;
   $Ar^2$ is phenyl and
   Ar is phenyl or heteroaryl; or
ii) $Ar^1$ is phenyl;
   $Ar^2$ is heteroaryl and
   Ar is phenyl or heteroaryl; or
iii) $Ar^1$ is heteroaryl;
   $Ar^2$ is heteroaryl and
   Ar is phenyl or heteroaryl;

$R^1$ is hydrogen, halogen, lower alkyl, lower alkyl substituted by halogen or lower alkoxy;

$R^2$ is hydrogen, halogen, lower alkyl, lower alkyl substituted by halogen, lower alkoxy or lower alkoxy substituted by halogen;

each $R^3$ is independently hydrogen, halogen, lower alkyl, lower alkyl substituted by halogen, lower alkyl substituted by hydroxy, lower alkyl substituted by cycloalkyl, C(O)O-lower alkyl, C(O)NH-lower alkyl, —$(CH_2)_m$—O-lower alkyl, lower alkoxy, lower alkoxy substituted by halogen, cyano, $SO_2$-lower alkyl, cycloalkyl, or where $Ar^2$ is phenyl and o is 2, $R^3$ optionally is $R^3$ and $R^{3'}$ which together with the corresponding carbon atoms to which they are attached form a non aromatic ring containing the groups —$(CH_2)_4$—, —$(CH_2)_3$—, —$CH_2$—$S(O)_2$—$CH_2$—, —$N(CH_3)$—$C(O)$—$N(CH_3)$—, —$(CH_2)_2$—O—, —O—$(CH_2)_2$—O—, —O—$(CH_2)_2$—$CH(OH)$—, —O—$(CH_2)_2$—, —O—$(CH_2)_3$—, —O—$CH_2$—$C(O)$—$N(CH_3)$—, —$N(CH_3)$—$C(O)$—$(CH_2)_2$—, or —O—$C(CH_3)_2$—O—;

$R^4$ and $R^5$ are each independently hydrogen, hydroxy, lower alkyl, lower alkoxy, $CH_2NH_2$, O—C(O)-lower alkyl, or —NRR' or $R^4$ and $R^5$ together are =O;

R and R' are each independently hydrogen, —$S(O)_2$-lower alkyl, cycloalkyl, —$(CH_2)_m$—OH, —$(CH_2)_m$—O-lower alkyl, —$C(O)CH(NH_2)$-phenyl, or oxetan-3-yl optionally substituted by $CH_2NH_2$, or R and R' together with the N atom to which they are attached form a heterocycloalkyl ring, optionally containing in addition to the N atom a further heteroatom, selected from the group consisting of N, S and O;

n is 1, 2 or 3;
o is 1, 2 or 3;
p is 1, 2 or 3; and
m is 0, 1 or 2;

or a pharmaceutically suitable acid addition salt, optically pure enantiomer, racemate or diastereomeric mixture thereof and a pharmaceutically acceptable carrier.

\* \* \* \* \*